(12) United States Patent
Witschel et al.

(10) Patent No.: US 8,809,535 B2
(45) Date of Patent: *Aug. 19, 2014

(54) SUBSTITUTED PYRIDINES HAVING HERBICIDAL ACTION

(75) Inventors: Matthias Witschel, Bad Duerkheim (DE); William Karl Moberg, Neustadt (DE); Liliana Parra Rapado, Offenburg (DE); Tao Qu, Ludwigshafen (DE); Frank Stelzer, Mannheim (DE); Andree Van Der Kloet, Heidelberg (DE); Thomas Seitz, Viernheim (DE); Thomas Ehrhardt, Speyer (DE); Klaus Kreuz, Denzlingen (DE); Klaus Grossmann, Neuhofen (DE); Anna Aleksandra Michrowska-Pianowska, Mannheim (DE); Anja Simon, Weinheim (DE); Ruediger Reingruber, Ludwigshafen (DE); Helmut Kraus, Wissembourg (FR); Dschun Song, Mannheim (DE); Julia Major, Freinsheim (DE); Johannes Hutzler, Waldsee (DE); Trevor William Newton, Neustadt (DE); Hans Wolfgang Hoeffken, Ludwigshafen (DE); Thomas Mietzner, Annweiler (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/636,430

(22) PCT Filed: Mar. 21, 2011

(86) PCT No.: PCT/EP2011/054258
§ 371 (c)(1),
(2), (4) Date: Sep. 21, 2012

(87) PCT Pub. No.: WO2011/117195
PCT Pub. Date: Sep. 29, 2011

(65) Prior Publication Data
US 2013/0023415 A1 Jan. 24, 2013

Related U.S. Application Data

(60) Provisional application No. 61/316,400, filed on Mar. 23, 2010.

(30) Foreign Application Priority Data

Mar. 23, 2010 (EP) .................................. 10157312

(51) Int. Cl.
*C07D 215/38* (2006.01)
(52) U.S. Cl.
USPC ............ 546/115; 546/116; 546/114; 504/246
(58) Field of Classification Search
USPC ............................ 546/115, 116, 114; 504/246
See application file for complete search history.

(56) References Cited

U.S. PATENT DOCUMENTS

| 5,013,659 | A | 5/1991 | Bedbrook et al. |
|---|---|---|---|
| 5,559,024 | A | 9/1996 | Leroux et al. |
| 5,846,906 | A | 12/1998 | Von Deyn et al. |
| 6,013,607 | A | 1/2000 | Otten et al. |
| 6,222,100 | B1 | 4/2001 | Anderson et al. |
| 6,479,436 | B1 | 11/2002 | Otten et al. |
| 6,689,356 | B1 | 2/2004 | Zlotkin et al. |
| 8,329,619 | B2 | 12/2012 | Song et al. |
| 8,338,337 | B2 * | 12/2012 | Song et al. ..................... 504/246 |
| 2004/0068141 | A1 | 4/2004 | Armstrong et al. |
| 2004/0077901 | A1 | 4/2004 | Ikemoto et al. |
| 2011/0201501 | A1 | 8/2011 | Song et al. |

(Continued)

FOREIGN PATENT DOCUMENTS

| EP | 0 242 236 | 10/1987 |
|---|---|---|
| EP | 0 242 246 | 10/1987 |

(Continued)

OTHER PUBLICATIONS

Bolliger, Jeanne, L., et al. "Rationally Designed Pincer-Type Heck Catalysts Bearing Aminophosphine Subtituents: $Pd^{IV}$Intermediates and Palladium Nanoparticles", Chem. Eur. J., 2008, pp. 7969-7977, vol. 14.
Gallagher, Jr., Gregory et al., "4-2[Di-n-propylamino) ethyl]-2(3H)-iodolone: A Prejunctional Dopamine Receptor Agonist", Journal of Medicinal Chemistry, 1985, pp. 1533-1536, vol. 28, Issue 10.
Ibrahim, T.M., et al., "Synthesis of 4-cyano-,Carbethoxy-and4-carboxy-pyridazine Amino Acid derivatives of expected biological activity", Egypt Journal of Chemistry, 1994, pp. 273-282, vol. 37, Issue 3.
Mallipudi, N. Moorthy, et al. "Synthesis and Insecticidal Activity of Novel N-Oxalyl-N-Methylcarbamates", J. Agric and Food Chem., 1994, pp. 1019-1025, vol. 42, Issue 4.

(Continued)

*Primary Examiner* — D M Seaman
(74) *Attorney, Agent, or Firm* — Brinks Gilson & Lione

(57) ABSTRACT

Substituted pyridines of the formula I

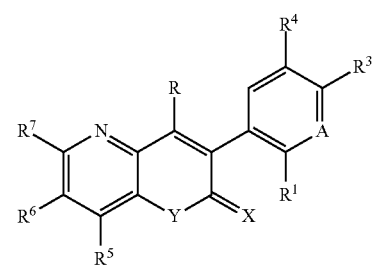

in which the variables are defined according to the description, processes and intermediates for preparing the compounds of the formula I and their N-oxides, their agriculturally suitable salts, compositions comprising them and their use as herbicides, and also methods for controlling unwanted vegetation.

27 Claims, No Drawings

(56) References Cited

U.S. PATENT DOCUMENTS

| | | |
|---|---|---|
| 2011/0224078 A1 | 9/2011 | Song et al. |
| 2011/0251063 A1 | 10/2011 | Song et al. |
| 2012/0071322 A1 | 3/2012 | Song et al. |

FOREIGN PATENT DOCUMENTS

| | | |
|---|---|---|
| EP | 0 257 993 | 3/1988 |
| EP | 0 352 543 | 1/1990 |
| EP | 0 374 753 | 6/1990 |
| EP | 0 392 225 | 10/1990 |
| EP | 0 427 529 | 5/1991 |
| EP | 0 451 878 | 10/1991 |
| WO | WO 92/00377 | 1/1992 |
| WO | WO 93/07278 | 4/1993 |
| WO | WO 95/34656 | 12/1995 |
| WO | WO 96/26193 | 8/1996 |
| WO | WO 97/30986 | 8/1997 |
| WO | WO 97/41218 | 11/1997 |
| WO | WO 98/02526 | 1/1998 |
| WO | WO 98/02527 | 1/1998 |
| WO | WO 98/52926 | 11/1998 |
| WO | WO 00/26390 | 5/2000 |
| WO | WO 01/82685 | 11/2001 |
| WO | WO 02/06211 | 1/2002 |
| WO | WO 02/15701 | 2/2002 |
| WO | WO 03/013225 | 2/2003 |
| WO | WO 03/014356 | 2/2003 |
| WO | WO 03/014357 | 2/2003 |
| WO | WO 03/018810 | 3/2003 |
| WO | WO 03/052073 | 6/2003 |
| WO | WO 2004/016073 | 2/2004 |
| WO | WO 2004/106529 | 12/2004 |
| WO | WO 2005/020673 | 3/2005 |
| WO | WO 2008/009908 | 1/2008 |
| WO | WO 2008/071918 | 6/2008 |
| WO | WO 2009/058237 | 5/2009 |
| WO | WO 2009/063180 | 5/2009 |
| WO | WO 2009/090401 | 7/2009 |
| WO | WO 2009/090402 | 7/2009 |
| WO | WO 2010/029311 | 3/2010 |
| WO | WO 2010/049269 | 5/2010 |
| WO | WO 2010/049270 | 5/2010 |
| WO | WO 2010/069802 | 6/2010 |
| WO | WO 2010/139658 | 12/2010 |
| WO | WO 2011/051212 | 5/2011 |
| WO | WO 2011/057989 | 5/2011 |
| WO | WO 2011/058036 | 5/2011 |
| WO | WO 2011/117151 | 9/2011 |
| WO | WO 2011/117152 | 9/2011 |
| WO | WO 2011/117210 | 9/2011 |
| WO | WO 2011/117211 | 9/2011 |
| WO | WO 2011/117273 | 9/2011 |

OTHER PUBLICATIONS

Picard, Franck, et al., "N-substituted 4-(4-carboxyphenoxy)benzamides. Synthesis and Evaluation as Inhibitors of Steroid-5α-reductase Type 1 and 2", Journal of Enzyme Inhibition and Medicinal Chemistry, 2002, pp. 187-196, vol. 17, Issue 3.

Silverman, Richard B., "Model studies for a Molecular Mechanism of Action of Oral Anticoagulants", J. Am. Chem. Soc., 1981, pp. 3910-3915, vol. 103, Issue 13.

Szczepankiewicz, Bruce, G., et al. "Aminopyridine-based c-Jun N-Terminal Kinase Inhibitors with Cellular Activity and Minimal Cross-Kinase Activity", Journal of Medicinal Chemistry, 2006, pp. 3563-3580, vol. 49, Issue 12.

International Search Report dated Apr. 14, 2011, prepared in International Application No. PCT/EP2011/054258, filed Mar. 21, 2011.

International Preliminary Report on Patentability dated Sep. 25, 2012, prepared in International Application No. PCT/EP2011/054258, filed Mar. 21, 2011.

Kappe, Th., et al., "Synthesis of heterocycles.160.Reaction of hydroxyl and aminopyridines with reactive malonic esters", Monatshefte Fur Chemie, Springer Verlag Wien, AT, Jan. 1, 1972, pp. 416-434, vol. 103, No. 2.

* cited by examiner

SUBSTITUTED PYRIDINES HAVING HERBICIDAL ACTION

This application is a National Stage application of International Application No. PCT/EP2011/054258, filed Mar. 21, 2011, which claims the benefit of U.S. Provisional Application No. 61/316,400, filed Mar. 23, 2010, the entire contents of which are hereby incorporated herein by reference. This application also claims priority under 35 U.S.C. §119 to European Patent Application No. 10157312.9, filed Mar. 23, 2010, the entire contents of which is hereby incorporated herein by reference.

The present invention relates to substituted pyridines of the formula I

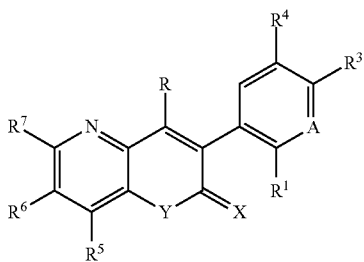

in which the variables have the following meaning:

R is $O-R^A$, $S(O)_n-R^A$ or $O-S(O)_n-R^A$;

$R^A$ is hydrogen, $C_1$-$C_4$-alkyl, $Z-C_3$-$C_6$-cycloalkyl, $C_1$-$C_4$-haloalkyl, $C_2$-$C_6$-alkenyl, $Z-C_3$-$C_6$-cycloalkenyl, $C_2$-$C_6$-alkynyl, Z-(tri-$C_1$-$C_4$-alkyl)silyl, $Z-C(=O)-R^a$, $Z-NR^i-C(O)-NR^iR^{ii}$, $Z-P(=O)(R^a)_2$, $NR^iR^{ii}$, a 3- to 7-membered monocyclic or 9- or 10-membered bicyclic saturated, unsaturated or aromatic heterocycle which contains 1, 2, 3 or 4 heteroatoms selected from the group consisting of O, N and S and which may be partially or fully substituted by groups $R^a$ and/or $R^b$, $R^a$ is hydrogen, OH, $C_1$-$C_8$-alkyl, $C_1$-$C_4$-haloalkyl, $Z-C_3$-$C_6$-cycloalkyl, $C_2$-$C_8$-alkenyl, $Z-C_5$-$C_6$-cycloalkenyl, $C_2$-$C_8$-alkynyl, $Z-C_1$-$C_6$-alkoxy, $Z-C_1$-$C_4$-haloalkoxy, $Z-C_3$-$C_8$-alkenyloxy, $Z-C_3$-$C_8$-alkynyloxy, $NR^iR^i$, $C_1$-$C_6$-alkylsulfonyl, Z-(tri-$C_1$-$C_4$-alkyl)silyl, Z-phenyl, Z-phenoxy, Z-phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^b$;

$R^i$, $R^{ii}$ independently of one another are hydrogen, $C_1$-$C_8$-alkyl, $C_1$-$C_4$-haloalkyl, $C_3$-$C_8$-alkenyl, $C_3$-$C_8$-alkynyl, $Z-C_3$-$C_6$-cycloalkyl, $Z-C_1$-$C_8$-alkoxy, $Z-C_1$-$C_8$-haloalkoxy, $Z-C(=O)-R^a$, Z-phenyl, a 3- to 7-membered monocyclic or 9- or 10-membered bicyclic saturated, unsaturated or aromatic heterocycle which contains 1, 2, 3 or 4 heteroatoms selected from the group consisting of O, N and S and which is attached via Z;

$R^i$ and $R^{ii}$ together with the nitrogen atom to which they are attached may also form a 5- or 6-membered monocyclic or 9- or 10-membered bicyclic heterocycle which contains 1, 2, 3 or 4 heteroatoms selected from the group consisting of O, N and S;

Z is a covalent bond or $C_1$-$C_4$-alkylene;

n is 0, 1 or 2;

$R^1$ is cyano, halogen, nitro, $C_1$-$C_6$-alkyl, $C_2$-$C_6$-alkenyl, $C_2$-$C_6$-alkynyl, $C_1$-$C_6$-haloalkyl, $Z-C_1$-$C_6$-alkoxy, $Z-C_1$-$C_4$-alkoxy-$C_1$-$C_4$-alkoxy, $Z-C_1$-$C_4$-alkylthio, $Z-C_1$-$C_4$-alkylthio-$C_1$-$C_4$-alkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, $S(O)_nR^{bb}$, Z-phenoxy, Z-heterocyclyloxy, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^b$;

$R^{bb}$ is $C_1$-$C_8$-alkyl, $C_2$-$C_6$-alkenyl, $C_2$-$C_6$-alkynyl, $C_2$-$C_6$-haloalkenyl, $C_2$-$C_6$-haloalkynyl or $C_1$-$C_6$-haloalkyl and n is 0, 1 or 2;

A is N or $C-R^2$;

$R^2$ is $Z^1$-phenyl, phenoxy or $Z^1$-heterocyclyl, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^b$; $C_1$-$C_8$-alkyl, $C_2$-$C_4$-haloalkyl, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_2$-$C_8$-haloalkenyl, $C_2$-$C_8$-haloalkynyl, $C_2$-$C_6$-alkoxy, $Z-C_1$-$C_4$-alkoxy-$C_1$-$C_4$-alkoxy, $Z-C_1$-$C_4$-haloalkoxy-$C_1$-$C_4$-alkoxy, $C_2$-$C_6$-haloalkoxy, $C_3$-$C_6$-alkenyloxy, $C_3$-$C_6$-alkynyloxy, $C_2$-$C_6$-alkylthio, $C_2$-$C_6$-haloalkylthio, $Z-C(=O)-R^a$, $S(O)_{1-2}R^{bb}$;

$Z^1$ is a covalent bond, $C_1$-$C_4$-alkyleneoxy, $C_1$-$C_4$-oxyalkylene or $C_1$-$C_4$-alkyleneoxy-$C_1$-$C_4$-alkylene;

$R^b$ independently of one another are $Z-CN$, $Z-OH$, $Z-NO_2$, Z-halogen, oxo(=O), =$N-R^a$, $C_1$-$C_8$-alkyl, $C_1$-$C_4$-haloalkyl, $C_2$-$C_8$-alkenyl, $C_2$-$C_8$-alkynyl, $Z-C_1$-$C_8$-alkoxy, $Z-C_1$-$C_8$-haloalkoxy, $Z-C_3$-$C_{10}$-cycloalkyl, $O-Z-C_3$-$C_{10}$-cycloalkyl, $Z-C(=O)-R^a$, $NR^iR^{ii}$, Z-(tri-$C_1$-$C_4$-alkyl)silyl, Z-phenyl and $S(O)_nR^{bb}$, two groups $R^b$ may together form a ring which has three to six ring members and, in addition to carbon atoms, may also contain heteroatoms from the group consisting of O, N and S and may be unsubstituted or substituted by further groups $R^b$;

$R^2$ together with the group attached to the adjacent carbon atom may also form a five- to ten-membered saturated or partially or fully unsaturated mono- or bicyclic ring which, in addition to carbon atoms, may contain 1, 2 or 3 heteroatoms selected from the group consisting of O, N and S and may be substituted by further groups $R^b$;

$R^3$ is hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_2$-$C_4$-alkenyloxy, $C_2$-$C_4$-alkynyloxy, $S(O)_nR^{bb}$;

$R^4$ is hydrogen, halogen or $C_1$-$C_4$-haloalkyl;

$R^5$ is hydrogen, $C_1$-$C_4$-alkyl, $C_1$-$C_4$-haloalkyl, $C_1$-$C_4$-alkoxy, $C_1$-$C_4$-alkylthio, $C_1$-$C_4$-haloalkoxy, $C_1$-$C_4$-haloalkylthio;

$R^6$, $R^7$ independently of one another are hydrogen, halogen or $C_1$-$C_4$-alkyl;

Y is O or S;

X is O, S or $N-R^x$;

$R^x$ is hydrogen, $C_1$-$C_6$-alkyl, $C_1$-$C_4$-haloalkyl, $C_2$-$C_6$-alkenyl, $C_3$-$C_6$-alkynyl, $Z-C_3$-$C_{10}$-cycloalkyl, $C_1$-$C_6$-alkoxy-$C_1$-$C_6$-alkyl, $C_1$-$C_6$-cyanoalkyl, Z-phenyl, $Z-C(=O)-R^{a2}$ or tri-$C_1$-$C_4$-alkylsilyl;

$R^{a2}$ is $C_1$-$C_6$-alkyl, $C_1$-$C_4$-haloalkyl, $Z-C_1$-$C_6$-alkoxy, $Z-C_1$-$C_4$-haloalkoxy or $NR^iR^{ii}$;

where in the groups $R^4$ and their subsubstituents, the carbon chains and/or the cyclic groups may be partially or fully substituted by groups $R^b$,
or an N-oxide or an agriculturally suitable salt thereof.

Moreover, the invention relates to processes and intermediates for preparing the pyridines of the formula I and the N-oxides thereof, the agriculturally usable salts thereof, and also to active compound combinations comprising them, to compositions comprising them and to their use as herbicides, i.e. for controlling harmful plants, and also to a method for controlling unwanted vegetation which comprises allowing a herbicidally effective amount of at least one pyridine compound of the formula I or of an agriculturally suitable salt of I to act on plants, their seed and/or their habitat.

Further embodiments of the present invention can be found in the claims, the description and the examples. It is to be understood that the features mentioned above and those still to be illustrated below of the subject matter of the invention can be applied not only in the respective given combination but also in other combinations without leaving the scope of the invention.

WO 2008/009908, WO 2008/071918, WO 2009/090401, WO 2009/090402 and WO 2010/029311 describe herbicidal pyridopyrazines; however, their herbicidal action at low application rates and/or their compatibility with crop plants leave scope for improvement.

It is an object of the present invention to provide compounds having herbicidal action. To be provided are in particular active compounds having strong herbicidal action, in particular even at low application rates, whose compatibility with crop plants is sufficient for commercial application.

These and further objects are achieved by the compounds of the formula I defined at the outset and by their N-oxides and also their agriculturally suitable salts.

The compounds according to the invention can be prepared analogously to the synthesis routes described in the abovementioned documents according to standard processes of organic chemistry, for example according to the following synthesis route:

Pyridinecarboxylic acids of the formula II can be reacted with carbonyl compounds of the formula III to give compounds of the formula IV. In the formulae II and III, the variables have the meaning given for formula I. The group Hal is a halogen atom or another suitable nucleophilic leaving group, such as alkoxy or phenoxy.

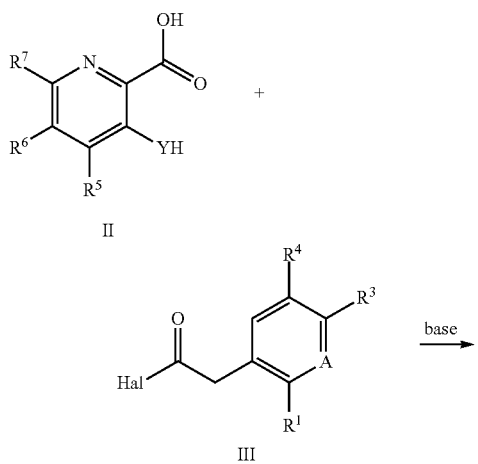

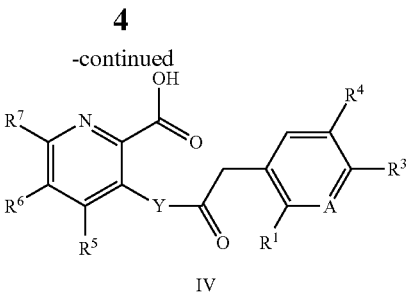

This reaction is usually carried out at temperatures of from −78° C. to 120° C., preferably from −20° C. to 50° C., in an inert organic solvent in the presence of a base, such as, for example, triethylamine (cf. J. Agric. and Food Chem. 1994, 42(4), 1019-1025), a catalyst, such as, for example, dicyclohexylcarbodiimide (cf. Egyptian Journal of Chemistry 1994, 37(3), 273-282) or other known coupling agents.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, and also dimethyl sulfoxide, dimethylformamide and dimethylacetamide, particularly preferably halogenated hydrocarbons, such as methylene chloride, chloroform and chlorobenzene. It is also possible to use mixtures of the solvents mentioned.

Suitable bases are, in general, inorganic compounds, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide and dimethoxymagnesium, moreover organic bases, for example tertiary amines, such as trimethylamine, triethylamine, tributylamine, diisopropylethylamine and N-methylpiperidine, pyridine, substituted pyridines, such as collidine, lutidine and 4-dimethylaminopyridine, and also bicyclic amines. Particular preference is given to tertiary amines such as trimethylamine, triethylamine, tributylamine, diisopropylethylamine and alkali metal and alkaline earth metal carbonates, such as lithium carbonate, potassium carbonate and calcium carbonate. The bases are generally employed in equimolar amounts; however, they can also be used in catalytic amounts, in excess or, if appropriate, as solvents.

The starting materials are generally reacted with one another in equimolar amounts.

The compounds of the formula IV are activated by introducing a leaving group $L^1$. Suitable leaving groups $L^1$ are, in general, groups which increase the electrophilicity of the carbonyl group, for example O-alkyl, O-aryl, halides, activated esters or aldehydes (such as, for example, Weinreb amide), in particular pentafluorophenoxy.

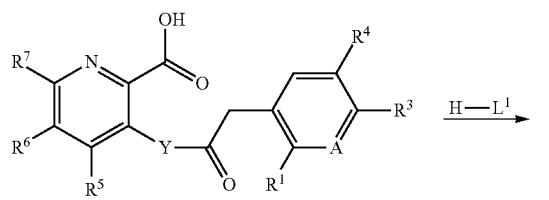

IV

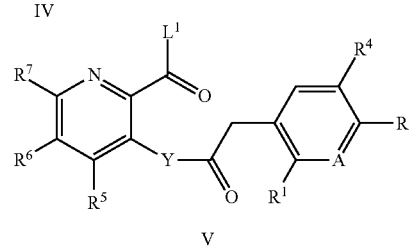

V

This reaction is usually carried out at temperatures of from −78° C. to 120° C., preferably from −20° C. to 50° C., in an inert organic solvent in the presence of a base, such as, for example, triethylamine (cf. J. Agric. and Food Chem. 1994, 42(4), 1019-1025), a catalyst, such as, for example, dicyclohexylcarbodiimide (cf. Egyptian Journal of Chemistry 1994, 37(3), 273-282) or other known coupling agents.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, and also dimethyl sulfoxide, dimethylformamide and dimethylacetamide, particularly preferably methylene chloride and toluene. It is also possible to use mixtures of the solvents mentioned.

Suitable bases are, in general, inorganic compounds, such as alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide and dimethoxymagnesium, moreover organic bases, for example tertiary amines, such as trimethylamine, triethylamine, tributylamine, diisopropylethylamine and N-methylpiperidine, pyridine, substituted pyridines, such as collidine, lutidine and 4-dimethylaminopyridine, and also bicyclic amines. Particular preference is given to alkali metal and alkaline earth metal carbonates, such as lithium carbonate, potassium carbonate, calcium carbonate, cesium carbonate and rubidium carbonate. The bases are generally employed in catalytic amounts; however, they can also be used in equimolar amounts, in excess or, if appropriate, as solvents.

The starting materials are generally reacted with one another in equimolar amounts.

Suitable agents H-L$^1$ are alcohols, optionally subst. phenols, N,O-dialkylhydroxylamine, in particular pentafluorophenol or N,O-dimethylhydroxylamine.

The compounds of the formula V are cyclized to give the compounds of the formula I.

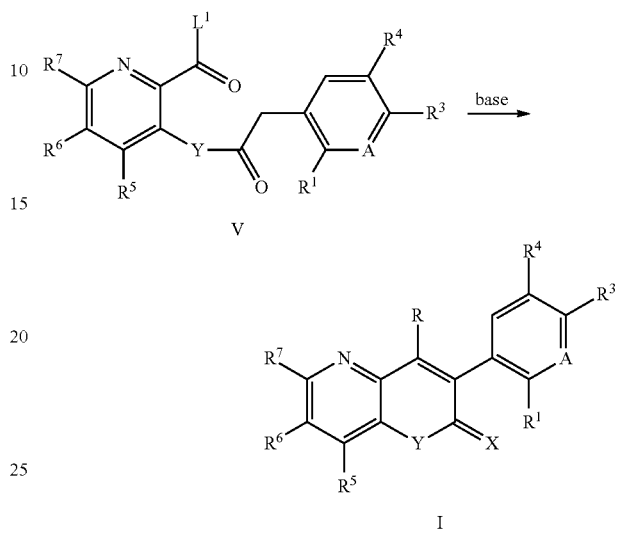

I

This reaction is usually carried out at temperatures of from −78° C. to 120° C., preferably from −20° C. to 50° C., in an inert organic solvent in the presence of a base or a Lewis acid or a catalyst [cf. Silverman, Richard B. J. Am. Chem. Soc. 1981, 103(13), 3910].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, and also dimethyl sulfoxide, dimethylformamide and dimethylacetamide, particularly preferably acetonitrile and dimethylformamide. It is also possible to use mixtures of the solvents mentioned.

Suitable bases are, in general, inorganic compounds, such as alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate, calcium carbonate, cesium carbonate and rubidium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide and dimethoxymagnesium, moreover organic bases, for example tertiary amines, such as trimethylamine, triethylamine, tributylamine, diisopropylethylamine and N-methylpiperidine, pyridine, substituted pyridines, such as collidine, lutidine and 4-dimethylaminopyridine, and also bicyclic amines. Particular preference is given to alkali metal and alkaline earth metal carbonates, such as lithium carbonate, potassium carbonate, calcium carbonate, cesium carbonate and rubidium carbonate.

The bases are generally employed in catalytic amounts; however, they can also be used in equimolar amounts, in excess or, if appropriate, as solvents.

The starting materials are generally reacted with one another in equimolar amounts.

Alternatively, the compounds of the formula I can also be obtained via a reverse reaction sequence, i.e. the reaction of the compounds of the formula II with compounds H-L¹ gives the activated derivatives of the formula VI.

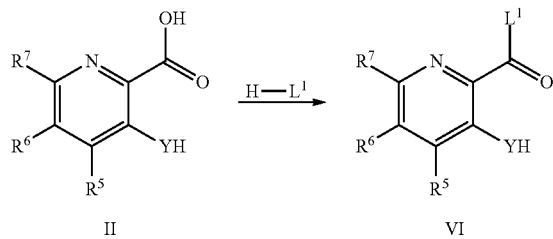

Per se, this reaction is carried out under the conditions mentioned for the reaction of the formula IV with H-L¹.

The compounds of the formula VI can then be reacted with compounds III to give the derivatives of the formula V.

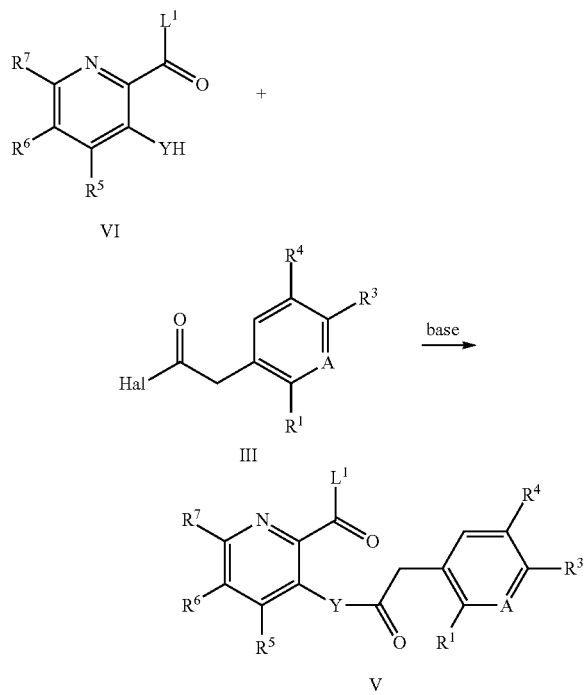

Per se, this reaction is carried out under the conditions mentioned for the reaction of the formula II with III.

The phenylacetic acid derivatives of the formula III are known or can be prepared from correspondingly substituted benzoic acids or halobenzenes on the basis of syntheses known in the literature [cf. Journal of Medicinal Chemistry 49(12), 3563-3580 (2006); Journal of Medicinal Chemistry 28(10), 1533-6 (1985); US 2004/077901; US 2004/068141; Chemistry—A European Journal 14(26), 7969-7977 (2008); Journal of Enzyme Inhibition and Medicinal Chemistry 17(3), 187-196 (2002)]. Suitably substituted benzoic acids and halobenzenes are known, for example from: WO 2002/006211, WO 2009/058237, WO 98/52926, WO 96/26193, EP-A 352 543, WO 98/52926, WO 97/30986, WO 98/12180.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, the purification can also be carried out by recrystallization or digestion.

If individual compounds I cannot be obtained by the routes described above, they can be prepared by derivatization of other compounds I.

If the synthesis yields mixtures of isomers, a separation is generally however not necessarily required since in some cases the individual isomers can be interconverted during work-up for use or during application (for example under the action of light, acids or bases). Such conversions may also take place after application, for example in the case of the treatment of plants in the treated plant or in the harmful plant to be controlled.

The organic moieties mentioned for the substituents of the compounds according to the invention are collective terms for individual enumerations of the individual group members. All hydrocarbon chains, such as alkyl, haloalkyl, alkenyl, alkynyl, and the alkyl moieties and alkenyl moieties in alkoxy, haloalkoxy, alkylamino, dialkylamino, N-alkylsulfonylamino, alkenyloxy, alkynyloxy, alkoxyamino, alkylaminosulfonylamino, dialkylaminosulfonylamino, alkenylamino, alkynylamino, N-(alkenyl)-N-(alkyl)amino, N-(alkynyl)-N-(alkyl)amino, N-(alkoxy)-N-(alkyl)amino, N-(alkenyl)-N-(alkoxy)amino or N-(alkynyl)-N-(alkoxy) amino can be straight-chain or branched.

The prefix $C_n$-$C_m$- indicates the respective number of carbons of the hydrocarbon unit. Unless indicated otherwise, halogenated substituents preferably carry one to five identical or different halogen atoms, in particular fluorine atoms or chlorine atoms.

The meaning halogen denotes in each case fluorine, chlorine, bromine or iodine.

Examples of other meanings are:

alkyl and the alkyl moieties for example in alkoxy, alkylamino, dialkylamino: saturated straight-chain or branched hydrocarbon radicals having one or more carbon atoms, for example 1 or 2, 1 to 4 or 1 to 6 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. In one embodiment according to the invention, alkyl denotes small alkyl groups, such as $C_1$-$C_4$-alkyl. In another embodiment according to the invention, alkyl denotes relatively large alkyl groups, such as $C_5$-$C_6$-alkyl.

Haloalkyl: an alkyl radical as mentioned above, some or all of whose hydrogen atoms are substituted by halogen atoms, such as fluorine, chlorine, bromine and/or iodine, for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl.

Cycloalkyl and the cycloalkyl moieties for example in cycloalkoxy or cycloalkylcarbonyl: monocyclic saturated hydrocarbon groups having three or more carbon atoms, for example 3 to 6 carbon ring members, such as cyclopropyl, cyclobutyl, cyclopentyl and cyclohexyl.

Alkenyl and the alkenyl moieties for example in alkenyloxy: monounsaturated straight-chain or branched hydrocarbon radicals having two or more carbon atoms, for example 2 to 4, 2 to 6 or 3 to 6 carbon atoms, and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

Cycloalkenyl: monocyclic monounsaturated hydrocarbon groups having 3 to 6, preferably 5 or 6, carbon ring members, such as cyclopenten-1-yl, cyclopenten-3-yl, cyclohexen-1-yl, cyclohexen-3-yl, cyclohexen-4-yl.

Alkynyl and the alkynyl moieties for example in alkynyloxy, alkynylamino: straight-chain or branched hydrocarbon groups having two or more carbon atoms, for example 2 to 4, 2 to 6 or 3 to 6 carbon atoms, and a triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl.

Alkoxy: alkyl as defined above which is attached via an oxygen atom, for example methoxy, ethoxy, n-propoxy, 1-methylethoxy, butoxy, 1-methylpropoxy, 2-methylpropoxy or 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

3- to 7-membered monocyclic or 9- or 10-membered bicyclic saturated, unsaturated or aromatic heterocycle which contains 1, 2, 3 or 4 heteroatoms selected from the group consisting of O, N and S and may be attached via carbon or nitrogen. From among these, preference is given to 5- or 6-membered heterocycles.

Saturated or unsaturated heterocyclic groups which are attached via nitrogen or carbon, such as: pyridazin-3-yl, pyridazin-4-yl, pyrimidin-2-yl, pyrimidin-4-yl, pyrimidin-5-yl, pyrazin-2-yl, isoxazolin-3-yl, isoxazolin-4-yl, isoxazolin-5-yl, isothiazol-3-yl, isothiazol-4-yl, isothiazol-5-yl, imidazol-1-yl, imidazol-2-yl, imidazol-4-yl, oxazol-2-yl, oxazolin-2-yl, thiazolin-2-yl and morpholinyl.

Heteroaromatic groups which are attached via nitrogen or carbon, such as: pyrazol-3-yl, 2-furyl, 3-furyl, 2-thienyl, 3-thienyl, pyrazol-1-yl, pyrazol-3-yl, pyrazol-4-yl, isoxazol-3-yl, isoxazol-4-yl, isoxazol-5-yl, imidazol-5-yl, oxazol-2-yl, oxazol-4-yl, oxazol-5-yl, thiazol-2-yl, thiazol-4-yl, thiazol-5-yl, pyridin-2-yl, pyridin-3-yl, pyridin-4-yl, pyrimidin-2-yl, pyrimidin-4-yl, pyrimidin-5-yl, pyridazin-4-yl, pyrazin-2-yl, [1H]-tetrazol-5-yl and [2H]-tetrazol-5-yl.

The compounds of the formula I may, depending on the substitution pattern, contain one or more further centers of chirality. Accordingly, the compounds according to the invention can be present as pure enantiomers or diastereomers or as enantiomer or diastereomer mixtures. The invention provides both the pure enantiomers or diastereomers and their mixtures.

The compounds of the formula I may also be present in the form of the N-oxides and/or of their agriculturally useful salts, the type of salt generally not being important. Suitable salts are generally the salts of those cations or the acid addition salts of those acids whose cations and anions, respectively, have no adverse effect on the herbicidal activity of the compounds I.

Suitable cations are in particular ions of the alkali metals, preferably lithium, sodium or potassium, of the alkaline earth metals, preferably calcium or magnesium, and of the transition metals, preferably manganese, copper, zinc or iron. Another cation that may be used is ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium. Another suitable ammonium cation is the pyridine nitrogen atom of the formula I quaternized by alkylation or arylation. Also suitable are phosphonium ions, sulfonium ions, preferably tri($C_1$-$C_4$-alkyl)sulfonium, or sulfoxonium ions, preferably tri($C_1$-$C_4$-alkyl)sulfoxonium.

Anions of suitable acid addition salts are primarily chloride, bromide, fluoride, hydrogensulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate, butyrate or trifluoroacetate.

With respect to the variables, the particularly preferred embodiments of the intermediates correspond to those of the groups of the formula I.

In a particular embodiment, the variables of the compounds of the formula I have the following meanings, these meanings, both on their own and in combination with one another, being particular embodiments of the compounds of the formula I:

In one preferred embodiment of the compounds of the formula I, R is O—$R^A$, in which $R^A$ is H, $C_3$-$C_8$-alkenyl, $C_3$-$C_8$-haloalkenyl, $C_3$-$C_8$-alkynyl, $C_3$-$C_8$-haloalkynyl, $C_1$-$C_6$-alkylcarbonyl, such as C(O)$CH_3$, C(O)$CH_2CH_3$, C(O)CH($CH_3$)$_2$ or C(O)C($CH_3$)$_3$; $C_1$-$C_6$-cycloalkylcarbonyl, such as cyclopropylcarbonyl, cyclopentylcarbonyl or cyclohexylcarbonyl; $C_2$-$C_6$-alkenylcarbonyl, such as C(O)CH=$CH_2$ or C(O)$CH_2$CH=$CH_2$, optionally subst. benzoyl, such as C(O)$C_6H_5$, C(O)[2-$CH_3$—$C_6H_4$], C(O)[4-$CH_3$—$C_6H_4$], C(O)[2-F—$C_6H_4$], C(O)[4-F—$C_6H_4$], or optionally subst. heteroaryl, such as pyridyl, which is attached via a carbonyl group. Particularly preferably, $R^A$ is H, $C_3$-$C_4$-alkenyl, $C_3$-$C_4$-alkynyl or $C_1$-$C_6$-alkylcarbonyl. Especially preferably, $R^A$ is selected from the group consisting of H, $CH_2$CH=$CH_2$, $CH_2$C≡CH, $CH_3$, C(O)$CH_3$, C(O)$CH_2CH_3$, C(O)CH($CH_3$)$_2$, C(O)C($CH_3$)$_3$, C(O)-c-$C_3H_5$, C(O)—$C_6H_5$, C(O)—$CH_2C_6H_5$, C(O)$CH_2$Cl, C(O)$CF_3$, C(O)$CH_2OCH_3$, C(O)N($CH_3$)$_2$ and C(O)O$CH_2CH_3$.

In a further preferred embodiment of the compounds of the formula I, R is OS(O)$_n$—$R^A$ where n is preferably 0 or 2, in particular 2, such as, for example, OS(O)$_2$—$CH_3$, OS(O)$_2$—$C_2H_5$, OS(O)$_2$—$C_3H_7$, OS(O)$_2$—$C_6H_5$ or OS(O)$_2$-(4-$CH_3$—$C_6H_4$).

In a further preferred embodiment, R is O—S(O)$_n$—NR$^i$R$^{ii}$, in particular with the groups NR$^i$R$^{ii}$ mentioned below as preferred.

R$^i$ and R$^{ii}$ are preferably $C_1$-$C_8$-alkyl, $C_1$-$C_4$-haloalkyl, Z—$C_3$-$C_6$-cycloalkyl, Z—$C_1$-$C_8$-alkoxy, Z—$C_1$-$C_8$-haloalkoxy, Z-phenyl, Z—C(=O)—$R^a$ or Z-hetaryl. Preference is given here to $CH_3$, $C_2H_5$, n-propyl, CH($CH_3$)$_2$, butyl, 2-choroethyl, cyclopentyl, cyclohexyl, 2-ethoxymethyl, 2-chloroethoxy, phenyl, pyrimidines or triazines, which rings are unsubstituted or substituted. Preferred substituents are $C_1$-$C_4$-alkylcarbonyl or $C_1$-$C_4$-haloalkylcarbonyl, in particular C(=O)—$CH_3$, C(=O)—$C_2H_5$, C(=O)—$C_3H_7$, C(=O)—CH($CH_3$)$_2$, butylcarbonyl and C(=O)—$CH_2$Cl. Particularly preferred aspects of group NR$^i$R$^{ii}$ are N(di-$C_1$-$C_4$-alkyl), in particular N($CH_3$)—$C_1$-$C_4$-alkyl, such as N($CH_3$)$_2$, N($CH_3$)$CH_2CH_3$, N($CH_3$)$C_3H_7$ and N($CH_3$)CH($CH_3$)$_2$.

Further particularly preferred aspects of NR$^i$R$^{ii}$ are NH-aryl, where aryl is preferably phenyl which is substituted—in particular in the 2- and 6-position—by one to three identical or different groups from the group consisting of halogen, $CH_3$, halo-$C_1$-$C_2$-alkyl, halo-$C_1$-$C_2$-alkoxy and carboxyl, such as 2-Cl,6-COOH—$C_6H_3$, 2,6-$Cl_2$-$C_6H_3$, 2,6-$F_2$—$C_6H_3$, 2,6-$Cl_2$ 3-$C_6H_2$, 2-$CF_3$,6-$CH_2$CH$F_2$—$C_6H_3$, 2-$CF_3$, 6-O$CF_3$—$C_6H_3$ and 2-$CF_3$,6-$CH_2$CH$F_2$—$C_6H_3$.

In a further preferred embodiment of the invention, $R^A$ is a 5- or 6-membered heterocycle optionally substituted by $R^b$ as defined above, which preferably has either 1, 2, 3 or 4 N or 1 O or 1 S atom and if appropriate 1 or 2 N atoms as ring members and which is unsubstituted or may have 1 or 2 substituents selected from $R^b$. Preference is given to saturated or unsaturated groups attached via nitrogen, such as, for example:

Heteroaromatic groups: pyridazin-3-yl, pyridazin-4-yl, pyrimidin-2-yl, pyrimidin-4-yl, pyrimidin-5-yl, pyrazin-2-yl, 2-furyl, 3-furyl, 2-thienyl, 3-thienyl, pyrazol-1-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-1-yl, imidazol-2-yl, imidazol-4-yl, oxazol-2-yl, oxazol-4-yl, oxazol-5-yl, thiazol-2-yl, thiazol-4-yl and thiazol-5-yl.

In another aspect, $R^A$ is a heteroaromatic group attached via carbon, such as pyrazol-3-yl, imidazol-5-yl, oxazol-2-yl, thiazol-2-yl, thiazol-4-yl, thiazol-5-yl, pyridin-2-yl, pyridin-3-yl, pyridin-4-yl, pyrimidin-2-yl, pyrimidin-4-yl, pyrimidin-5-yl, pyridazin-4-yl, pyrazin-2-yl, [1H]-tetrazol-5-yl and [2H]-tetrazol-5-yl, where each of the heterocycles mentioned here in an exemplary manner may have 1 or 2 substituents selected from $R^b$. Preferred groups $R^b$ are in this case in particular F, Cl, CN, $NO_2$, $CH_3$, $O_2H_5$, $OCH_3$, $OC_2H_5$, OCHF$_2$, OCF$_3$ and CF$_3$.

In particularly preferred embodiments of the compounds of the formula I, R is selected from the group consisting of OH, O$CH_2$CH=$CH_2$, O$CH_2$C≡CH, O$CH_3$, OC(O)$CH_3$, OC(O)$CH_2CH_3$, OC(O)CH($CH_3$)$_2$, OC(O)C($CH_3$)$_3$, OC(O)-c-$C_3H_5$, OC(O)—$C_6H_5$, OC(O)—$CH_2C_6H_5$, OC(O)$CH_2$Cl, OC(O)—$CF_3$, OC(O)—$CH_2OCH_3$, OC(O)—N($CH_3$)$_2$ and OC(O)—O$CH_2CH_3$.

Groups $R^a$ preferred for the compounds of the formula I are selected from the group consisting of OH, $C_1$-$C_8$-alkyl, $C_1$-$C_4$-haloalkyl, $C_3$-$C_8$-alkenyl, $C_3$-$C_8$-alkynyl, Z—$C_1$-$C_6$-alkoxy, Z—$C_1$-$C_4$-haloalkoxy, Z—$C_3$-$C_8$-alkenyloxy, Z—$C_3$-$C_8$-alkynyloxy and NR$^i$R$^{ii}$.

For the compounds of the formula I, the groups $R^b$ are preferably selected from the group consisting of halogen, oxo (=O), =N—$R^a$, $C_1$-$C_4$-alkyl, $C_1$-$C_4$-haloalkyl, $C_2$-$C_6$-alkenyl, $C_2$-$C_6$-alkynyl, Z—$C_1$-$C_4$-haloalkoxy, $C_1$-$C_4$-alkoxy-$C_1$-$C_4$-alkyl, $C_1$-$C_4$-alkylthio-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkylthio-$C_1$-$C_4$-alkyl, Z—C(=O)—$R^a$ and S(O)$_n$R$^{bb}$, where R$^{bb}$ is preferably $C_1$-$C_4$-alkyl or $C_1$-$C_4$-haloalkyl and n is 0, 1 or 2.

Particularly preferably, $R^b$ is a group selected from the group consisting of halogen, $C_1$-$C_4$-alkyl, $C_1$-$C_4$-haloalkyl, $C_1$-$C_4$-alkoxy, $C_1$-$C_4$-alkylthio, $C_1$-$C_4$-alkoxy-$C_1$-$C_4$-alkyl, $C_1$-$C_4$-alkylthio-$C_1$-$C_4$-alkyl, $C_1$-$C_4$-alkoxy-$C_1$-$C_4$-alkoxy-$C_1$-$C_4$-alkyl, $C_1$-$C_4$-haloalkoxy, $C_1$-$C_4$-haloalkylthio, $C_3$-$C_4$-alkenyl, $C_3$-$C_4$-alkynyl and =N—$C_1$-$C_4$-alkoxy.

Two groups $R^b$ together may form a ring which preferably has three to seven ring members and, in addition to carbon atoms, may also contain heteroatoms from the group consisting of O, N and S and which may be unsubstituted or substituted by further groups $R^b$. These substituents $R^b$ are preferably selected from the group consisting of halogen, $C_1$-$C_4$-alkyl, $C_1$-$C_4$-alkoxy and $C_1$-$C_4$-haloalkyl.

Groups $R^a$ and $R^b$ are selected independently of one another if a plurality of such groups is present.

In a preferred embodiment of the compounds of the formula I, $R^1$ is halogen, CN, $NO_2$, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkyl, $C_1$-$C_4$-alkylthio-$C_1$-$C_4$-alkylthio-$C_1$-$C_4$-alkyl, $C_1$-$C_4$-alkoxy, $C_1$-$C_4$-haloalkoxy, $C_3$-$C_4$-alkenyloxy, $C_3$-$C_4$-alkynyloxy, $C_1$-$C_4$-alkoxy-$C_1$-$C_4$-alkoxy, $C_1$-$C_4$-haloalkoxy-$C_1$-$C_4$- alkoxy, S(O)$_n$—C$_1$-C$_4$-alkyl and S(O)$_n$—C$_1$-C$_4$-haloalkyl. Particularly preferably, R$^1$ is selected from the group consisting of F, Cl, Br, NO$_2$, CH$_3$, CF$_3$, OCH$_3$, OCF$_3$, SCF$_3$, SO$_2$CH$_3$, OCH$_2$CH$_2$OCH$_3$, CH$_2$OCH$_2$CH$_2$OCH$_3$, CH$_2$OCH$_2$CF$_3$.

In a further preferred embodiment of the compounds of the formula I, A is C—R$^2$. These compounds correspond to the formula I.1

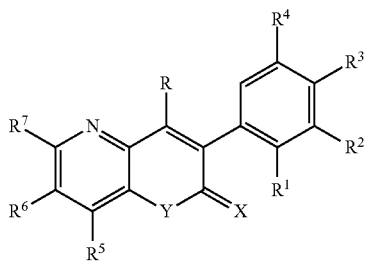

I.1 where the variables have the meanings defined at the outset and preferably the meanings mentioned as preferred.

Particularly preferably, in the compounds of the formula I.1, the group

R$^1$ is halogen, C$_1$-C$_4$-alkyl, C$_1$-C$_4$-haloalkyl, C$_1$-C$_4$-alkoxy-C$_1$-C$_4$-alkyl, C$_1$-C$_4$-alkoxy-C$_1$-C$_4$-alkoxy-C$_1$-C$_4$-alkyl, C$_1$-C$_4$-alkoxy, C$_1$-C$_4$-haloalkoxy, C$_1$-C$_4$-alkylthio, C$_1$-C$_4$-haloalkylthio or C$_1$-C$_4$-alkylsulfonyl, in particular F, Cl, Br, NO$_2$, CH$_3$, CF$_3$, OCH$_3$, OCF$_3$, OCHF$_2$, SCF$_3$, SCHF$_2$, SO$_2$CH$_3$, CH$_2$OCH$_2$CH$_2$OCH$_3$;

R$^3$ is H, halogen, CN, NO$_2$, C$_1$-C$_4$-alkyl, C$_1$-C$_4$-haloalkyl, C$_1$-C$_4$-alkoxy, C$_1$-C$_4$-alkylthio, C$_1$-C$_4$-alkylsulfonyl, in particular H, F, Cl, Br, CN, NO$_2$, CH$_3$, CH$_2$CH$_3$, CF$_3$, CHF$_2$, OCH$_3$, OCF$_3$, OCHF$_2$, SCH$_3$, SO$_2$CH$_3$ or SO$_2$CH$_2$CH$_3$;

R$^4$ is H or halogen, in particular H, F or Cl.

R$^2$ is preferably phenyl or a 3- to 7-membered monocyclic or 9- or 10-membered bicyclic saturated, partially unsaturated or aromatic heterocycle which is attached via Z$^1$ and contains 1, 2, 3 or 4 heteroatoms selected from the group consisting of O, N and S, where the cyclic groups are unsubstituted or partially or fully substituted by groups R$^b$.

In a preferred aspect of the compounds of the formula I.1, R$^2$ is a 3- to 7-membered monocyclic or 9- or 10-membered bicyclic saturated, partially unsaturated or aromatic heterocycle which is attached directly or via C$_1$-C$_4$-alkyleneoxy, C$_1$-C$_4$-oxyalkylene or C$_1$-C$_4$-alkyleneoxy-C$_1$-C$_4$-alkylene, which contains 1, 2, 3 or 4 heteroatoms selected from the group consisting of O, N and S and which may be substituted as defined at the outset.

A preferred aspect of group R$^2$ relates to five- or six-membered saturated or partially unsatured heterocycles, such as, for example, isoxazoline, tetrazolone, 1,2-dihydrotetrazolone, 1,4-dihydrotetrazolone, tetrahydrofuran, dioxolane, piperidine, morpholine and piperazine. Particular preference is given to 3-isoxazoline, 5-isoxazoline, 1-tetrazolone, 2-tetrazolone, [1,3]dioxolane-2 and N-morpholine. Especially preferred are: 4,5-dihydroisoxazole-3, unsubstituted or substituted by 5-CH$_3$, 5-CH$_2$F or 5-CHF$_2$; 4,5-dihydroisoxazole-5, unsubstituted or substituted by 3-CH$_3$, 3-OCH$_3$, 3-CH$_2$OCH$_3$, 3-CH$_2$SCH$_3$; 1-methyl-5-oxo-1,5-dihydrotetrazole-2; 4-methyl-5-oxo-4,5-dihydrotetrazole-1 and N-morpholine.

A further preferred aspect of group R$^2$ relates to five- or six-membered aromatic heterocycles, such as, for example, isoxazole, pyrazole, thiazole, furyl, pyridine, pyrimidine and pyrazine. Particular preference is given to 3-isoxazole, 5-isoxazole, 3-pyrazole, 5-pyrazole, 2-thiazole, 2-oxazole, 2-furyl. Especially preferred are: 3-isoxazole, 5-methyl-3-isoxazole, 5-isoxazole, 3-methyl-5-isoxazole, 1-methyl-1H-pyrazole-3,2-methyl-2H-pyrazole-3 and thiazole-2.

In a preferred aspect of heterocyclic groups R$^2$, the groups R$^b$ are preferably C$_1$-C$_4$-alkyl, C$_1$-C$_4$-haloalkyl, C$_1$-C$_4$-alkoxy, C$_1$-C$_4$-alkoxy-C$_1$-C$_4$-alkyl, C$_1$-C$_4$-alkylthio-C$_1$-C$_4$-alkyl, C$_1$-C$_4$-alkylthio or C$_1$-C$_4$-alkylsulfonyl. Especially preferred are CH$_3$, C$_2$H$_5$, CH$_2$F, CF$_2$H, CF$_3$, OCH$_3$, CH$_2$OCH$_3$, CH$_2$SCH$_3$, SCH$_3$ and SO$_2$CH$_3$.

In a preferred aspect, the group Z$^1$ is a covalent bond.

In a further preferred aspect, the group Z$^1$ is C$_1$-C$_4$-alkyleneoxy, in particular OCH$_2$ or OCH$_2$CH$_2$.

In a further preferred aspect, the group Z$^1$ is C$_1$-C$_4$-oxyalkylene, in particular CH$_2$O or CH$_2$CH$_2$O.

In a further preferred aspect, the group Z$^1$ is C$_1$-C$_4$-alkyleneoxy-C$_1$-C$_4$-alkylene, in particular OCH$_2$OCH$_2$ or OCH$_2$CH$_2$OCH$_2$.

Particularly preferred aspects of heterocycles attached via Z$^1$ include tetrahydrofuran-2-ylmethoxymethyl and [1,3]dioxolan-2-ylmethoxy.

In a further preferred aspect of the compounds of the formula I.1, R$^2$ is phenyl which may be partially or fully substituted—preferably mono-, di- or trisubstituted, in particular monosubstituted—by groups R$^b$. Groups R$^b$ preferred for this aspect include: halogen, C$_1$-C$_4$-alkyl, C$_1$-C$_4$-alkoxy, C$_1$-C$_4$-haloalkyl, C$_1$-C$_4$-alkoxy-C$_1$-C$_4$-alkyl, C$_1$-C$_4$-alkoxy-C$_1$-C$_4$-alkoxy-C$_1$-C$_4$-alkyl, C$_1$-C$_4$-alkoxy-C$_1$-C$_4$-alkoxy, C$_1$-C$_4$-alkoxy-C$_1$-C$_4$-alkoxy-C$_1$-C$_4$-alkoxy. Particular preference is given to halogen, such as F or Cl, CH$_3$, O$_2$H$_5$, OCH$_3$, OC$_2$H$_5$, CHF$_2$, CF$_3$, OCHF$_2$, OCF$_3$, OCH$_2$OCH$_3$, OCH$_2$CH$_2$OCH$_3$. Special preference is given to alkoxy, such as OCH$_3$ or OC$_2$H$_5$. A group R$^b$ is preferably in position 4. A particularly preferred phenyl group R$^2$ is a group P:

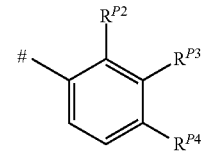

in which # denotes the bond via which the group R$^2$ is attached and the substituents are selected from R$^b$ and are in particular:

R$^{P2}$ H or F;
R$^{P3}$ H, F, Cl or OCH$_3$; and
R$^{P4}$ H, F, Cl, CH$_3$, CF$_3$, OCH$_3$, OCH$_2$OCH$_3$ or OCH$_2$CH$_2$OCH$_3$.

In a further preferred aspect of the compounds of the formula I.1, R$^2$ is an aliphatic group selected from the group consisting of C$_1$-C$_6$-alkyl, C$_1$-C$_4$-alkoxy-C$_1$-C$_4$-alkyl, C$_1$-C$_4$-haloalkoxy-C$_1$-C$_4$-alkyl, C$_2$-C$_6$-alkenyl, C$_2$-C$_6$-alkynyl, C$_2$-C$_4$-alkoxy, C$_2$-C$_4$-haloalkoxy, C$_3$-C$_6$-alkenyloxy, C$_3$-C$_6$-alkynyloxy, C$_3$-C$_6$-haloalkenyloxy, C$_3$-C$_6$-haloalkynyloxy, C$_1$-C$_4$-alkoxycarbonyl, S(O)$_2$—C$_1$-C$_4$-alkyl and S(O)$_2$—C$_1$-C$_8$-haloalkyl.

Particularly preferred aliphatic groups R$^2$ include C$_2$-C$_4$-alkenyl, C$_2$-C$_4$-alkynyl, C$_1$-C$_2$-halo-alkoxy-C$_1$-C$_2$-alkyl, C$_3$-C$_4$-alkenyloxy, C$_3$-C$_4$-alkynyloxy, C$_1$-C$_4$-alkylsulfonyl, C$_2$-C$_4$-alkoxy, C$_1$-C$_4$-alkoxycarbonyl and S(O)$_2$—C$_1$-C$_4$-alkyl. Special preference is given to CH═CH$_2$, CH═CHCH$_3$, CH$_2$OCH$_2$CF$_3$, OC$_2$H$_5$, OCH$_2$CH═CH$_2$, OCH$_2$C≡CH, OCH$_2$CH$_2$OCH$_3$, COOCH$_3$, COOC$_2$H$_5$ and SO$_2$CH$_3$, SO$_2$C$_2$H$_5$ and SO$_2$CH(CH$_3$)$_2$.

In a further preferred aspect, R$^2$ together with R$^1$ or R$^3$ forms a five- to ten-membered mono- or bicyclic, saturated or partially unsaturated ring which contains 1, 2, 3 or 4 heteroatoms selected from the group consisting of O, N and S and which may be partially or fully substituted by groups R$^b$. Together with the phenyl group which carries the groups R$^1$ to R$^5$, a nine- to fifteen-membered bi- or tricyclic, optionally heterocyclic, ring system results. Suitable are, for example, the following: 2,3-dihydrobenzo[b]thiophene 1,1-dioxide, thiochroman 1,1-dioxide, 2,3-dihydrobenzo[1,4]dithiin 1,1,4,4-tetraoxide, 3H-benzothiazol-2-one, quinoline and saccharin.

Preferably, R$^2$ together with R$^1$ or R$^3$ forms a five- or six-membered monocyclic, saturated or partially unsaturated ring.

Preferred bicyclic ring systems comprising the phenyl group attached to the naphthyridinone skeleton and R$^1$ and R$^2$ are, for example, groups A to D:

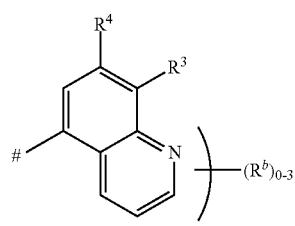

A

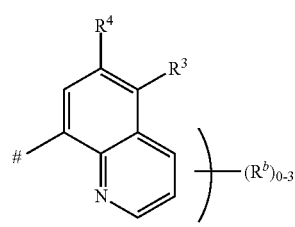

B

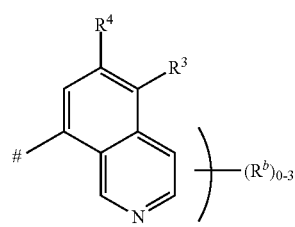

C

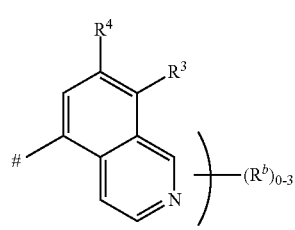

D denotes the bond to the skeleton.

Preferred bi- and tricyclic ring systems comprising the phenyl group attached to the naphthyridinone skeleton and R$^2$ and R$^3$ contain one or two sulfur atoms and optionally one nitrogen atom. Preferred are groups E to L:

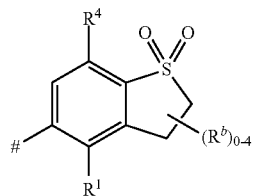

E

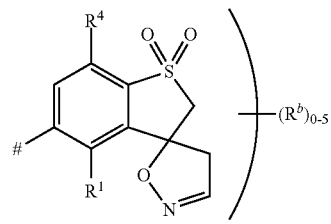

F

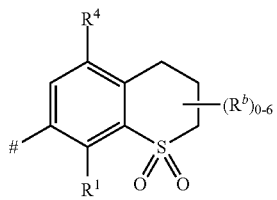

G

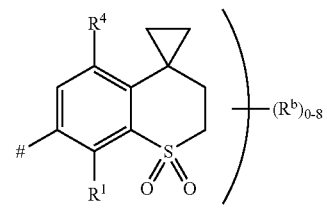

H

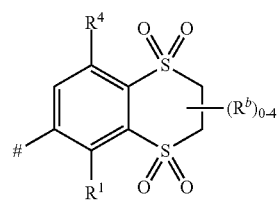

I

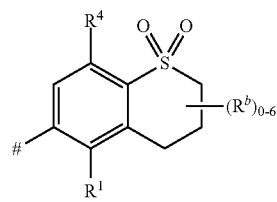

J

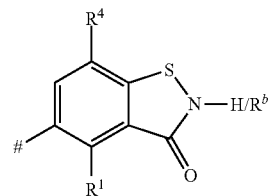

K

-continued

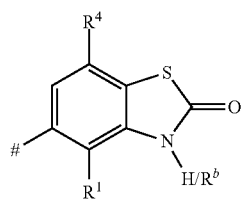
L

In groups A to L, the groups $R^b$ independently of one another are preferably halogen, $C_1$-$C_4$-alkyl, $C_1$-$C_4$-alkoxy, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio, $C_1$-$C_4$-haloalkyl, $C_1$-$C_4$-haloalkoxy, $C_1$-$C_4$-haloalkylthio, $C_3$-$C_4$-alkenyl, $C_3$-$C_4$-alkynyl, =N—$C_1$-$C_4$-alkoxy.

The compounds of the formula I in which $R^2$ is one of groups A to L correspond to the formulae I.A to I.L.

In the formulae I.A to I.L, $R^b$ is preferably halogen, $C_1$-$C_4$-alkyl, $C_1$-$C_4$-alkoxy or $C_1$-$C_4$-haloalkyl.

The following examples represent particularly preferred groups A to L:

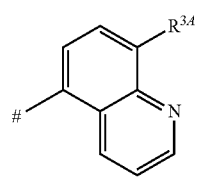
A.1

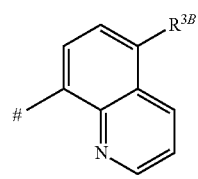
B.1

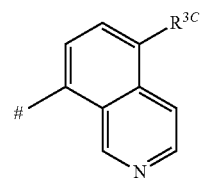
C1

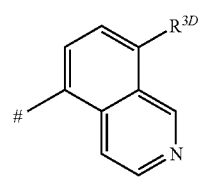
D1

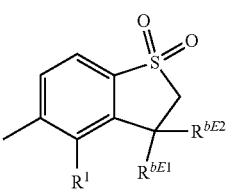
E1

-continued

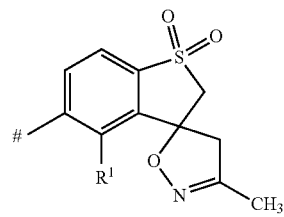
F1

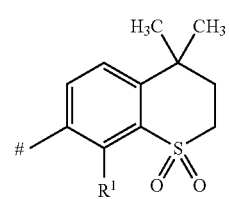
G1

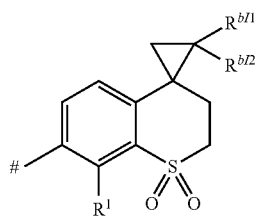
H1

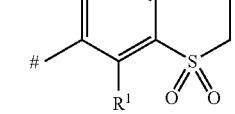
I1

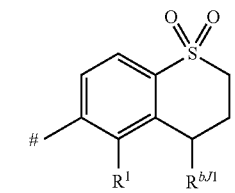
J1

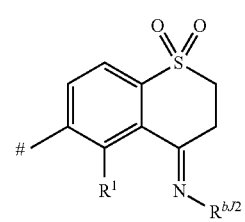
J2

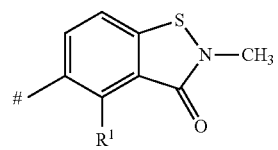
K1

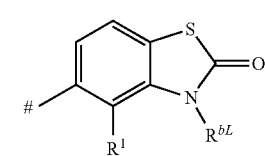
L1

$R^{3A}$, $R^{3B}$, $R^{3C}$ and $R^{3D}$ are preferably halogen, $C_1$-$C_4$-alkyl, $C_1$-$C_4$-haloalkyl, $C_1$-$C_4$-alkoxy, in particular F, Cl, Br, $CH_3$, $CF_3$ or $OCH_3$.

$R^{bE1}$, $R^{bE2}$ are preferably H, $C_1$-$C_4$-alkyl or $C_1$-$C_4$-alkoxy, in particular $R^{bE1}$ is H or $CH_3$; $R^{bE2}$ is H, $CH_3$ or $OCH_3$.

$R^{bJ1}$ is preferably $C_1$-$C_4$-haloalkoxy, in particular $OCH_2CH_2F$.

$R^{bJ2}$ is preferably $C_1$-$C_4$-alkoxy, in particular $OCH_3$ or $OCH_2CH_3$.

$R^{bL}$ is preferably $C_1$-$C_4$-Alkyl or $C_3$-$C_4$-Alkenyl, in particular $CH_3$, $CH_2CH_3$, $CH_2CH_2CH_3$, $CH(CH_3)_2$ or $CH_2CH\!=\!CH_2$.

In a further preferred embodiment of the compounds of the formula I, A is N. These compounds correspond to formula I.2,

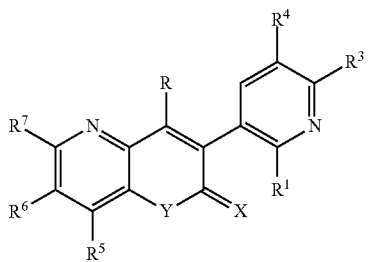

I.2 in which the variables have the meanings defined at the outset and preferably those mentioned above. Especially preferably, in compounds of the formula I.2 the group $R^1$ is nitro, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular $NO_2$, $CH_3$, $CF_3$, $CH_2OCH_2CH_2OCH_3$, $OCH_3$, $OCF_3$, $OCHF_2$, $SCF_3$, $SCHF_2$, $SO_2CH_3$;

$R^3$ is H, CN, $NO_2$, $C_1$-$C_4$-alkyl, $C_1$-$C_4$-haloalkyl, $C_1$-$C_4$-alkoxy, $C_1$-$C_4$-alkylthio, $C_1$-$C_4$-alkylsulfonyl, in particular H, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$.

In a further preferred embodiment of the compounds of the formula I, in particular of the formula I.1, $R^3$ is hydrogen, halogen, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_n$—$C_1$-$C_4$-alkyl or $S(O)_n$—$C_1$-$C_4$-haloalkyl, where n is preferably 0 or 2. Particularly preferably, $R^3$ is selected from the group consisting of H, F, Cl, Br, CN, $NO_2$, $CH_3$, $CF_3$, $CHF_2$, $OCH_3$, $OCF_3$, $OCHF_2$, $SCH_3$, $SCF_3$, $SCHF_2$, $SO_2CH_3$, $SO_2CH_2CH_3$.

In a further preferred embodiment of the compounds of the formula I, $R^4$ is hydrogen or halogen, particularly preferably H, F or Cl, in particular H.

In a further preferred embodiment of the compounds of the formula I, $R^5$ is hydrogen, $C_1$-$C_4$-alkyl, $C_1$-$C_4$-haloalkyl, $C_1$-$C_4$-alkoxy, $C_1$-$C_4$-alkylthio, $C_1$-$C_4$-haloalkoxy or $C_1$-$C_4$-haloalkylthio, particularly preferably H, $CH_3$, $CF_3$, $CHF_2$, $OCH_3$, $OCF_3$, $OCHF_2$, $SCH_3$, $SCF_3$, $SCHF_2$, in particular H.

In a further preferred embodiment of the compounds of the formula I, at least one of the groups $R^6$ and $R^7$, preferably both groups, is/are hydrogen.

In a preferred embodiment, X is O.
In a further embodiment, X is S.
In a further embodiment, X is $NR^x$.
In a preferred embodiment, Y is O.
In a further embodiment, Y is S.

$R^x$ is preferably H, $C_1$-$C_6$-alkyl, such as $CH_3$, $C_2H_5$, n-$C_3H_7$, $CH(CH_3)_2$, n-$C_3H_9$, or $C(CH_3)_3$; $C_3$-$C_6$-cycloalkyl-$C_1$-$C_4$-alkyl, such as cyclopropylmethyl, $C_3$-$C_6$-alkenyl, such as $CH_2CH\!=\!CH_2$, $CH_2C(CH_3)\!=\!CH_2$, $CH_2CH_2CH\!=\!CH_2$, $CH_2CH_2C(CH_3)\!=\!CH_2$, $CH_2CH_2CH\!=\!CH_2$, $CH_2CH_2CH_2C(CH_3)\!=\!CH_2$, or optionally subst. phenyl, such as $C_6H_5$, 4-$CH_3$—$C_6H_4$, 4-F—$C_6H_4$ or $S(O)_n$—$R^N$, where $R^N$ is $C_1$-$C_6$-haloalkyl, such as $CH_2CF_3$, $CH_2CHF_2$.

A further embodiment relates to the N-oxides of the compounds of the formula I.

A further embodiment relates to salts of the compounds of the formula I, in particular those which are obtainable by quaternization of the pyridine nitrogen atom, which may preferably take place by alkylation or arylation of the compounds of the formula I. Preferred salts of the compounds are thus the N-alkyl salts, in particular the N-methyl salts, and the N-phenyl salts.

In particular with a view to their use, preference is given to the compounds of the formula I compiled in the tables below, which compounds correspond to the formulae I.1A and I.2A. The groups mentioned for a substituent in the tables are furthermore per se, independently of the combination in which they are mentioned, a particularly preferred aspect of the substituent in question.

Table 1
Compounds of the formula I in which X and Y are O, R is OH, $R^5$ is H and the combination of $R^1$, $R^3$ and if appropriate $R^2$ for a compound corresponds in each case to one row of table A or is specified in table A.1 or A.2

Table 2
Compounds of the formula I in which X and Y are O, R is $OCH_2CH\!=\!CH_2$, $R^5$ is H and the combination of $R^1$, $R^3$ and if appropriate $R^2$ for a compound corresponds in each case to one row of table A or is specified in table A.1 or A.2

Table 3
Compounds of the formula I in which X and Y are O, R is $OCH_2C\!\equiv\!CH$, $R^5$ is H and the combination of $R^1$, $R^3$ and if appropriate $R^2$ for a compound corresponds in each case to one row of table A or is specified in table A.1 or A.2

Table 4
Compounds of the formula I in which X and Y are O, R is OH, $R^5$ is $CH_3$ and the combination of $R^1$, $R^3$ and if appropriate $R^2$ for a compound corresponds in each case to one row of table A or is specified in table A.1 or A.2

Table 5
Compounds of the formula I in which X and Y are O, R is $OCH_2CH\!=\!CH_2$, $R^5$ is $CH_3$ and the combination of $R^1$, $R^3$ and if appropriate $R^2$ for a compound corresponds in each case to one row of table A or is specified in table A.1 or A.2

Table 6
Compounds of the formula I in which X and Y are O, R is $OCH_2C\!\equiv\!CH$, $R^5$ is $CH_3$ and the combination of $R^1$, $R^3$ and if appropriate $R^2$ for a compound corresponds in each case to one row of table A or is specified in table A.1 or A.2

Table 7
Compounds of the formula I in which X and Y are O, R is OH, $R^5$ is $CH_2CH_3$ and the combination of $R^1$, $R^3$ and if appropriate $R^2$ for a compound corresponds in each case to one row of table A or is specified in table A.1 or A.2

Table 8
Compounds of the formula I in which X and Y are O, R is $OCH_2CH\!=\!CH_2$, $R^5$ is $CH_2CH_3$ and the combination of $R^1$, $R^3$ and if appropriate $R^2$ for a compound corresponds in each case to one row of table A or is specified in table A.1 or A.2

Table 9
Compounds of the formula I in which X and Y are O, R is $OCH_2C\!\equiv\!CH$, $R^5$ is $CH_2CH_3$ and the combination of $R^1$, $R^3$ and if appropriate $R^2$ for a compound corresponds in each case to one row of table A or is specified in table A.1 or A.2

Table 10
Compounds of the formula I in which X and Y are O, R is OH, $R^5$ is $OCH_3$ and the combination of $R^1$, $R^3$ and if appropriate $R^2$ for a compound corresponds in each case to one row of table A or is specified in table A.1 or A.2

Table 11
Compounds of the formula I in which X and Y are O, R is $OCH_2CH=CH_2$, $R^5$ is $OCH_3$ and the combination of $R^1$, $R^3$ and if appropriate $R^2$ for a compound corresponds in each case to one row of table A or is specified in table A.1 or A.2

Table 12
Compounds of the formula I in which X and Y are O, R is $OCH_2C\equiv CH$, $R^5$ is $OCH_3$ and the combination of $R^1$, $R^3$ and if appropriate $R^2$ for a compound corresponds in each case to one row of table A or is specified in table A.1 or A.2

Table 13
Compounds of the formula I in which X and Y are O, R is OH, $R^5$ is $SCH_3$ and the combination of $R^1$, $R^3$ and if appropriate $R^2$ for a compound corresponds in each case to one row of table A or is specified in table A.1 or A.2

Table 14
Compounds of the formula I in which X and Y are O, R is $OCH_2CH=CH_2$, $R^5$ is $SCH_3$ and the combination of $R^1$, $R^3$ and if appropriate $R^2$ for a compound corresponds in each case to one row of table A or is specified in table A.1 or A.2

Table 15
Compounds of the formula I in which X and Y are O, R is $OCH_2C\equiv CH$, $R^5$ is $SCH_3$ and the combination of $R^1$, $R^3$ and if appropriate $R^2$ for a compound corresponds in each case to one row of table A or is specified in table A.1 or A.2

Table 16
Compounds of the formula I in which X is O and Y is S, R is OH and $R^5$ is H and the combination of $R^1$, $R^3$ and if appropriate $R^2$ for a compound corresponds in each case to one row of table A or is specified in table A.1 or A.2

Table 17
Compounds of the formula I in which X is O and Y is S, R is $OCH_2CH=CH_2$, $R^5$ is H and the combination of $R^1$, $R^3$ and if appropriate $R^2$ for a compound corresponds in each case to one row of table A or is specified in table A.1 or A.2

Table 18
Compounds of the formula I in which X is O and Y is S, R is $OCH_2C\equiv CH$, $R^5$ is H and the combination of $R^1$, $R^3$ and if appropriate $R^2$ for a compound corresponds in each case to one row of table A or is specified in table A.1 or A.2

Table 19
Compounds of the formula I in which X is O and Y is S, R is OH, $R^5$ is $CH_3$ and the combination of $R^1$, $R^3$ and if appropriate $R^2$ for a compound corresponds in each case to one row of table A or is specified in table A.1 or A.2

Table 20
Compounds of the formula I in which X is O and Y is S, R is $OCH_2CH=CH_2$, $R^5$ is $CH_3$ and the combination of $R^1$, $R^3$ and if appropriate $R^2$ for a compound corresponds in each case to one row of table A or is specified in table A.1 or A.2

Table 21
Compounds of the formula I in which X is O and Y is S, R is $OCH_2C\equiv CH$, $R^5$ is $CH_3$ and the combination of $R^1$, $R^3$ and if appropriate $R^2$ for a compound corresponds in each case to one row of table A or is specified in table A.1 or A.2

Table 22
Compounds of the formula I in which X is O and Y is S, R is OH, $R^5$ is $CH_2CH_3$ and the combination of $R^1$, $R^3$ and if appropriate $R^2$ for a compound corresponds in each case to one row of table A or is specified in table A.1 or A.2

Table 23
Compounds of the formula I in which X is O and Y is S, R is $OCH_2CH=CH_2$, $R^5$ is $CH_2CH_3$ and the combination of $R^1$, $R^3$ and if appropriate $R^2$ for a compound corresponds in each case to one row of table A or is specified in table A.1 or A.2

Table 24
Compounds of the formula I in which X is O and Y is S, R is $OCH_2C\equiv CH$, $R^5$ is $CH_2CH_3$ and the combination of $R^1$, $R^3$ and if appropriate $R^2$ for a compound corresponds in each case to one row of table A or is specified in table A.1 or A.2

Table 25
Compounds of the formula I in which X is O and Y is S, R is OH, $R^5$ is $OCH_3$ and the combination of $R^1$, $R^3$ and if appropriate $R^2$ for a compound corresponds in each case to one row of table A or is specified in table A.1 or A.2

Table 26
Compounds of the formula I in which X is O and Y is S, R is $OCH_2CH=CH_2$, $R^5$ is $OCH_3$ and the combination of $R^1$, $R^3$ and if appropriate $R^2$ for a compound corresponds in each case to one row of table A or is specified in table A.1 or A.2

Table 27
Compounds of the formula I in which X is O and Y is S, R is $OCH_2C\equiv CH$, $R^5$ is $OCH_3$ and the combination of $R^1$, $R^3$ and if appropriate $R^2$ for a compound corresponds in each case to one row of table A or is specified in table A.1 or A.2

Table 28
Compounds of the formula I in which X is O and Y is S, R is OH, $R^5$ is $SCH_3$ and the combination of $R^1$, $R^3$ and if appropriate $R^2$ for a compound corresponds in each case to one row of table A or is specified in table A.1 or A.2

Table 29
Compounds of the formula I in which X is O and Y is S, R is $OCH_2CH=CH_2$, $R^5$ is $SCH_3$ and the combination of $R^1$, $R^3$ and if appropriate $R^2$ for a compound corresponds in each case to one row of table A or is specified in table A.1 or A.2

Table 30
Compounds of the formula I in which X is O and Y is S, R is $OCH_2C\equiv CH$, $R^5$ is $SCH_3$ and the combination of $R^1$, $R^3$ and if appropriate $R^2$ for a compound corresponds in each case to one row of table A or is specified in table A.1 or A.2

Table 31
Compounds of the formula I in which X is S and Y is O, R is OH, $R^5$ is H and the combination of $R^1$, $R^3$ and if appropriate $R^2$ for a compound corresponds in each case to one row of table A or is specified in table A.1 or A.2

Table 32
Compounds of the formula I in which X is S and Y is O, R is $OCH_2CH=CH_2$, $R^5$ is H and the combination of $R^1$, $R^3$ and if appropriate $R^2$ for a compound corresponds in each case to one row of table A or is specified in table A.1 or A.2

Table 33
Compounds of the formula I in which X is S and Y is O, R is $OCH_2C\equiv CH$, $R^5$ is H and the combination of $R^1$, $R^3$ and if appropriate $R^2$ for a compound corresponds in each case to one row of table A or is specified in table A.1 or A.2

Table 34
Compounds of the formula I in which X is S and Y is O, R is OH, $R^5$ is $CH_3$ and the combination of $R^1$, $R^3$ and if appropriate $R^2$ for a compound corresponds in each case to one row of table A or is specified in table A.1 or A.2

Table 35
Compounds of the formula I in which X is S and Y is O, R is $OCH_2CH=CH_2$, $R^5$ is $CH_3$ and the combination of $R^1$, $R^3$ and if appropriate $R^2$ for a compound corresponds in each case to one row of table A or is specified in table A.1 or A.2

Table 36

Compounds of the formula I in which X is S and Y is O, R is $OCH_2C\equiv CH$, $R^5$ is $CH_3$ and the combination of $R^1$, $R^3$ and if appropriate $R^2$ for a compound corresponds in each case to one row of table A or is specified in table A.1 or A.2

Table 37

Compounds of the formula I in which X is S and Y is O, R is OH, $R^5$ is $CH_2CH_3$ and the combination of $R^1$, $R^3$ and if appropriate $R^2$ for a compound corresponds in each case to one row of table A or is specified in table A.1 or A.2

Table 38

Compounds of the formula I in which X is S and Y is O, R is $OCH_2CH\!=\!CH_2$, $R^5$ is $CH_2CH_3$ and the combination of $R^1$, $R^3$ and if appropriate $R^2$ for a compound corresponds in each case to one row of table A or is specified in table A.1 or A.2

Table 39

Compounds of the formula I in which X is S and Y is O, R is $OCH_2C\equiv CH$, $R^5$ is $CH_2CH_3$ and the combination of $R^1$, $R^3$ and if appropriate. $R^2$ for a compound corresponds in each case to one row of table A or is specified in table A.1 or A.2

Table 40

Compounds of the formula I in which X is S and Y is O, R is OH, $R^5$ is $OCH_3$ and the combination of $R^1$, $R^3$ and if appropriate $R^2$ for a compound corresponds in each case to one row of table A or is specified in table A.1 or A.2

Table 41

Compounds of the formula I in which X is S and Y is O, R is $OCH_2CH\!=\!CH_2$, $R^5$ is $OCH_3$ and the combination of $R^1$, $R^3$ and if appropriate $R^2$ for a compound corresponds in each case to one row of table A or is specified in table A.1 or A.2

Table 42

Compounds of the formula I in which X is S and Y is O, R is $OCH_2C\equiv CH$, $R^5$ is $OCH_3$ and the combination of $R^1$, $R^3$ and if appropriate $R^2$ for a compound corresponds in each case to one row of table A or is specified in table A.1 or A.2

Table 43

Compounds of the formula I in which X is S and Y is O, R is OH, $R^5$ is $SCH_3$ and the combination of $R^1$, $R^3$ and if appropriate $R^2$ for a compound corresponds in each case to one row of table A or is specified in table A.1 or A.2

Table 44

Compounds of the formula I in which X is S and Y is O, R is $OCH_2CH\!=\!CH_2$, $R^5$ is $SCH_3$ and the combination of $R^1$, $R^3$ and if appropriate $R^2$ for a compound corresponds in each case to one row of table A or is specified in table A.1 or A.2

Table 45

Compounds of the formula I in which X is S and Y is O, R is $OCH_2C\equiv CH$, $R^5$ is $SCH_3$ and the combination of $R^1$, $R^3$ and if appropriate $R^2$ for a compound corresponds in each case to one row of table A or is specified in table A.1 or A.2

Table 46

Compounds of the formula I in which X and Y are S, R is OH, $R^5$ is H and the combination of $R^1$, $R^3$ and if appropriate $R^2$ for a compound corresponds in each case to one row of table A or is specified in table A.1 or A.2

Table 47

Compounds of the formula I in which X and Y are S, R is $OCH_2CH\!=\!CH_2$, $R^5$ is H and the combination of $R^1$, $R^3$ and if appropriate $R^2$ for a compound corresponds in each case to one row of table A or is specified in table A.1 or A.2

Table 48

Compounds of the formula I in which X and Y are S, R is $OCH_2C\equiv CH$, $R^5$ is H and the combination of $R^1$, $R^3$ and if appropriate $R^2$ for a compound corresponds in each case to one row of table A or is specified in table A.1 or A.2

Table 49

Compounds of the formula I in which X and Y are S, R is OH, $R^5$ is $CH_3$ and the combination of $R^1$, $R^3$ and if appropriate $R^2$ for a compound corresponds in each case to one row of table A or is specified in table A.1 or A.2

Table 50

Compounds of the formula I in which X and Y are S, R is $OCH_2CH\!=\!CH_2$, $R^5$ is $CH_3$ and the combination of $R^1$, $R^3$ and if appropriate $R^2$ for a compound corresponds in each case to one row of table A or is specified in table A.1 or A.2

Table 51

Compounds of the formula I in which X and Y are S, R is $OCH_2C\equiv CH$, $R^5$ is $CH_3$ and the combination of $R^1$, $R^3$ and if appropriate $R^2$ for a compound corresponds in each case to one row of table A or is specified in table A.1 or A.2

Table 52

Compounds of the formula I in which X and Y are S, R is OH, $R^5$ is $CH_2CH_3$ and the combination of $R^1$, $R^3$ and if appropriate $R^2$ for a compound corresponds in each case to one row of table A or is specified in table A.1 or A.2

Table 53

Compounds of the formula I in which X and Y are S, R is $OCH_2CH\!=\!CH_2$, $R^5$ is $CH_2CH_3$ and the combination of $R^1$, $R^3$ and if appropriate $R^2$ for a compound corresponds in each case to one row of table A or is specified in table A.1 or A.2

Table 54

Compounds of the formula I in which X and Y are S, R is $OCH_2C\equiv CH$, $R^5$ is $CH_2CH_3$ and the combination of $R^1$, $R^3$ and if appropriate $R^2$ for a compound corresponds in each case to one row of table A or is specified in table A.1 or A.2

Table 55

Compounds of the formula I in which X and Y are S, R is OH, $R^5$ is $OCH_3$ and the combination of $R^1$, $R^3$ and if appropriate $R^2$ for a compound corresponds in each case to one row of table A or is specified in table A.1 or A.2

Table 56

Compounds of the formula I in which X and Y are S, R is $OCH_2CH\!=\!CH_2$, $R^5$ is $OCH_3$ and the combination of $R^1$, $R^3$ and if appropriate $R^2$ for a compound corresponds in each case to one row of table A or is specified in table A.1 or A.2

Table 57

Compounds of the formula I in which X and Y are S, R is $OCH_2C\equiv CH$, $R^5$ is $OCH_3$ and the combination of $R^1$, $R^3$ and if appropriate $R^2$ for a compound corresponds in each case to one row of table A or is specified in table A.1 or A.2

Table 58

Compounds of the formula I in which X and Y are S, R is OH, $R^5$ is $SCH_3$ and the combination of $R^1$, $R^3$ and if appropriate $R^2$ for a compound corresponds in each case to one row of table A or is specified in table A.1 or A.2

Table 59

Compounds of the formula I in which X and Y are S, R is $OCH_2CH\!=\!CH_2$, $R^5$ is $SCH_3$ and the combination of $R^1$, $R^3$ and if appropriate $R^2$ for a compound corresponds in each case to one row of table A or is specified in table A.1 or A.2

Table 60

Compounds of the formula I in which X and Y are S, R is $OCH_2C\equiv CH$, $R^5$ is $SCH_3$ and the combination of $R^1$, $R^3$ and if appropriate $R^2$ for a compound corresponds in each case to one row of table A or is specified in table A.1 or A.2

TABLE A
Compounds of the formula I which correspond to the formulae I.1A and I.2A
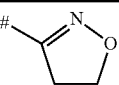
I.1A
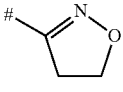
I.2A
| No. | Formula | R¹ | R² | R³ |
|---|---|---|---|---|
| A-1 | I.1A | Cl | 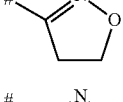 | H |
| A-2 | I.1A | Cl | 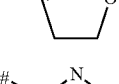 | $CH_3$ |
| A-3 | I.1A | Cl | 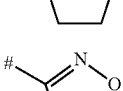 | $CF_3$ |
| A-4 | I.1A | Cl | 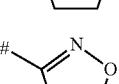 | $CHF_2$ |
| A-5 | I.1A | Cl | 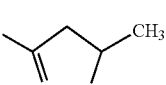 | $OCH_3$ |
| A-6 | I.1A | Cl | 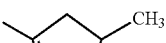 | $OCHF_2$ |
| A-7 | I.1A | Cl | 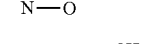 | $SCH_3$ |
| A-8 | I.1A | Cl | 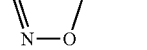 | H |
| A-9 | I.1A | Cl | 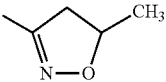 | $CH_3$ |
| A-10 | I.1A | Cl |  | $CF_3$ |
| A-11 | I.1A | Cl |  | $CHF_2$ |

TABLE A-continued
Compounds of the formula I which correspond to the formulae I.1A and I.2A
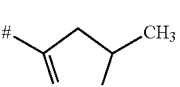
I.1A
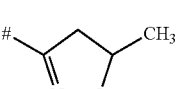
I.2A
| No. | Formula | R¹ | R² | R³ |
|---|---|---|---|---|
| A-12 | I.1A | Cl | 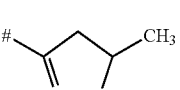 | OCH$_3$ |
| A-13 | I.1A | Cl | 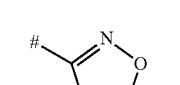 | OCHF$_2$ |
| A-14 | I.1A | Cl | 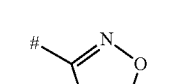 | SCH$_3$ |
| A-15 | I.1A | Cl | 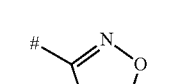 | H |
| A-16 | I.1A | Cl | 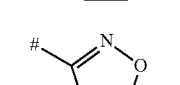 | CH$_3$ |
| A-17 | I.1A | Cl | 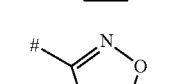 | CF$_3$ |
| A-18 | I.1A | Cl | 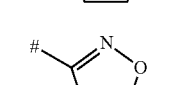 | CHF$_2$ |
| A-19 | I.1A | Cl | 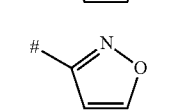 | OCH$_3$ |
| A-20 | I.1A | Cl |  | OCHF$_2$ |
| A-21 | I.1A | Cl |  | SCH$_3$ |

TABLE A-continued

Compounds of the formula I which correspond to the formulae I.1A and I.2A

I.1A

I.2A

| No. | Formula | R¹ | R² | R³ |
|---|---|---|---|---|
| A-22 | I.1A | Cl | 5-methyl-isoxazol-3-yl | H |
| A-23 | I.1A | Cl | 5-methyl-isoxazol-3-yl | $CH_3$ |
| A-24 | I.1A | Cl | 5-methyl-isoxazol-3-yl | $CF_3$ |
| A-25 | I.1A | Cl | 5-methyl-isoxazol-3-yl | $CHF_2$ |
| A-26 | I.1A | Cl | 5-methyl-isoxazol-3-yl | $OCH_3$ |
| A-27 | I.1A | Cl | 5-methyl-isoxazol-3-yl | $OCHF_2$ |
| A-28 | I.1A | Cl | 5-methyl-isoxazol-3-yl | $SCH_3$ |
| A-29 | I.1A | Cl | 3-methyl-4,5-dihydroisoxazol-5-yl | H |
| A-30 | I.1A | Cl | 3-methyl-4,5-dihydroisoxazol-5-yl | $CH_3$ |
| A-31 | I.1A | Cl | 3-methyl-4,5-dihydroisoxazol-5-yl | $CF_3$ |

TABLE A-continued
Compounds of the formula I which correspond to the formulae I.1A and I.2A
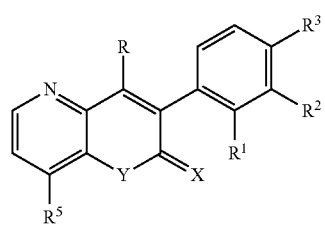
I.1A
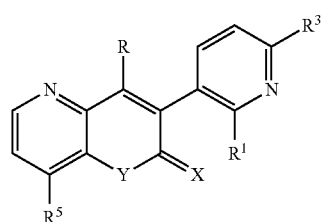
I.2A
| No. | Formula | R¹ | R² | R³ |
|---|---|---|---|---|
| A-32 | I.1A | Cl |  | $CHF_2$ |
| A-33 | I.1A | Cl |  | $OCH_3$ |
| A-34 | I.1A | Cl |  | $OCHF_2$ |
| A-35 | I.1A | Cl |  | $SCH_3$ |
| A-36 | I.1A | Cl | 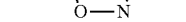 | H |
| A-37 | I.1A | Cl |  | $CH_3$ |
| A-38 | I.1A | Cl |  | $CF_3$ |
| A-39 | I.1A | Cl |  | $CHF_2$ |
| A-40 | I.1A | Cl |  | $OCH_3$ |
| A-41 | I.1A | Cl |  | $OCHF_2$ |

TABLE A-continued

Compounds of the formula I which correspond to the formulae I.1A and I.2A

I.1A

I.2A

| No. | Formula | R¹ | R² | R³ |
|-----|---------|-----|-----|-----|
| A-42 | I.1A | Cl | 3-methyl-isoxazol-5-yl | SCH₃ |
| A-43 | I.1A | Cl | thiazol-2-yl | H |
| A-44 | I.1A | Cl | thiazol-2-yl | CH₃ |
| A-45 | I.1A | Cl | thiazol-2-yl | CF₃ |
| A-46 | I.1A | Cl | thiazol-2-yl | CHF₂ |
| A-47 | I.1A | Cl | thiazol-2-yl | OCH₃ |
| A-48 | I.1A | Cl | thiazol-2-yl | OCHF₂ |
| A-49 | I.1A | Cl | thiazol-2-yl | SCH₃ |
| A-50 | I.1A | Cl | 4-methyl-5-oxo-4,5-dihydro-tetrazol-1-yl | H |

TABLE A-continued
Compounds of the formula I which correspond to the formulae I.1A and I.2A
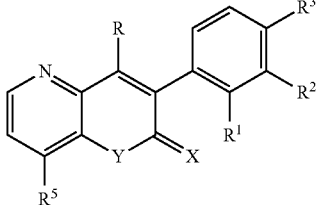
I.1A
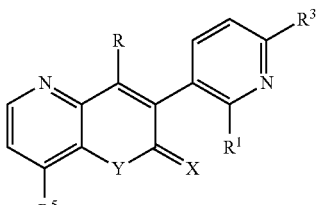
I.2A
| No. | Formula | R¹ | R² | R³ |
|---|---|---|---|---|
| A-51 | I.1A | Cl | 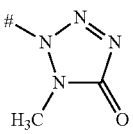 | CH₃ |
| A-52 | I.1A | Cl | 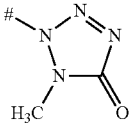 | CF₃ |
| A-53 | I.1A | Cl | 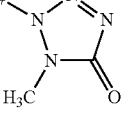 | CHF₂ |
| A-54 | I.1A | Cl | 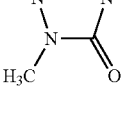 | OCH₃ |
| A-55 | I.1A | Cl | 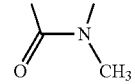 | OCHF₂ |
| A-56 | I.1A | Cl |  | SCH₃ |
| A-57 | I.1A | Cl |  | H |

TABLE A-continued

Compounds of the formula I which correspond to the formulae I.1A and I.2A

I.1A

I.2A

| No. | Formula | $R^1$ | $R^2$ | $R^3$ |
|---|---|---|---|---|
| A-58 | I.1A | Cl | 4-methyl-5-oxo-tetrazol-1-yl | $CH_3$ |
| A-59 | I.1A | Cl | 4-methyl-5-oxo-tetrazol-1-yl | $CF_3$ |
| A-60 | I.1A | Cl | 4-methyl-5-oxo-tetrazol-1-yl | $CHF_2$ |
| A-61 | I.1A | Cl | 4-methyl-5-oxo-tetrazol-1-yl | $OCH_3$ |
| A-62 | I.1A | Cl | 4-methyl-5-oxo-tetrazol-1-yl | $OCHF_2$ |
| A-63 | I.1A | Cl | 4-methyl-5-oxo-tetrazol-1-yl | $SCH_3$ |
| A-64 | I.1A | Cl | morpholin-4-yl | H |
| A-65 | I.1A | Cl | morpholin-4-yl | $CH_3$ |

TABLE A-continued

Compounds of the formula I which correspond to the formulae I.1A and I.2A

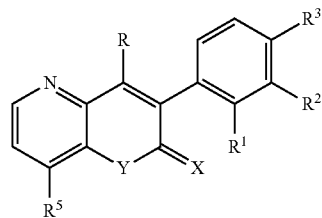
I.1A

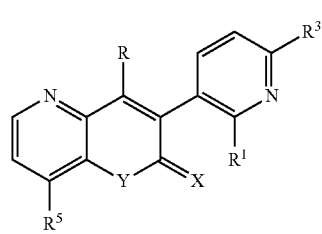
I.2A

| No. | Formula | R¹ | R² | R³ |
|---|---|---|---|---|
| A-66 | I.1A | Cl | # morpholin-N-yl | $CF_3$ |
| A-67 | I.1A | Cl | # morpholin-N-yl | $CHF_2$ |
| A-68 | I.1A | Cl | # morpholin-N-yl | $OCH_3$ |
| A-69 | I.1A | Cl | # morpholin-N-yl | $OCHF_2$ |
| A-70 | I.1A | Cl | # morpholin-N-yl | $SCH_3$ |
| A-71 | I.1A | Cl | $C_6H_5$ | H |
| A-72 | I.1A | Cl | $C_6H_5$ | $CH_3$ |
| A-73 | I.1A | Cl | $C_6H_5$ | $CF_3$ |
| A-74 | I.1A | Cl | $C_6H_5$ | $CHF_2$ |
| A-75 | I.1A | Cl | $C_6H_5$ | $OCH_3$ |
| A-76 | I.1A | Cl | $C_6H_5$ | $OCHF_2$ |
| A-77 | I.1A | Cl | $C_6H_5$ | $SCH_3$ |
| A-78 | I.1A | Cl | 4-F—$C_6H_4$ | H |
| A-79 | I.1A | Cl | 4-F—$C_6H_4$ | $CH_3$ |
| A-80 | I.1A | Cl | 4-F—$C_6H_4$ | $CF_3$ |
| A-81 | I.1A | Cl | 4-F—$C_6H_4$ | $CHF_2$ |
| A-82 | I.1A | Cl | 4-F—$C_6H_4$ | $OCH_3$ |
| A-83 | I.1A | Cl | 4-F—$C_6H_4$ | $OCHF_2$ |
| A-84 | I.1A | Cl | 4-F—$C_6H_4$ | $SCH_3$ |
| A-85 | I.1A | Cl | 4-Cl—$C_6H_4$ | H |
| A-86 | I.1A | Cl | 4-Cl—$C_6H_4$ | $CH_3$ |
| A-87 | I.1A | Cl | 4-Cl—$C_6H_4$ | $CF_3$ |
| A-88 | I.1A | Cl | 4-Cl—$C_6H_4$ | $CHF_2$ |
| A-89 | I.1A | Cl | 4-Cl—$C_6H_4$ | $OCH_3$ |
| A-90 | I.1A | Cl | 4-Cl—$C_6H_4$ | $OCHF_2$ |
| A-91 | I.1A | Cl | 4-Cl—$C_6H_4$ | $SCH_3$ |
| A-92 | I.1A | Cl | 4-$OCH_3$—$C_6H_4$ | H |

TABLE A-continued

Compounds of the formula I which correspond to the formulae I.1A and I.2A

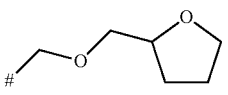

I.1A

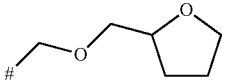

I.2A

| No. | Formula | R¹ | R² | R³ |
|---|---|---|---|---|
| A-93 | I.1A | Cl | 4-OCH$_3$—C$_6$H$_4$ | CH$_3$ |
| A-94 | I.1A | Cl | 4-OCH$_3$—C$_6$H$_4$ | CF$_3$ |
| A-95 | I.1A | Cl | 4-OCH$_3$—C$_6$H$_4$ | CHF$_2$ |
| A-96 | I.1A | Cl | 4-OCH$_3$—C$_6$H$_4$ | OCH$_3$ |
| A-97 | I.1A | Cl | 4-OCH$_3$—C$_6$H$_4$ | OCHF$_2$ |
| A-98 | I.1A | Cl | 4-OCH$_3$—C$_6$H$_4$ | SCH$_3$ |
| A-99 | I.1A | Cl | CH=CH$_2$ | H |
| A-100 | I.1A | Cl | CH=CH$_2$ | CH$_3$ |
| A-101 | I.1A | Cl | CH=CH$_2$ | CF$_3$ |
| A-102 | I.1A | Cl | CH=CH$_2$ | CHF$_2$ |
| A-103 | I.1A | Cl | CH=CH$_2$ | OCH$_3$ |
| A-104 | I.1A | Cl | CH=CH$_2$ | OCHF$_2$ |
| A-105 | I.1A | Cl | CH=CH$_2$ | SCH$_3$ |
| A-106 | I.1A | Cl | CH=CH—CH$_3$ | H |
| A-107 | I.1A | Cl | CH=CH—CH$_3$ | CH$_3$ |
| A-108 | I.1A | Cl | CH=CH—CH$_3$ | CF$_3$ |
| A-109 | I.1A | Cl | CH=CH—CH$_3$ | CHF$_2$ |
| A-110 | I.1A | Cl | CH=CH—CH$_3$ | OCH$_3$ |
| A-111 | I.1A | Cl | CH=CH—CH$_3$ | OCHF$_2$ |
| A-112 | I.1A | Cl | CH=CH—CH$_3$ | SCH$_3$ |
| A-113 | I.1A | Cl | CH$_2$CH=CH$_2$ | H |
| A-114 | I.1A | Cl | CH$_2$CH=CH$_2$ | CH$_3$ |
| A-115 | I.1A | Cl | CH$_2$CH=CH$_2$ | CF$_3$ |
| A-116 | I.1A | Cl | CH$_2$CH=CH$_2$ | CHF$_2$ |
| A-117 | I.1A | Cl | CH$_2$CH=CH$_2$ | OCH$_3$ |
| A-118 | I.1A | Cl | CH$_2$CH=CH$_2$ | OCHF$_2$ |
| A-119 | I.1A | Cl | CH$_2$CH=CH$_2$ | SCH$_3$ |
| A-120 | I.1A | Cl | CH$_2$C≡CH | H |
| A-121 | I.1A | Cl | CH$_2$C≡CH | CH$_3$ |
| A-122 | I.1A | Cl | CH$_2$C≡CH | CF$_3$ |
| A-123 | I.1A | Cl | CH$_2$C≡CH | CHF$_2$ |
| A-124 | I.1A | Cl | CH$_2$C≡CH | OCH$_3$ |
| A-125 | I.1A | Cl | CH$_2$C≡CH | OCHF$_2$ |
| A-126 | I.1A | Cl | CH$_2$C≡CH | SCH$_3$ |
| A-127 | I.1A | Cl | CH$_2$OCH$_2$CF$_3$ | H |
| A-128 | I.1A | Cl | CH$_2$OCH$_2$CF$_3$ | CH$_3$ |
| A-129 | I.1A | Cl | CH$_2$OCH$_2$CF$_3$ | CF$_3$ |
| A-130 | I.1A | Cl | CH$_2$OCH$_2$CF$_3$ | CHF$_2$ |
| A-131 | I.1A | Cl | CH$_2$OCH$_2$CF$_3$ | OCH$_3$ |
| A-132 | I.1A | Cl | CH$_2$OCH$_2$CF$_3$ | OCHF$_2$ |
| A-133 | I.1A | Cl | CH$_2$OCH$_2$CF$_3$ | SCH$_3$ |
| A-134 | I.1A | Cl | (tetrahydrofuranylmethoxymethyl) | H |
| A-135 | I.1A | Cl | (tetrahydrofuranylmethoxymethyl) | CH$_3$ |

TABLE A-continued

Compounds of the formula I which correspond to the formulae I.1A and I.2A

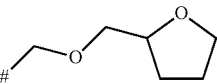
I.1A

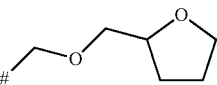
I.2A

| No. | Formula | R¹ | R² | R³ |
|---|---|---|---|---|
| A-136 | I.1A | Cl | 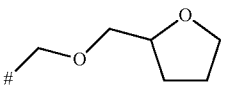 | CF$_3$ |
| A-137 | I.1A | Cl | 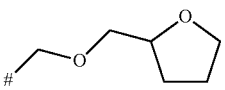 | CHF$_2$ |
| A-138 | I.1A | Cl | 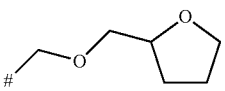 | OCH$_3$ |
| A-139 | I.1A | Cl |  | OCHF$_2$ |
| A-140 | I.1A | Cl |  | SCH$_3$ |
| A-141 | I.1A | Cl | OCH$_2$CH$_3$ | H |
| A-142 | I.1A | Cl | OCH$_2$CH$_3$ | CH$_3$ |
| A-143 | I.1A | Cl | OCH$_2$CH$_3$ | CF$_3$ |
| A-144 | I.1A | Cl | OCH$_2$CH$_3$ | CHF$_2$ |
| A-145 | I.1A | Cl | OCH$_2$CH$_3$ | OCH$_3$ |
| A-146 | I.1A | Cl | OCH$_2$CH$_3$ | OCHF$_2$ |
| A-147 | I.1A | Cl | OCH$_2$CH$_3$ | SCH$_3$ |
| A-148 | I.1A | Cl | OCH$_2$CH$_2$OCH$_3$ | H |
| A-149 | I.1A | Cl | OCH$_2$CH$_2$OCH$_3$ | CH$_3$ |
| A-150 | I.1A | Cl | OCH$_2$CH$_2$OCH$_3$ | CF$_3$ |
| A-151 | I.1A | Cl | OCH$_2$CH$_2$OCH$_3$ | CHF$_2$ |
| A-152 | I.1A | Cl | OCH$_2$CH$_2$OCH$_3$ | OCH$_3$ |
| A-153 | I.1A | Cl | OCH$_2$CH$_2$OCH$_3$ | OCHF$_2$ |
| A-154 | I.1A | Cl | OCH$_2$CH$_2$OCH$_3$ | SCH$_3$ |
| A-155 | I.1A | Cl | SO$_2$CH$_3$ | H |
| A-156 | I.1A | Cl | SO$_2$CH$_3$ | CH$_3$ |
| A-157 | I.1A | Cl | SO$_2$CH$_3$ | CF$_3$ |
| A-158 | I.1A | Cl | SO$_2$CH$_3$ | CHF$_2$ |
| A-159 | I.1A | Cl | SO$_2$CH$_3$ | OCH$_3$ |
| A-160 | I.1A | Cl | SO$_2$CH$_3$ | OCHF$_2$ |
| A-161 | I.1A | Cl | SO$_2$CH$_3$ | SCH$_3$ |
| A-162 | I.1A | Cl | SO$_2$CH$_2$CH$_3$ | H |
| A-163 | I.1A | Cl | SO$_2$CH$_2$CH$_3$ | CH$_3$ |
| A-164 | I.1A | Cl | SO$_2$CH$_2$CH$_3$ | CF$_3$ |
| A-165 | I.1A | Cl | SO$_2$CH$_2$CH$_3$ | CHF$_2$ |

TABLE A-continued

Compounds of the formula I which correspond to the formulae I.1A and I.2A

I.1A

I.2A

| No. | Formula | R$^1$ | R$^2$ | R$^3$ |
|---|---|---|---|---|
| A-166 | I.1A | Cl | SO$_2$CH$_2$CH$_3$ | OCH$_3$ |
| A-167 | I.1A | Cl | SO$_2$CH$_2$CH$_3$ | OCHF$_2$ |
| A-168 | I.1A | Cl | SO$_2$CH$_2$CH$_3$ | SCH$_3$ |
| A-169 | I.1A | Cl | SO$_2$CH(CH$_3$)$_2$ | H |
| A-170 | I.1A | Cl | SO$_2$CH(CH$_3$)$_2$ | CH$_3$ |
| A-171 | I.1A | Cl | SO$_2$CH(CH$_3$)$_2$ | CF$_3$ |
| A-172 | I.1A | Cl | SO$_2$CH(CH$_3$)$_2$ | CHF$_2$ |
| A-173 | I.1A | Cl | SO$_2$CH(CH$_3$)$_2$ | OCH$_3$ |
| A-174 | I.1A | Cl | SO$_2$CH(CH$_3$)$_2$ | OCHF$_2$ |
| A-175 | I.1A | Cl | SO$_2$CH(CH$_3$)$_2$ | SCH$_3$ |
| A-176 | I.1A | Cl | COOCH$_3$ | H |
| A-177 | I.1A | Cl | COOCH$_3$ | CH$_3$ |
| A-178 | I.1A | Cl | COOCH$_3$ | CF$_3$ |
| A-179 | I.1A | Cl | COOCH$_3$ | CHF$_2$ |
| A-180 | I.1A | Cl | COOCH$_3$ | OCH$_3$ |
| A-181 | I.1A | Cl | COOCH$_3$ | OCHF$_2$ |
| A-182 | I.1A | Cl | COOCH$_3$ | SCH$_3$ |
| A-183 | I.1A | Cl | COOCH$_2$CH$_3$ | H |
| A-184 | I.1A | Cl | COOCH$_2$CH$_3$ | CH$_3$ |
| A-185 | I.1A | Cl | COOCH$_2$CH$_3$ | CF$_3$ |
| A-186 | I.1A | Cl | COOCH$_2$CH$_3$ | CHF$_2$ |
| A-187 | I.1A | Cl | COOCH$_2$CH$_3$ | OCH$_3$ |
| A-188 | I.1A | Cl | COOCH$_2$CH$_3$ | OCHF$_2$ |
| A-189 | I.1A | Cl | COOCH$_2$CH$_3$ | SCH$_3$ |
| A-190 | I.1A | Cl | #$^2$—CH$_2$CH$_2$SO$_2$—#$^3$ | |
| A-191 | I.1A | Cl | #$^2$—CH(CH$_3$)CH$_2$SO$_2$—#$^3$ | |
| A-192 | I.1A | Cl | #$^2$—C(CH$_3$)$_2$CH$_2$SO$_2$—#$^3$ | |
| A-193 | I.1A | Cl | #$^2$—SO$_2$CH$_2$CH$_2$SO$_2$—#$^3$ | |
| A-194 | I.1A | Cl | #$^2$—CH(OCH$_2$CH$_2$F)CH$_2$CH$_2$SO$_2$—#$^3$ | |
| A-195 | I.1A | Cl | #$^2$—C(=NOCH$_3$)CH$_2$CH$_2$SO$_2$—#$^3$ | |
| A-196 | I.1A | Cl | #$^2$—SO$_2$CH$_2$CH$_2$C(CH$_3$)$_2$—#$^3$ | |
| A-197 | I.1A | Cl | #$^2$—N(CH$_3$)C(=O)S—#$^3$ | |
| A-198 | I.1A | Cl | #$^2$—C(=O)N(CH$_3$)SO$_2$—#$^3$ | |
| A-199 | I.1A | Br | (4,5-dihydroisoxazol-3-yl) | H |
| A-200 | I.1A | Br | (4,5-dihydroisoxazol-3-yl) | CH$_3$ |
| A-201 | I.1A | Br | (4,5-dihydroisoxazol-3-yl) | CF$_3$ |

TABLE A-continued
Compounds of the formula I which correspond to the formulae I.1A and I.2A
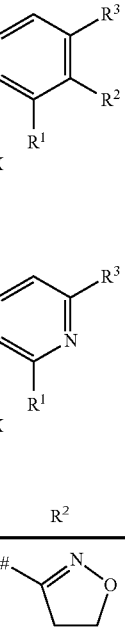
I.1A
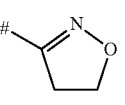
I.2A
| No. | Formula | R¹ | R² | R³ |
|---|---|---|---|---|
| A-202 | I.1A | Br | 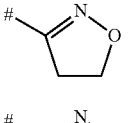 | CHF$_2$ |
| A-203 | I.1A | Br | 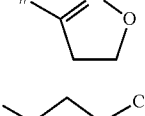 | OCH$_3$ |
| A-204 | I.1A | Br | 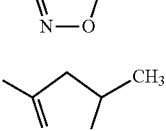 | OCHF$_2$ |
| A-205 | I.1A | Br | 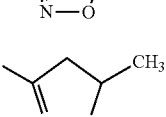 | SCH$_3$ |
| A-206 | I.1A | Br | 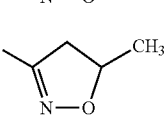 | H |
| A-207 | I.1A | Br | 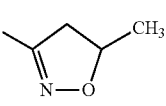 | CH$_3$ |
| A-208 | I.1A | Br | 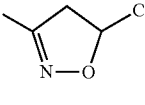 | CF$_3$ |
| A-209 | I.1A | Br |  | CHF$_2$ |
| A-210 | I.1A | Br |  | OCH$_3$ |
| A-211 | I.1A | Br |  | OCHF$_2$ |

TABLE A-continued

Compounds of the formula I which correspond to the formulae I.1A and I.2A

I.1A

I.2A

| No. | Formula | $R^1$ | $R^2$ | $R^3$ |
|---|---|---|---|---|
| A-212 | I.1A | Br | # — isoxazoline-5-CH$_3$ | SCH$_3$ |
| A-213 | I.1A | Br | # — isoxazole | H |
| A-214 | I.1A | Br | # — isoxazole | CH$_3$ |
| A-215 | I.1A | Br | # — isoxazole | CF$_3$ |
| A-216 | I.1A | Br | # — isoxazole | CHF$_2$ |
| A-217 | I.1A | Br | # — isoxazole | OCH$_3$ |
| A-218 | I.1A | Br | # — isoxazole | OCHF$_2$ |
| A-219 | I.1A | Br | # — isoxazole | SCH$_3$ |
| A-220 | I.1A | Br | # — 5-CH$_3$-isoxazole | H |
| A-221 | I.1A | Br | # — 5-CH$_3$-isoxazole | CH$_3$ |
| A-222 | I.1A | Br | # — 5-CH$_3$-isoxazole | CF$_3$ |

TABLE A-continued

Compounds of the formula I which correspond to the formulae I.1A and I.2A

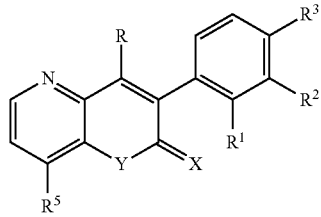
I.1A

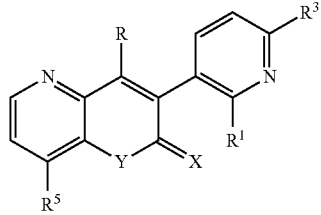
I.2A

| No. | Formula | R¹ | R² | R³ |
|---|---|---|---|---|
| A-223 | I.1A | Br | # 3-methyl-5-methylisoxazole | $CHF_2$ |
| A-224 | I.1A | Br | # 3-methyl-5-methylisoxazole | $OCH_3$ |
| A-225 | I.1A | Br | # 3-methyl-5-methylisoxazole | $OCHF_2$ |
| A-226 | I.1A | Br | # 3-methyl-5-methylisoxazole | $SCH_3$ |
| A-227 | I.1A | Br | # methylisoxazoline | H |
| A-228 | I.1A | Br | # methylisoxazoline | $CH_3$ |
| A-229 | I.1A | Br | # methylisoxazoline | $CF_3$ |
| A-230 | I.1A | Br | # methylisoxazoline | $CHF_2$ |
| A-231 | I.1A | Br | # methylisoxazoline | $OCH_3$ |
| A-232 | I.1A | Br | # methylisoxazoline | $OCHF_2$ |

TABLE A-continued

Compounds of the formula I which correspond to the formulae I.1A and I.2A

I.1A

I.2A

| No. | Formula | R¹ | R² | R³ |
|---|---|---|---|---|
| A-233 | I.1A | Br | 5-(3-methylisoxazolyl) | SCH$_3$ |
| A-234 | I.1A | Br | 5-(3-methylisoxazolyl) | H |
| A-235 | I.1A | Br | 5-(3-methylisoxazolyl) | CH$_3$ |
| A-236 | I.1A | Br | 5-(3-methylisoxazolyl) | CF$_3$ |
| A-237 | I.1A | Br | 5-(3-methylisoxazolyl) | CHF$_2$ |
| A-238 | I.1A | Br | 5-(3-methylisoxazolyl) | OCH$_3$ |
| A-239 | I.1A | Br | 5-(3-methylisoxazolyl) | OCHF$_2$ |
| A-240 | I.1A | Br | 5-(3-methylisoxazolyl) | SCH$_3$ |
| A-241 | I.1A | Br | 2-thiazolyl | H |
| A-242 | I.1A | Br | 2-thiazolyl | CH$_3$ |

TABLE A-continued

Compounds of the formula I which correspond to the formulae I.1A and I.2A

I.1A

I.2A

| No. | Formula | R¹ | R² | R³ |
|-----|---------|-----|-----|-----|
| A-243 | I.1A | Br | thiazol-2-yl | CF$_3$ |
| A-244 | I.1A | Br | thiazol-2-yl | CHF$_2$ |
| A-245 | I.1A | Br | thiazol-2-yl | OCH$_3$ |
| A-246 | I.1A | Br | thiazol-2-yl | OCHF$_2$ |
| A-247 | I.1A | Br | thiazol-2-yl | SCH$_3$ |
| A-248 | I.1A | Br | 4-methyl-5-oxo-tetrazol-1-yl | H |
| A-249 | I.1A | Br | 4-methyl-5-oxo-tetrazol-1-yl | CH$_3$ |
| A-250 | I.1A | Br | 4-methyl-5-oxo-tetrazol-1-yl | CF$_3$ |

TABLE A-continued

Compounds of the formula I which correspond to the formulae I.1A and I.2A

I.1A

[Structure I.1A: pyridine fused ring system with substituents R, R$^1$, R$^2$, R$^3$, R$^5$, X, Y]

I.2A

[Structure I.2A: pyridine fused ring system with pyridyl substituent bearing R$^1$, R$^3$ and R, R$^5$, X, Y]

| No. | Formula | R$^1$ | R$^2$ | R$^3$ |
|---|---|---|---|---|
| A-251 | I.1A | Br | N-methyl-tetrazolinone (attached via N) | CHF$_2$ |
| A-252 | I.1A | Br | N-methyl-tetrazolinone (attached via N) | OCH$_3$ |
| A-253 | I.1A | Br | N-methyl-tetrazolinone (attached via N) | OCHF$_2$ |
| A-254 | I.1A | Br | N-methyl-tetrazolinone (attached via N) | SCH$_3$ |
| A-255 | I.1A | Br | N-methyl-tetrazolinone (attached via N) | H |
| A-256 | I.1A | Br | N-methyl-tetrazolinone (attached via N) | CH$_3$ |
| A-257 | I.1A | Br | N-methyl-tetrazolinone (attached via N) | CF$_3$ |

TABLE A-continued
Compounds of the formula I which correspond to the formulae I.1A and I.2A
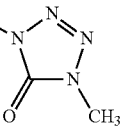
I.1A
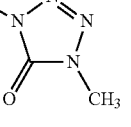
I.2A
| No. | Formula | R¹ | R² | R³ |
|---|---|---|---|---|
| A-258 | I.1A | Br | 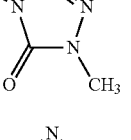 | CHF$_2$ |
| A-259 | I.1A | Br | 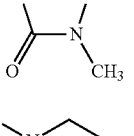 | OCH$_3$ |
| A-260 | I.1A | Br | 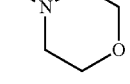 | OCHF$_2$ |
| A-261 | I.1A | Br | 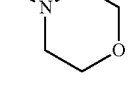 | SCH$_3$ |
| A-262 | I.1A | Br | 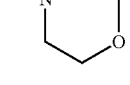 | H |
| A-263 | I.1A | Br | 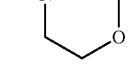 | CH$_3$ |
| A-264 | I.1A | Br | 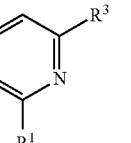 | CF$_3$ |
| A-265 | I.1A | Br |  | CHF$_2$ |

TABLE A-continued

Compounds of the formula I which correspond to the formulae I.1A and I.2A

I.1A

I.2A

| No. | Formula | R¹ | R² | R³ |
|---|---|---|---|---|
| A-266 | I.1A | Br | # -morpholino | $OCH_3$ |
| A-267 | I.1A | Br | # -morpholino | $OCHF_2$ |
| A-268 | I.1A | Br | # -morpholino | $SCH_3$ |
| A-269 | I.1A | Br | $C_6H_5$ | H |
| A-270 | I.1A | Br | $C_6H_5$ | $CH_3$ |
| A-271 | I.1A | Br | $C_6H_5$ | $CF_3$ |
| A-272 | I.1A | Br | $C_6H_5$ | $CHF_2$ |
| A-273 | I.1A | Br | $C_6H_5$ | $OCH_3$ |
| A-274 | I.1A | Br | $C_6H_5$ | $OCHF_2$ |
| A-275 | I.1A | Br | $C_6H_5$ | $SCH_3$ |
| A-276 | I.1A | Br | 4-F—$C_6H_4$ | H |
| A-277 | I.1A | Br | 4-F—$C_6H_4$ | $CH_3$ |
| A-278 | I.1A | Br | 4-F—$C_6H_4$ | $CF_3$ |
| A-279 | I.1A | Br | 4-F—$C_6H_4$ | $CHF_2$ |
| A-280 | I.1A | Br | 4-F—$C_6H_4$ | $OCH_3$ |
| A-281 | I.1A | Br | 4-F—$C_6H_4$ | $OCHF_2$ |
| A-282 | I.1A | Br | 4-F—$C_6H_4$ | $SCH_3$ |
| A-283 | I.1A | Br | 4-Cl—$C_6H_4$ | H |
| A-284 | I.1A | Br | 4-Cl—$C_6H_4$ | $CH_3$ |
| A-285 | I.1A | Br | 4-Cl—$C_6H_4$ | $CF_3$ |
| A-286 | I.1A | Br | 4-Cl—$C_6H_4$ | $CHF_2$ |
| A-287 | I.1A | Br | 4-Cl—$C_6H_4$ | $OCH_3$ |
| A-288 | I.1A | Br | 4-Cl—$C_6H_4$ | $OCHF_2$ |
| A-289 | I.1A | Br | 4-Cl—$C_6H_4$ | $SCH_3$ |
| A-290 | I.1A | Br | 4-$OCH_3$—$C_6H_4$ | H |
| A-291 | I.1A | Br | 4-$OCH_3$—$C_6H_4$ | $CH_3$ |
| A-292 | I.1A | Br | 4-$OCH_3$—$C_6H_4$ | $CF_3$ |
| A-293 | I.1A | Br | 4-$OCH_3$—$C_6H_4$ | $CHF_2$ |
| A-294 | I.1A | Br | 4-$OCH_3$—$C_6H_4$ | $OCH_3$ |
| A-295 | I.1A | Br | 4-$OCH_3$—$C_6H_4$ | $OCHF_2$ |
| A-296 | I.1A | Br | 4-$OCH_3$—$C_6H_4$ | $SCH_3$ |
| A-297 | I.1A | Br | $CH=CH_2$ | H |
| A-298 | I.1A | Br | $CH=CH_2$ | $CH_3$ |
| A-299 | I.1A | Br | $CH=CH_2$ | $CF_3$ |
| A-300 | I.1A | Br | $CH=CH_2$ | $CHF_2$ |
| A-301 | I.1A | Br | $CH=CH_2$ | $OCH_3$ |
| A-302 | I.1A | Br | $CH=CH_2$ | $OCHF_2$ |
| A-303 | I.1A | Br | $CH=CH_2$ | $SCH_3$ |

TABLE A-continued

Compounds of the formula I which correspond to the formulae I.1A and I.2A

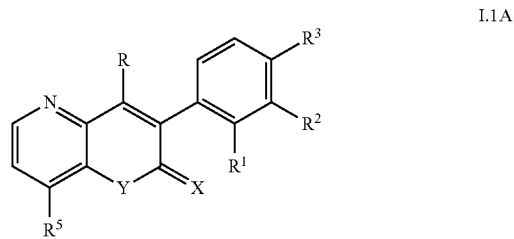
I.1A

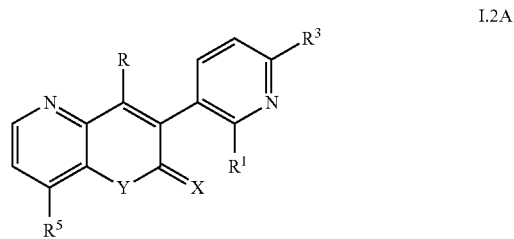
I.2A

| No. | Formula | R¹ | R² | R³ |
|---|---|---|---|---|
| A-304 | I.1A | Br | CH=CH—CH$_3$ | H |
| A-305 | I.1A | Br | CH=CH—CH$_3$ | CH$_3$ |
| A-306 | I.1A | Br | CH=CH—CH$_3$ | CF$_3$ |
| A-307 | I.1A | Br | CH=CH—CH$_3$ | CHF$_2$ |
| A-308 | I.1A | Br | CH=CH—CH$_3$ | OCH$_3$ |
| A-309 | I.1A | Br | CH=CH—CH$_3$ | OCHF$_2$ |
| A-310 | I.1A | Br | CH=CH—CH$_3$ | SCH$_3$ |
| A-311 | I.1A | Br | CH$_2$CH=CH$_2$ | H |
| A-312 | I.1A | Br | CH$_2$CH=CH$_2$ | CH$_3$ |
| A-313 | I.1A | Br | CH$_2$CH=CH$_2$ | CF$_3$ |
| A-314 | I.1A | Br | CH$_2$CH=CH$_2$ | CHF$_2$ |
| A-315 | I.1A | Br | CH$_2$CH=CH$_2$ | OCH$_3$ |
| A-316 | I.1A | Br | CH$_2$CH=CH$_2$ | OCHF$_2$ |
| A-317 | I.1A | Br | CH$_2$CH=CH$_2$ | SCH$_3$ |
| A-318 | I.1A | Br | CH$_2$C≡CH | H |
| A-319 | I.1A | Br | CH$_2$C≡CH | CH$_3$ |
| A-320 | I.1A | Br | CH$_2$C≡CH | CF$_3$ |
| A-321 | I.1A | Br | CH$_2$C≡CH | CHF$_2$ |
| A-322 | I.1A | Br | CH$_2$C≡CH | OCH$_3$ |
| A-323 | I.1A | Br | CH$_2$C≡CH | OCHF$_2$ |
| A-324 | I.1A | Br | CH$_2$C≡CH | SCH$_3$ |
| A-325 | I.1A | Br | CH$_2$OCH$_2$CF$_3$ | H |
| A-326 | I.1A | Br | CH$_2$OCH$_2$CF$_3$ | CH$_3$ |
| A-327 | I.1A | Br | CH$_2$OCH$_2$CF$_3$ | CF$_3$ |
| A-328 | I.1A | Br | CH$_2$OCH$_2$CF$_3$ | CHF$_2$ |
| A-329 | I.1A | Br | CH$_2$OCH$_2$CF$_3$ | OCH$_3$ |
| A-330 | I.1A | Br | CH$_2$OCH$_2$CF$_3$ | OCHF$_2$ |
| A-331 | I.1A | Br | CH$_2$OCH$_2$CF$_3$ | SCH$_3$ |
| A-332 | I.1A | Br | 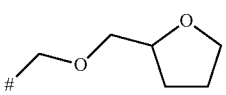 | H |
| A-333 | I.1A | Br | 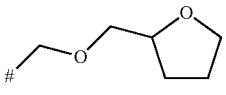 | CH$_3$ |
| A-334 | I.1A | Br | 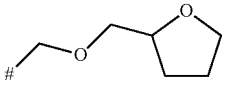 | CF$_3$ |
| A-335 | I.1A | Br | 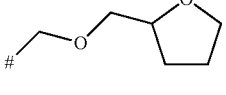 | CHF$_2$ |

TABLE A-continued

Compounds of the formula I which correspond to the formulae I.1A and I.2A

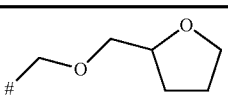

I.1A

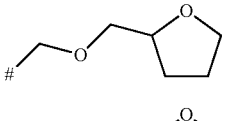

I.2A

| No. | Formula | R¹ | R² | R³ |
|---|---|---|---|---|
| A-336 | I.1A | Br | 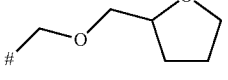 | OCH$_3$ |
| A-337 | I.1A | Br | (same as above) | OCHF$_2$ |
| A-338 | I.1A | Br | (same as above) | SCH$_3$ |
| A-339 | I.1A | Br | OCH$_2$CH$_3$ | H |
| A-340 | I.1A | Br | OCH$_2$CH$_3$ | CH$_3$ |
| A-341 | I.1A | Br | OCH$_2$CH$_3$ | CF$_3$ |
| A-342 | I.1A | Br | OCH$_2$CH$_3$ | CHF$_2$ |
| A-343 | I.1A | Br | OCH$_2$CH$_3$ | OCH$_3$ |
| A-344 | I.1A | Br | OCH$_2$CH$_3$ | OCHF$_2$ |
| A-345 | I.1A | Br | OCH$_2$CH$_3$ | SCH$_3$ |
| A-346 | I.1A | Br | OCH$_2$CH$_2$OCH$_3$ | H |
| A-347 | I.1A | Br | OCH$_2$CH$_2$OCH$_3$ | CH$_3$ |
| A-348 | I.1A | Br | OCH$_2$CH$_2$OCH$_3$ | CF$_3$ |
| A-349 | I.1A | Br | OCH$_2$CH$_2$OCH$_3$ | CHF$_2$ |
| A-350 | I.1A | Br | OCH$_2$CH$_2$OCH$_3$ | OCH$_3$ |
| A-351 | I.1A | Br | OCH$_2$CH$_2$OCH$_3$ | OCHF$_2$ |
| A-352 | I.1A | Br | OCH$_2$CH$_2$OCH$_3$ | SCH$_3$ |
| A-353 | I.1A | Br | SO$_2$CH$_3$ | H |
| A-354 | I.1A | Br | SO$_2$CH$_3$ | CH$_3$ |
| A-355 | I.1A | Br | SO$_2$CH$_3$ | CF$_3$ |
| A-356 | I.1A | Br | SO$_2$CH$_3$ | CHF$_2$ |
| A-357 | I.1A | Br | SO$_2$CH$_3$ | OCH$_3$ |
| A-358 | I.1A | Br | SO$_2$CH$_3$ | OCHF$_2$ |
| A-359 | I.1A | Br | SO$_2$CH$_3$ | SCH$_3$ |
| A-360 | I.1A | Br | SO$_2$CH$_2$CH$_3$ | H |
| A-361 | I.1A | Br | SO$_2$CH$_2$CH$_3$ | CH$_3$ |
| A-362 | I.1A | Br | SO$_2$CH$_2$CH$_3$ | CF$_3$ |
| A-363 | I.1A | Br | SO$_2$CH$_2$CH$_3$ | CHF$_2$ |
| A-364 | I.1A | Br | SO$_2$CH$_2$CH$_3$ | OCH$_3$ |
| A-365 | I.1A | Br | SO$_2$CH$_2$CH$_3$ | OCHF$_2$ |
| A-366 | I.1A | Br | SO$_2$CH$_2$CH$_3$ | SCH$_3$ |
| A-367 | I.1A | Br | SO$_2$CH(CH$_3$)$_2$ | H |
| A-368 | I.1A | Br | SO$_2$CH(CH$_3$)$_2$ | CH$_3$ |
| A-369 | I.1A | Br | SO$_2$CH(CH$_3$)$_2$ | CF$_3$ |
| A-370 | I.1A | Br | SO$_2$CH(CH$_3$)$_2$ | CHF$_2$ |
| A-371 | I.1A | Br | SO$_2$CH(CH$_3$)$_2$ | OCH$_3$ |
| A-372 | I.1A | Br | SO$_2$CH(CH$_3$)$_2$ | OCHF$_2$ |
| A-373 | I.1A | Br | SO$_2$CH(CH$_3$)$_2$ | SCH$_3$ |
| A-374 | I.1A | Br | COOCH$_3$ | H |
| A-375 | I.1A | Br | COOCH$_3$ | CH$_3$ |

TABLE A-continued

Compounds of the formula I which correspond to the formulae I.1A and I.2A

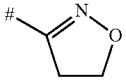

I.1A

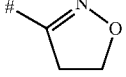

I.2A

| No. | Formula | R¹ | R² | R³ |
|---|---|---|---|---|
| A-376 | I.1A | Br | COOCH$_3$ | CF$_3$ |
| A-377 | I.1A | Br | COOCH$_3$ | CHF$_2$ |
| A-378 | I.1A | Br | COOCH$_3$ | OCH$_3$ |
| A-379 | I.1A | Br | COOCH$_3$ | OCHF$_2$ |
| A-380 | I.1A | Br | COOCH$_3$ | SCH$_3$ |
| A-381 | I.1A | Br | COOCH$_2$CH$_3$ | H |
| A-382 | I.1A | Br | COOCH$_2$CH$_3$ | CH$_3$ |
| A-383 | I.1A | Br | COOCH$_2$CH$_3$ | CF$_3$ |
| A-384 | I.1A | Br | COOCH$_2$CH$_3$ | CHF$_2$ |
| A-385 | I.1A | Br | COOCH$_2$CH$_3$ | OCH$_3$ |
| A-386 | I.1A | Br | COOCH$_2$CH$_3$ | OCHF$_2$ |
| A-387 | I.1A | Br | COOCH$_2$CH$_3$ | SCH$_3$ |
| A-388 | I.1A | Br | #²—CH$_2$CH$_2$SO$_2$—#³ | |
| A-389 | I.1A | Br | #²—CH(CH$_3$)CH$_2$SO$_2$—#³ | |
| A-390 | I.1A | Br | #²—C(CH$_3$)$_2$CH$_2$SO$_2$—#³ | |
| A-391 | I.1A | Br | #²—SO$_2$CH$_2$CH$_2$SO$_2$—#³ | |
| A-392 | I.1A | Br | #²—CH(OCH$_2$CH$_2$F)CH$_2$CH$_2$SO$_2$—#³ | |
| A-393 | I.1A | Br | #²—C(=NOCH$_3$)CH$_2$CH$_2$SO$_2$—#³ | |
| A-394 | I.1A | Br | #²—SO$_2$CH$_2$CH$_2$C(CH$_3$)$_2$—#³ | |
| A-395 | I.1A | Br | #²—N(CH$_3$)C(=O)S—#³ | |
| A-396 | I.1A | Br | #²—C(=O)N(CH$_3$)SO$_2$—#³ | |
| A-397 | I.1A | CH$_3$ | 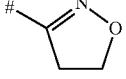 | H |
| A-398 | I.1A | CH$_3$ | 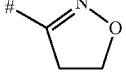 | CH$_3$ |
| A-399 | I.1A | CH$_3$ | 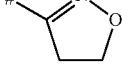 | CF$_3$ |
| A-400 | I.1A | CH$_3$ | 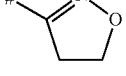 | CHF$_2$ |
| A-401 | I.1A | CH$_3$ | 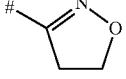 | OCH$_3$ |
| A-402 | I.1A | CH$_3$ | 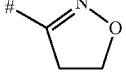 | OCHF$_2$ |

TABLE A-continued

Compounds of the formula I which correspond to the formulae I.1A and I.2A

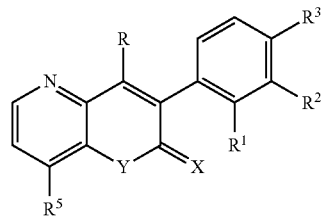

I.1A

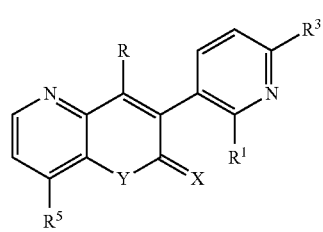

I.2A

| No. | Formula | R¹ | R² | R³ |
|---|---|---|---|---|
| A-403 | I.1A | CH$_3$ | #—isoxazoline | SCH$_3$ |
| A-404 | I.1A | CH$_3$ | #—5-methyl-isoxazoline | H |
| A-405 | I.1A | CH$_3$ | #—5-methyl-isoxazoline | CH$_3$ |
| A-406 | I.1A | CH$_3$ | #—5-methyl-isoxazoline | CF$_3$ |
| A-407 | I.1A | CH$_3$ | #—5-methyl-isoxazoline | CHF$_2$ |
| A-408 | I.1A | CH$_3$ | #—5-methyl-isoxazoline | OCH$_3$ |
| A-409 | I.1A | CH$_3$ | #—5-methyl-isoxazoline | OCHF$_2$ |
| A-410 | I.1A | CH$_3$ | #—5-methyl-isoxazoline | SCH$_3$ |
| A-411 | I.1A | CH$_3$ | #—isoxazole | H |
| A-412 | I.1A | CH$_3$ | #—isoxazole | CH$_3$ |

TABLE A-continued

Compounds of the formula I which correspond to the formulae I.1A and I.2A

I.1A

I.2A

| No. | Formula | R¹ | R² | R³ |
|---|---|---|---|---|
| A-413 | I.1A | CH₃ | #-isoxazol-3-yl | CF₃ |
| A-414 | I.1A | CH₃ | #-isoxazol-3-yl | CHF₂ |
| A-415 | I.1A | CH₃ | #-isoxazol-3-yl | OCH₃ |
| A-416 | I.1A | CH₃ | #-isoxazol-3-yl | OCHF₂ |
| A-417 | I.1A | CH₃ | #-isoxazol-3-yl | SCH₃ |
| A-418 | I.1A | CH₃ | #-5-methylisoxazol-3-yl | H |
| A-419 | I.1A | CH₃ | #-5-methylisoxazol-3-yl | CH₃ |
| A-420 | I.1A | CH₃ | #-5-methylisoxazol-3-yl | CF₃ |
| A-421 | I.1A | CH₃ | #-5-methylisoxazol-3-yl | CHF₂ |
| A-422 | I.1A | CH₃ | #-5-methylisoxazol-3-yl | OCH₃ |

TABLE A-continued

Compounds of the formula I which correspond to the formulae I.1A and I.2A

I.1A

I.2A

| No. | Formula | R¹ | R² | R³ |
|---|---|---|---|---|
| A-423 | I.1A | CH₃ | #-(5-methyl-isoxazol-3-yl) | OCHF₂ |
| A-424 | I.1A | CH₃ | #-(5-methyl-isoxazol-3-yl) | SCH₃ |
| A-425 | I.1A | CH₃ | #-(3-methyl-4,5-dihydroisoxazol-5-yl) | H |
| A-426 | I.1A | CH₃ | #-(3-methyl-4,5-dihydroisoxazol-5-yl) | CH₃ |
| A-427 | I.1A | CH₃ | #-(3-methyl-4,5-dihydroisoxazol-5-yl) | CF₃ |
| A-428 | I.1A | CH₃ | #-(3-methyl-4,5-dihydroisoxazol-5-yl) | CHF₂ |
| A-429 | I.1A | CH₃ | #-(3-methyl-4,5-dihydroisoxazol-5-yl) | OCH₃ |
| A-430 | I.1A | CH₃ | #-(3-methyl-4,5-dihydroisoxazol-5-yl) | OCHF₂ |
| A-431 | I.1A | CH₃ | #-(3-methyl-4,5-dihydroisoxazol-5-yl) | SCH₃ |
| A-432 | I.1A | CH₃ | #-(3-methyl-isoxazol-5-yl) | H |

TABLE A-continued

Compounds of the formula I which correspond to the formulae I.1A and I.2A

I.1A

I.2A

| No. | Formula | R¹ | R² | R³ |
|---|---|---|---|---|
| A-433 | I.1A | CH₃ | 3-methylisoxazol-5-yl | CH₃ |
| A-434 | I.1A | CH₃ | 3-methylisoxazol-5-yl | CF₃ |
| A-435 | I.1A | CH₃ | 3-methylisoxazol-5-yl | CHF₂ |
| A-436 | I.1A | CH₃ | 3-methylisoxazol-5-yl | OCH₃ |
| A-437 | I.1A | CH₃ | 3-methylisoxazol-5-yl | OCHF₂ |
| A-438 | I.1A | CH₃ | 3-methylisoxazol-5-yl | SCH₃ |
| A-439 | I.1A | CH₃ | thiazol-2-yl | H |
| A-440 | I.1A | CH₃ | thiazol-2-yl | CH₃ |
| A-441 | I.1A | CH₃ | thiazol-2-yl | CF₃ |
| A-442 | I.1A | CH₃ | thiazol-2-yl | CHF₂ |

TABLE A-continued

Compounds of the formula I which correspond to the formulae I.1A and I.2A

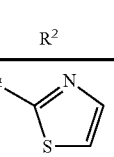

I.1A

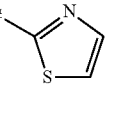

I.2A

| No. | Formula | R¹ | R² | R³ |
|---|---|---|---|---|
| A-443 | I.1A | CH$_3$ | 2-thiazolyl | OCH$_3$ |
| A-444 | I.1A | CH$_3$ | 2-thiazolyl | OCHF$_2$ |
| A-445 | I.1A | CH$_3$ | 2-thiazolyl | SCH$_3$ |
| A-446 | I.1A | CH$_3$ | 1-methyl-5-oxo-tetrazol-2-yl | H |
| A-447 | I.1A | CH$_3$ | 1-methyl-5-oxo-tetrazol-2-yl | CH$_3$ |
| A-448 | I.1A | CH$_3$ | 1-methyl-5-oxo-tetrazol-2-yl | CF$_3$ |
| A-449 | I.1A | CH$_3$ | 1-methyl-5-oxo-tetrazol-2-yl | CHF$_2$ |
| A-450 | I.1A | CH$_3$ | 1-methyl-5-oxo-tetrazol-2-yl | OCH$_3$ |

TABLE A-continued
Compounds of the formula I which correspond to the formulae I.1A and I.2A
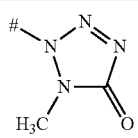
I.1A
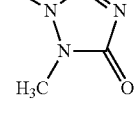
I.2A
| No. | Formula | R¹ | R² | R³ |
|---|---|---|---|---|
| A-451 | I.1A | $CH_3$ | 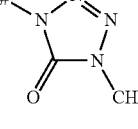 | $OCHF_2$ |
| A-452 | I.1A | $CH_3$ | 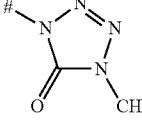 | $SCH_3$ |
| A-453 | I.1A | $CH_3$ | 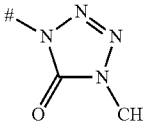 | H |
| A-454 | I.1A | $CH_3$ | 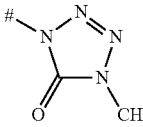 | $CH_3$ |
| A-455 | I.1A | $CH_3$ | 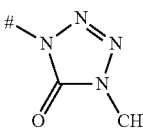 | $CF_3$ |
| A-456 | I.1A | $CH_3$ | | $CHF_2$ |
| A-457 | I.1A | $CH_3$ | | $OCH_3$ |

TABLE A-continued
Compounds of the formula I which correspond to the formulae I.1A and I.2A
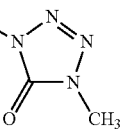
I.1A
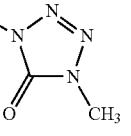
I.2A
| No. | Formula | R¹ | R² | R³ |
|---|---|---|---|---|
| A-458 | I.1A | CH₃ | 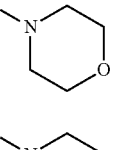 | OCHF₂ |
| A-459 | I.1A | CH₃ | 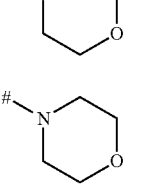 | SCH₃ |
| A-460 | I.1A | CH₃ |  | H |
| A-461 | I.1A | CH₃ | 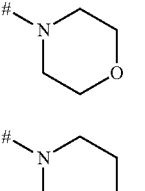 | CH₃ |
| A-462 | I.1A | CH₃ | 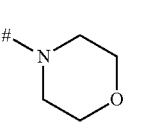 | CF₃ |
| A-463 | I.1A | CH₃ |  | CHF₂ |
| A-464 | I.1A | CH₃ |  | OCH₃ |
| A-465 | I.1A | CH₃ |  | OCHF₂ |

TABLE A-continued

Compounds of the formula I which correspond to the formulae I.1A and I.2A

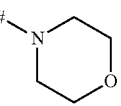

| No. | Formula | R¹ | R² | R³ |
|---|---|---|---|---|
| A-466 | I.1A | $CH_3$ | #-N(morpholine) | $SCH_3$ |
| A-467 | I.1A | $CH_3$ | $C_6H_5$ | H |
| A-468 | I.1A | $CH_3$ | $C_6H_5$ | $CH_3$ |
| A-469 | I.1A | $CH_3$ | $C_6H_5$ | $CF_3$ |
| A-470 | I.1A | $CH_3$ | $C_6H_5$ | $CHF_2$ |
| A-471 | I.1A | $CH_3$ | $C_6H_5$ | $OCH_3$ |
| A-472 | I.1A | $CH_3$ | $C_6H_5$ | $OCHF_2$ |
| A-473 | I.1A | $CH_3$ | $C_6H_5$ | $SCH_3$ |
| A-474 | I.1A | $CH_3$ | 4-F—$C_6H_4$ | H |
| A-475 | I.1A | $CH_3$ | 4-F—$C_6H_4$ | $CH_3$ |
| A-476 | I.1A | $CH_3$ | 4-F—$C_6H_4$ | $CF_3$ |
| A-477 | I.1A | $CH_3$ | 4-F—$C_6H_4$ | $CHF_2$ |
| A-478 | I.1A | $CH_3$ | 4-F—$C_6H_4$ | $OCH_3$ |
| A-479 | I.1A | $CH_3$ | 4-F—$C_6H_4$ | $OCHF_2$ |
| A-480 | I.1A | $CH_3$ | 4-F—$C_6H_4$ | $SCH_3$ |
| A-481 | I.1A | $CH_3$ | 4-Cl—$C_6H_4$ | H |
| A-482 | I.1A | $CH_3$ | 4-Cl—$C_6H_4$ | $CH_3$ |
| A-483 | I.1A | $CH_3$ | 4-Cl—$C_6H_4$ | $CF_3$ |
| A-484 | I.1A | $CH_3$ | 4-Cl—$C_6H_4$ | $CHF_2$ |
| A-485 | I.1A | $CH_3$ | 4-Cl—$C_6H_4$ | $OCH_3$ |
| A-486 | I.1A | $CH_3$ | 4-Cl—$C_6H_4$ | $OCHF_2$ |
| A-487 | I.1A | $CH_3$ | 4-Cl—$C_6H_4$ | $SCH_3$ |
| A-488 | I.1A | $CH_3$ | 4-$OCH_3$—$C_6H_4$ | H |
| A-489 | I.1A | $CH_3$ | 4-$OCH_3$—$C_6H_4$ | $CH_3$ |
| A-490 | I.1A | $CH_3$ | 4-$OCH_3$—$C_6H_4$ | $CF_3$ |
| A-491 | I.1A | $CH_3$ | 4-$OCH_3$—$C_6H_4$ | $CHF_2$ |
| A-492 | I.1A | $CH_3$ | 4-$OCH_3$—$C_6H_4$ | $OCH_3$ |
| A-493 | I.1A | $CH_3$ | 4-$OCH_3$—$C_6H_4$ | $OCHF_2$ |
| A-494 | I.1A | $CH_3$ | 4-$OCH_3$—$C_6H_4$ | $SCH_3$ |
| A-495 | I.1A | $CH_3$ | $CH=CH_2$ | H |
| A-496 | I.1A | $CH_3$ | $CH=CH_2$ | $CH_3$ |
| A-497 | I.1A | $CH_3$ | $CH=CH_2$ | $CF_3$ |
| A-498 | I.1A | $CH_3$ | $CH=CH_2$ | $CHF_2$ |
| A-499 | I.1A | $CH_3$ | $CH=CH_2$ | $OCH_3$ |
| A-500 | I.1A | $CH_3$ | $CH=CH_2$ | $OCHF_2$ |
| A-501 | I.1A | $CH_3$ | $CH=CH_2$ | $SCH_3$ |
| A-502 | I.1A | $CH_3$ | $CH=CH—CH_3$ | H |
| A-503 | I.1A | $CH_3$ | $CH=CH—CH_3$ | $CH_3$ |
| A-504 | I.1A | $CH_3$ | $CH=CH—CH_3$ | $CF_3$ |
| A-505 | I.1A | $CH_3$ | $CH=CH—CH_3$ | $CHF_2$ |
| A-506 | I.1A | $CH_3$ | $CH=CH—CH_3$ | $OCH_3$ |
| A-507 | I.1A | $CH_3$ | $CH=CH—CH_3$ | $OCHF_2$ |
| A-508 | I.1A | $CH_3$ | $CH=CH—CH_3$ | $SCH_3$ |
| A-509 | I.1A | $CH_3$ | $CH_2CH=CH_2$ | H |
| A-510 | I.1A | $CH_3$ | $CH_2CH=CH_2$ | $CH_3$ |
| A-511 | I.1A | $CH_3$ | $CH_2CH=CH_2$ | $CF_3$ |
| A-512 | I.1A | $CH_3$ | $CH_2CH=CH_2$ | $CHF_2$ |

TABLE A-continued

Compounds of the formula I which correspond to the formulae I.1A and I.2A

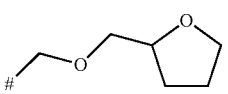
I.1A

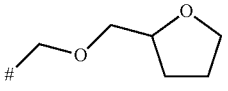
I.2A

| No. | Formula | R¹ | R² | R³ |
|---|---|---|---|---|
| A-513 | I.1A | $CH_3$ | $CH_2CH=CH_2$ | $OCH_3$ |
| A-514 | I.1A | $CH_3$ | $CH_2CH=CH_2$ | $OCHF_2$ |
| A-515 | I.1A | $CH_3$ | $CH_2CH=CH_2$ | $SCH_3$ |
| A-516 | I.1A | $CH_3$ | $CH_2C\equiv CH$ | H |
| A-517 | I.1A | $CH_3$ | $CH_2C\equiv CH$ | $CH_3$ |
| A-518 | I.1A | $CH_3$ | $CH_2C\equiv CH$ | $CF_3$ |
| A-519 | I.1A | $CH_3$ | $CH_2C\equiv CH$ | $CHF_2$ |
| A-520 | I.1A | $CH_3$ | $CH_2C\equiv CH$ | $OCH_3$ |
| A-521 | I.1A | $CH_3$ | $CH_2C\equiv CH$ | $OCHF_2$ |
| A-522 | I.1A | $CH_3$ | $CH_2C\equiv CH$ | $SCH_3$ |
| A-523 | I.1A | $CH_3$ | $CH_2OCH_2CF_3$ | H |
| A-524 | I.1A | $CH_3$ | $CH_2OCH_2CF_3$ | $CH_3$ |
| A-525 | I.1A | $CH_3$ | $CH_2OCH_2CF_3$ | $CF_3$ |
| A-526 | I.1A | $CH_3$ | $CH_2OCH_2CF_3$ | $CHF_2$ |
| A-527 | I.1A | $CH_3$ | $CH_2OCH_2CF_3$ | $OCH_3$ |
| A-528 | I.1A | $CH_3$ | $CH_2OCH_2CF_3$ | $OCHF_2$ |
| A-529 | I.1A | $CH_3$ | $CH_2OCH_2CF_3$ | $SCH_3$ |
| A-530 | I.1A | $CH_3$ | 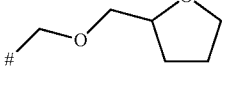 | H |
| A-531 | I.1A | $CH_3$ | 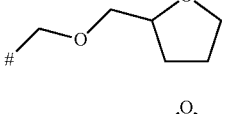 | $CH_3$ |
| A-532 | I.1A | $CH_3$ | 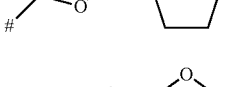 | $CF_3$ |
| A-533 | I.1A | $CH_3$ |  | $CHF_2$ |
| A-534 | I.1A | $CH_3$ |  | $OCH_3$ |
| A-535 | I.1A | $CH_3$ |  | $OCHF_2$ |

TABLE A-continued

Compounds of the formula I which correspond to the formulae I.1A and I.2A

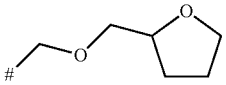

| No. | Formula | R¹ | R² | R³ |
|---|---|---|---|---|
| A-536 | I.1A | CH$_3$ | #-CH$_2$-O-CH$_2$-(tetrahydrofuran-2-yl) | SCH$_3$ |
| A-537 | I.1A | CH$_3$ | OCH$_2$CH$_3$ | H |
| A-538 | I.1A | CH$_3$ | OCH$_2$CH$_3$ | CH$_3$ |
| A-539 | I.1A | CH$_3$ | OCH$_2$CH$_3$ | CF$_3$ |
| A-540 | I.1A | CH$_3$ | OCH$_2$CH$_3$ | CHF$_2$ |
| A-541 | I.1A | CH$_3$ | OCH$_2$CH$_3$ | OCH$_3$ |
| A-542 | I.1A | CH$_3$ | OCH$_2$CH$_3$ | OCHF$_2$ |
| A-543 | I.1A | CH$_3$ | OCH$_2$CH$_3$ | SCH$_3$ |
| A-544 | I.1A | CH$_3$ | OCH$_2$CH$_2$OCH$_3$ | H |
| A-545 | I.1A | CH$_3$ | OCH$_2$CH$_2$OCH$_3$ | CH$_3$ |
| A-546 | I.1A | CH$_3$ | OCH$_2$CH$_2$OCH$_3$ | CF$_3$ |
| A-547 | I.1A | CH$_3$ | OCH$_2$CH$_2$OCH$_3$ | CHF$_2$ |
| A-548 | I.1A | CH$_3$ | OCH$_2$CH$_2$OCH$_3$ | OCH$_3$ |
| A-549 | I.1A | CH$_3$ | OCH$_2$CH$_2$OCH$_3$ | OCHF$_2$ |
| A-550 | I.1A | CH$_3$ | OCH$_2$CH$_2$OCH$_3$ | SCH$_3$ |
| A-551 | I.1A | CH$_3$ | SO$_2$CH$_3$ | H |
| A-552 | I.1A | CH$_3$ | SO$_2$CH$_3$ | CH$_3$ |
| A-553 | I.1A | CH$_3$ | SO$_2$CH$_3$ | CF$_3$ |
| A-554 | I.1A | CH$_3$ | SO$_2$CH$_3$ | CHF$_2$ |
| A-555 | I.1A | CH$_3$ | SO$_2$CH$_3$ | OCH$_3$ |
| A-556 | I.1A | CH$_3$ | SO$_2$CH$_3$ | OCHF$_2$ |
| A-557 | I.1A | CH$_3$ | SO$_2$CH$_3$ | SCH$_3$ |
| A-558 | I.1A | CH$_3$ | SO$_2$CH$_2$CH$_3$ | H |
| A-559 | I.1A | CH$_3$ | SO$_2$CH$_2$CH$_3$ | CH$_3$ |
| A-560 | I.1A | CH$_3$ | SO$_2$CH$_2$CH$_3$ | CF$_3$ |
| A-561 | I.1A | CH$_3$ | SO$_2$CH$_2$CH$_3$ | CHF$_2$ |
| A-562 | I.1A | CH$_3$ | SO$_2$CH$_2$CH$_3$ | OCH$_3$ |
| A-563 | I.1A | CH$_3$ | SO$_2$CH$_2$CH$_3$ | OCHF$_2$ |
| A-564 | I.1A | CH$_3$ | SO$_2$CH$_2$CH$_3$ | SCH$_3$ |
| A-565 | I.1A | CH$_3$ | SO$_2$CH(CH$_3$)$_2$ | H |
| A-566 | I.1A | CH$_3$ | SO$_2$CH(CH$_3$)$_2$ | CH$_3$ |
| A-567 | I.1A | CH$_3$ | SO$_2$CH(CH$_3$)$_2$ | CF$_3$ |
| A-568 | I.1A | CH$_3$ | SO$_2$CH(CH$_3$)$_2$ | CHF$_2$ |
| A-569 | I.1A | CH$_3$ | SO$_2$CH(CH$_3$)$_2$ | OCH$_3$ |
| A-570 | I.1A | CH$_3$ | SO$_2$CH(CH$_3$)$_2$ | OCHF$_2$ |
| A-571 | I.1A | CH$_3$ | SO$_2$CH(CH$_3$)$_2$ | SCH$_3$ |
| A-572 | I.1A | CH$_3$ | COOCH$_3$ | H |
| A-573 | I.1A | CH$_3$ | COOCH$_3$ | CH$_3$ |
| A-574 | I.1A | CH$_3$ | COOCH$_3$ | CF$_3$ |
| A-575 | I.1A | CH$_3$ | COOCH$_3$ | CHF$_2$ |
| A-576 | I.1A | CH$_3$ | COOCH$_3$ | OCH$_3$ |
| A-577 | I.1A | CH$_3$ | COOCH$_3$ | OCHF$_2$ |
| A-578 | I.1A | CH$_3$ | COOCH$_3$ | SCH$_3$ |
| A-579 | I.1A | CH$_3$ | COOCH$_2$CH$_3$ | H |
| A-580 | I.1A | CH$_3$ | COOCH$_2$CH$_3$ | CH$_3$ |
| A-581 | I.1A | CH$_3$ | COOCH$_2$CH$_3$ | CF$_3$ |
| A-582 | I.1A | CH$_3$ | COOCH$_2$CH$_3$ | CHF$_2$ |

TABLE A-continued

Compounds of the formula I which correspond to the formulae I.1A and I.2A

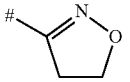

I.1A

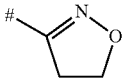

I.2A

| No. | Formula | R¹ | R² | R³ |
|---|---|---|---|---|
| A-583 | I.1A | $CH_3$ | $COOCH_2CH_3$ | $OCH_3$ |
| A-584 | I.1A | $CH_3$ | $COOCH_2CH_3$ | $OCHF_2$ |
| A-585 | I.1A | $CH_3$ | $COOCH_2CH_3$ | $SCH_3$ |
| A-586 | I.1A | $CH_3$ | $\#^2$—$CH_2CH_2SO_2$—$\#^3$ | |
| A-587 | I.1A | $CH_3$ | $\#^2$—$CH(CH_3)CH_2SO_2$—$\#^3$ | |
| A-588 | I.1A | $CH_3$ | $\#^2$—$C(CH_3)_2CH_2SO_2$—$\#^3$ | |
| A-589 | I.1A | $CH_3$ | $\#^2$—$SO_2CH_2CH_2SO_2$—$\#^3$ | |
| A-590 | I.1A | $CH_3$ | $\#^2$—$CH(OCH_2CH_2F)CH_2CH_2SO_2$—$\#^3$ | |
| A-591 | I.1A | $CH_3$ | $\#^2$—$C(=NOCH_3)CH_2CH_2SO_2$—$\#^3$ | |
| A-592 | I.1A | $CH_3$ | $\#^2$—$SO_2CH_2CH_2C(CH_3)_2$—$\#^3$ | |
| A-593 | I.1A | $CH_3$ | $\#^2$—$N(CH_3)C(=O)S$—$\#^3$ | |
| A-594 | I.1A | $CH_3$ | $\#^2$—$C(=O)N(CH_3)SO_2$—$\#^3$ | |
| A-595 | I.1A | $CF_3$ | 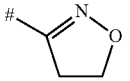 | H |
| A-596 | I.1A | $CF_3$ | 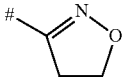 | $CH_3$ |
| A-597 | I.1A | $CF_3$ | 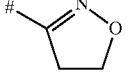 | $CF_3$ |
| A-598 | I.1A | $CF_3$ | 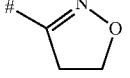 | $CHF_2$ |
| A-599 | I.1A | $CF_3$ | 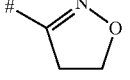 | $OCH_3$ |
| A-600 | I.1A | $CF_3$ | 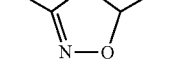 | $OCHF_2$ |
| A-601 | I.1A | $CF_3$ | | $SCH_3$ |
| A-602 | I.1A | $CF_3$ | | H |

TABLE A-continued

Compounds of the formula I which correspond to the formulae I.1A and I.2A

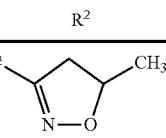
I.1A

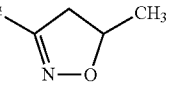
I.2A

| No. | Formula | R¹ | R² | R³ |
|---|---|---|---|---|
| A-603 | I.1A | CF$_3$ | #-(5-methyl-4,5-dihydroisoxazol-3-yl) | CH$_3$ |
| A-604 | I.1A | CF$_3$ | #-(5-methyl-4,5-dihydroisoxazol-3-yl) | CF$_3$ |
| A-605 | I.1A | CF$_3$ | #-(5-methyl-4,5-dihydroisoxazol-3-yl) | CHF$_2$ |
| A-606 | I.1A | CF$_3$ | #-(5-methyl-4,5-dihydroisoxazol-3-yl) | OCH$_3$ |
| A-607 | I.1A | CF$_3$ | #-(5-methyl-4,5-dihydroisoxazol-3-yl) | OCHF$_2$ |
| A-608 | I.1A | CF$_3$ | #-(5-methyl-4,5-dihydroisoxazol-3-yl) | SCH$_3$ |
| A-609 | I.1A | CF$_3$ | #-(isoxazol-3-yl) | H |
| A-610 | I.1A | CF$_3$ | #-(isoxazol-3-yl) | CH$_3$ |
| A-611 | I.1A | CF$_3$ | #-(isoxazol-3-yl) | CF$_3$ |
| A-612 | I.1A | CF$_3$ | #-(isoxazol-3-yl) | CHF$_2$ |

TABLE A-continued

Compounds of the formula I which correspond to the formulae I.1A and I.2A

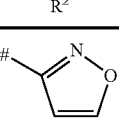
I.1A

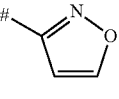
I.2A

| No. | Formula | R¹ | R² | R³ |
|---|---|---|---|---|
| A-613 | I.1A | CF$_3$ | # isoxazol-3-yl | OCH$_3$ |
| A-614 | I.1A | CF$_3$ | # isoxazol-3-yl | OCHF$_2$ |
| A-615 | I.1A | CF$_3$ | # isoxazol-3-yl | SCH$_3$ |
| A-616 | I.1A | CF$_3$ | # 5-methylisoxazol-3-yl | H |
| A-617 | I.1A | CF$_3$ | # 5-methylisoxazol-3-yl | CH$_3$ |
| A-618 | I.1A | CF$_3$ | # 5-methylisoxazol-3-yl | CF$_3$ |
| A-619 | I.1A | CF$_3$ | # 5-methylisoxazol-3-yl | CHF$_2$ |
| A-620 | I.1A | CF$_3$ | # 5-methylisoxazol-3-yl | OCH$_3$ |
| A-621 | I.1A | CF$_3$ | # 5-methylisoxazol-3-yl | OCHF$_2$ |
| A-622 | I.1A | CF$_3$ | # 5-methylisoxazol-3-yl | SCH$_3$ |

TABLE A-continued

Compounds of the formula I which correspond to the formulae I.1A and I.2A

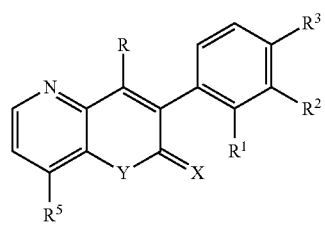
I.1A

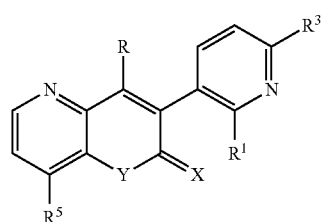
I.2A

| No. | Formula | R¹ | R² | R³ |
|---|---|---|---|---|
| A-623 | I.1A | $CF_3$ | #⟨4,5-dihydro-3-methylisoxazol-5-yl⟩ | H |
| A-624 | I.1A | $CF_3$ | #⟨4,5-dihydro-3-methylisoxazol-5-yl⟩ | $CH_3$ |
| A-625 | I.1A | $CF_3$ | #⟨4,5-dihydro-3-methylisoxazol-5-yl⟩ | $CF_3$ |
| A-626 | I.1A | $CF_3$ | #⟨4,5-dihydro-3-methylisoxazol-5-yl⟩ | $CHF_2$ |
| A-627 | I.1A | $CF_3$ | #⟨4,5-dihydro-3-methylisoxazol-5-yl⟩ | $OCH_3$ |
| A-628 | I.1A | $CF_3$ | #⟨4,5-dihydro-3-methylisoxazol-5-yl⟩ | $OCHF_2$ |
| A-629 | I.1A | $CF_3$ | #⟨4,5-dihydro-3-methylisoxazol-5-yl⟩ | $SCH_3$ |
| A-630 | I.1A | $CF_3$ | #⟨3-methylisoxazol-5-yl⟩ | H |
| A-631 | I.1A | $CF_3$ | #⟨3-methylisoxazol-5-yl⟩ | $CH_3$ |
| A-632 | I.1A | $CF_3$ | #⟨3-methylisoxazol-5-yl⟩ | $CF_3$ |

TABLE A-continued
Compounds of the formula I which correspond to the formulae I.1A and I.2A
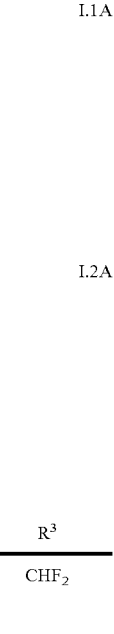  I.1A
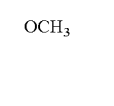  I.2A
| No. | Formula | R¹ | R² | R³ |
|---|---|---|---|---|
| A-633 | I.1A | CF$_3$ |  | CHF$_2$ |
| A-634 | I.1A | CF$_3$ |  | OCH$_3$ |
| A-635 | I.1A | CF$_3$ |  | OCHF$_2$ |
| A-636 | I.1A | CF$_3$ |  | SCH$_3$ |
| A-637 | I.1A | CF$_3$ |  | H |
| A-638 | I.1A | CF$_3$ |  | CH$_3$ |
| A-639 | I.1A | CF$_3$ |  | CF$_3$ |
| A-640 | I.1A | CF$_3$ |  | CHF$_2$ |
| A-641 | I.1A | CF$_3$ |  | OCH$_3$ |
| A-642 | I.1A | CF$_3$ |  | OCHF$_2$ |

TABLE A-continued
Compounds of the formula I which correspond to the formulae I.1A and I.2A
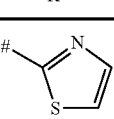
I.1A
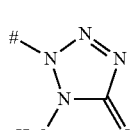
I.2A
| No. | Formula | R¹ | R² | R³ |
|---|---|---|---|---|
| A-643 | I.1A | CF$_3$ | 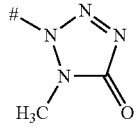 | SCH$_3$ |
| A-644 | I.1A | CF$_3$ | 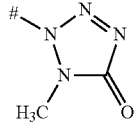 | H |
| A-645 | I.1A | CF$_3$ | 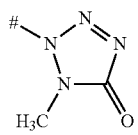 | CH$_3$ |
| A-646 | I.1A | CF$_3$ | 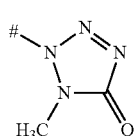 | CF$_3$ |
| A-647 | I.1A | CF$_3$ | 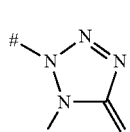 | CHF$_2$ |
| A-648 | I.1A | CF$_3$ | | OCH$_3$ |
| A-649 | I.1A | CF$_3$ | | OCHF$_2$ |

TABLE A-continued
Compounds of the formula I which correspond to the formulae I.1A and I.2A
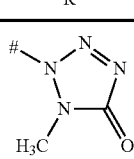
I.1A
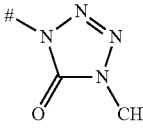
I.2A
| No. | Formula | R¹ | R² | R³ |
|---|---|---|---|---|
| A-650 | I.1A | CF$_3$ | 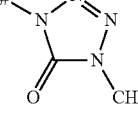 | SCH$_3$ |
| A-651 | I.1A | CF$_3$ | 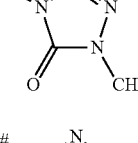 | H |
| A-652 | I.1A | CF$_3$ | 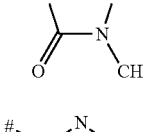 | CH$_3$ |
| A-653 | I.1A | CF$_3$ | 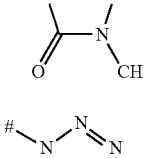 | CF$_3$ |
| A-654 | I.1A | CF$_3$ | 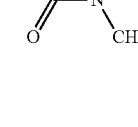 | CHF$_2$ |
| A-655 | I.1A | CF$_3$ |  | OCH$_3$ |
| A-656 | I.1A | CF$_3$ |  | OCHF$_2$ |

TABLE A-continued

Compounds of the formula I which correspond to the formulae I.1A and I.2A

I.1A

I.2A

| No. | Formula | R¹ | R² | R³ |
|---|---|---|---|---|
| A-657 | I.1A | CF$_3$ | 1-(4-methyl-5-oxo-4,5-dihydro-1H-tetrazol-1-yl) | SCH$_3$ |
| A-658 | I.1A | CF$_3$ | morpholin-4-yl | H |
| A-659 | I.1A | CF$_3$ | morpholin-4-yl | CH$_3$ |
| A-660 | I.1A | CF$_3$ | morpholin-4-yl | CF$_3$ |
| A-661 | I.1A | CF$_3$ | morpholin-4-yl | CHF$_2$ |
| A-662 | I.1A | CF$_3$ | morpholin-4-yl | OCH$_3$ |
| A-663 | I.1A | CF$_3$ | morpholin-4-yl | OCHF$_2$ |
| A-664 | I.1A | CF$_3$ | morpholin-4-yl | SCH$_3$ |
| A-665 | I.1A | CF$_3$ | C$_6$H$_5$ | H |
| A-666 | I.1A | CF$_3$ | C$_6$H$_5$ | CH$_3$ |
| A-667 | I.1A | CF$_3$ | C$_6$H$_5$ | CF$_3$ |
| A-668 | I.1A | CF$_3$ | C$_6$H$_5$ | CHF$_2$ |

TABLE A-continued

Compounds of the formula I which correspond to the formulae I.1A and I.2A

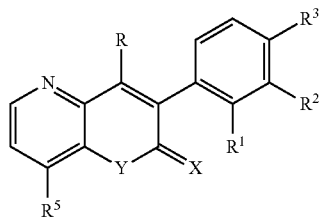

I.1A

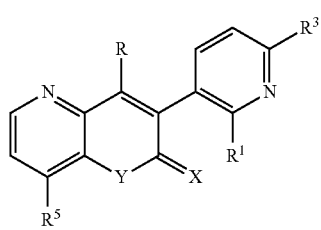

I.2A

| No. | Formula | R¹ | R² | R³ |
|---|---|---|---|---|
| A-669 | I.1A | $CF_3$ | $C_6H_5$ | $OCH_3$ |
| A-670 | I.1A | $CF_3$ | $C_6H_5$ | $OCHF_2$ |
| A-671 | I.1A | $CF_3$ | $C_6H_5$ | $SCH_3$ |
| A-672 | I.1A | $CF_3$ | 4-F—$C_6H_4$ | H |
| A-673 | I.1A | $CF_3$ | 4-F—$C_6H_4$ | $CH_3$ |
| A-674 | I.1A | $CF_3$ | 4-F—$C_6H_4$ | $CF_3$ |
| A-675 | I.1A | $CF_3$ | 4-F—$C_6H_4$ | $CHF_2$ |
| A-676 | I.1A | $CF_3$ | 4-F—$C_6H_4$ | $OCH_3$ |
| A-677 | I.1A | $CF_3$ | 4-F—$C_6H_4$ | $OCHF_2$ |
| A-678 | I.1A | $CF_3$ | 4-F—$C_6H_4$ | $SCH_3$ |
| A-679 | I.1A | $CF_3$ | 4-Cl—$C_6H_4$ | H |
| A-680 | I.1A | $CF_3$ | 4-Cl—$C_6H_4$ | $CH_3$ |
| A-681 | I.1A | $CF_3$ | 4-Cl—$C_6H_4$ | $CF_3$ |
| A-682 | I.1A | $CF_3$ | 4-Cl—$C_6H_4$ | $CHF_2$ |
| A-683 | I.1A | $CF_3$ | 4-Cl—$C_6H_4$ | $OCH_3$ |
| A-684 | I.1A | $CF_3$ | 4-Cl—$C_6H_4$ | $OCHF_2$ |
| A-685 | I.1A | $CF_3$ | 4-Cl—$C_6H_4$ | $SCH_3$ |
| A-686 | I.1A | $CF_3$ | 4-$OCH_3$—$C_6H_4$ | H |
| A-687 | I.1A | $CF_3$ | 4-$OCH_3$—$C_6H_4$ | $CH_3$ |
| A-688 | I.1A | $CF_3$ | 4-$OCH_3$—$C_6H_4$ | $CF_3$ |
| A-689 | I.1A | $CF_3$ | 4-$OCH_3$—$C_6H_4$ | $CHF_2$ |
| A-690 | I.1A | $CF_3$ | 4-$OCH_3$—$C_6H_4$ | $OCH_3$ |
| A-691 | I.1A | $CF_3$ | 4-$OCH_3$—$C_6H_4$ | $OCHF_2$ |
| A-692 | I.1A | $CF_3$ | 4-$OCH_3$—$C_6H_4$ | $SCH_3$ |
| A-693 | I.1A | $CF_3$ | $CH=CH_2$ | H |
| A-694 | I.1A | $CF_3$ | $CH=CH_2$ | $CH_3$ |
| A-695 | I.1A | $CF_3$ | $CH=CH_2$ | $CF_3$ |
| A-696 | I.1A | $CF_3$ | $CH=CH_2$ | $CHF_2$ |
| A-697 | I.1A | $CF_3$ | $CH=CH_2$ | $OCH_3$ |
| A-698 | I.1A | $CF_3$ | $CH=CH_2$ | $OCHF_2$ |
| A-699 | I.1A | $CF_3$ | $CH=CH_2$ | $SCH_3$ |
| A-700 | I.1A | $CF_3$ | $CH=CH—CH_3$ | H |
| A-701 | I.1A | $CF_3$ | $CH=CH—CH_3$ | $CH_3$ |
| A-702 | I.1A | $CF_3$ | $CH=CH—CH_3$ | $CF_3$ |
| A-703 | I.1A | $CF_3$ | $CH=CH—CH_3$ | $CHF_2$ |
| A-704 | I.1A | $CF_3$ | $CH=CH—CH_3$ | $OCH_3$ |
| A-705 | I.1A | $CF_3$ | $CH=CH—CH_3$ | $OCHF_2$ |
| A-706 | I.1A | $CF_3$ | $CH=CH—CH_3$ | $SCH_3$ |
| A-707 | I.1A | $CF_3$ | $CH_2CH=CH_2$ | H |
| A-708 | I.1A | $CF_3$ | $CH_2CH=CH_2$ | $CH_3$ |
| A-709 | I.1A | $CF_3$ | $CH_2CH=CH_2$ | $CF_3$ |
| A-710 | I.1A | $CF_3$ | $CH_2CH=CH_2$ | $CHF_2$ |
| A-711 | I.1A | $CF_3$ | $CH_2CH=CH_2$ | $OCH_3$ |
| A-712 | I.1A | $CF_3$ | $CH_2CH=CH_2$ | $OCHF_2$ |
| A-713 | I.1A | $CF_3$ | $CH_2CH=CH_2$ | $SCH_3$ |
| A-714 | I.1A | $CF_3$ | $CH_2C≡CH$ | H |
| A-715 | I.1A | $CF_3$ | $CH_2C≡CH$ | $CH_3$ |
| A-716 | I.1A | $CF_3$ | $CH_2C≡CH$ | $CF_3$ |
| A-717 | I.1A | $CF_3$ | $CH_2C≡CH$ | $CHF_2$ |
| A-718 | I.1A | $CF_3$ | $CH_2C≡CH$ | $OCH_3$ |
| A-719 | I.1A | $CF_3$ | $CH_2C≡CH$ | $OCHF_2$ |

TABLE A-continued

Compounds of the formula I which correspond to the formulae I.1A and I.2A

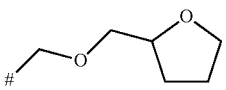

I.1A

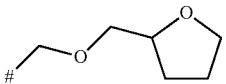

I.2A

| No. | Formula | R¹ | R² | R³ |
|---|---|---|---|---|
| A-720 | I.1A | $CF_3$ | $CH_2C{\equiv}CH$ | $SCH_3$ |
| A-721 | I.1A | $CF_3$ | $CH_2OCH_2CF_3$ | H |
| A-722 | I.1A | $CF_3$ | $CH_2OCH_2CF_3$ | $CH_3$ |
| A-723 | I.1A | $CF_3$ | $CH_2OCH_2CF_3$ | $CF_3$ |
| A-724 | I.1A | $CF_3$ | $CH_2OCH_2CF_3$ | $CHF_2$ |
| A-725 | I.1A | $CF_3$ | $CH_2OCH_2CF_3$ | $OCH_3$ |
| A-726 | I.1A | $CF_3$ | $CH_2OCH_2CF_3$ | $OCHF_2$ |
| A-727 | I.1A | $CF_3$ | $CH_2OCH_2CF_3$ | $SCH_3$ |
| A-728 | I.1A | $CF_3$ | 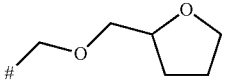 | H |
| A-729 | I.1A | $CF_3$ | 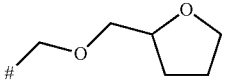 | $CH_3$ |
| A-730 | I.1A | $CF_3$ | 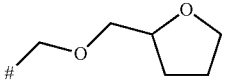 | $CF_3$ |
| A-731 | I.1A | $CF_3$ | 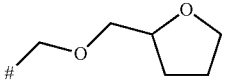 | $CHF_2$ |
| A-732 | I.1A | $CF_3$ | 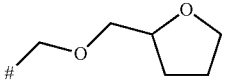 | $OCH_3$ |
| A-733 | I.1A | $CF_3$ | 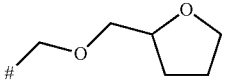 | $OCHF_2$ |
| A-734 | I.1A | $CF_3$ | 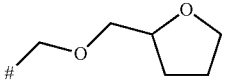 | $SCH_3$ |
| A-735 | I.1A | $CF_3$ | $OCH_2CH_3$ | H |
| A-736 | I.1A | $CF_3$ | $OCH_2CH_3$ | $CH_3$ |
| A-737 | I.1A | $CF_3$ | $OCH_2CH_3$ | $CF_3$ |
| A-738 | I.1A | $CF_3$ | $OCH_2CH_3$ | $CHF_2$ |
| A-739 | I.1A | $CF_3$ | $OCH_2CH_3$ | $OCH_3$ |
| A-740 | I.1A | $CF_3$ | $OCH_2CH_3$ | $OCHF_2$ |
| A-741 | I.1A | $CF_3$ | $OCH_2CH_3$ | $SCH_3$ |
| A-742 | I.1A | $CF_3$ | $OCH_2CH_2OCH_3$ | H |

TABLE A-continued

Compounds of the formula I which correspond to the formulae I.1A and I.2A

I.1A

I.2A

| No. | Formula | $R^1$ | $R^2$ | $R^3$ |
|---|---|---|---|---|
| A-743 | I.1A | $CF_3$ | $OCH_2CH_2OCH_3$ | $CH_3$ |
| A-744 | I.1A | $CF_3$ | $OCH_2CH_2OCH_3$ | $CF_3$ |
| A-745 | I.1A | $CF_3$ | $OCH_2CH_2OCH_3$ | $CHF_2$ |
| A-746 | I.1A | $CF_3$ | $OCH_2CH_2OCH_3$ | $OCH_3$ |
| A-747 | I.1A | $CF_3$ | $OCH_2CH_2OCH_3$ | $OCHF_2$ |
| A-748 | I.1A | $CF_3$ | $OCH_2CH_2OCH_3$ | $SCH_3$ |
| A-749 | I.1A | $CF_3$ | $SO_2CH_3$ | H |
| A-750 | I.1A | $CF_3$ | $SO_2CH_3$ | $CH_3$ |
| A-751 | I.1A | $CF_3$ | $SO_2CH_3$ | $CF_3$ |
| A-752 | I.1A | $CF_3$ | $SO_2CH_3$ | $CHF_2$ |
| A-753 | I.1A | $CF_3$ | $SO_2CH_3$ | $OCH_3$ |
| A-754 | I.1A | $CF_3$ | $SO_2CH_3$ | $OCHF_2$ |
| A-755 | I.1A | $CF_3$ | $SO_2CH_3$ | $SCH_3$ |
| A-756 | I.1A | $CF_3$ | $SO_2CH_2CH_3$ | H |
| A-757 | I.1A | $CF_3$ | $SO_2CH_2CH_3$ | $CH_3$ |
| A-758 | I.1A | $CF_3$ | $SO_2CH_2CH_3$ | $CF_3$ |
| A-759 | I.1A | $CF_3$ | $SO_2CH_2CH_3$ | $CHF_2$ |
| A-760 | I.1A | $CF_3$ | $SO_2CH_2CH_3$ | $OCH_3$ |
| A-761 | I.1A | $CF_3$ | $SO_2CH_2CH_3$ | $OCHF_2$ |
| A-762 | I.1A | $CF_3$ | $SO_2CH_2CH_3$ | $SCH_3$ |
| A-763 | I.1A | $CF_3$ | $SO_2CH(CH_3)_2$ | H |
| A-764 | I.1A | $CF_3$ | $SO_2CH(CH_3)_2$ | $CH_3$ |
| A-765 | I.1A | $CF_3$ | $SO_2CH(CH_3)_2$ | $CF_3$ |
| A-766 | I.1A | $CF_3$ | $SO_2CH(CH_3)_2$ | $CHF_2$ |
| A-767 | I.1A | $CF_3$ | $SO_2CH(CH_3)_2$ | $OCH_3$ |
| A-768 | I.1A | $CF_3$ | $SO_2CH(CH_3)_2$ | $OCHF_2$ |
| A-769 | I.1A | $CF_3$ | $SO_2CH(CH_3)_2$ | $SCH_3$ |
| A-770 | I.1A | $CF_3$ | $COOCH_3$ | H |
| A-771 | I.1A | $CF_3$ | $COOCH_3$ | $CH_3$ |
| A-772 | I.1A | $CF_3$ | $COOCH_3$ | $CF_3$ |
| A-773 | I.1A | $CF_3$ | $COOCH_3$ | $CHF_2$ |
| A-774 | I.1A | $CF_3$ | $COOCH_3$ | $OCH_3$ |
| A-775 | I.1A | $CF_3$ | $COOCH_3$ | $OCHF_2$ |
| A-776 | I.1A | $CF_3$ | $COOCH_3$ | $SCH_3$ |
| A-777 | I.1A | $CF_3$ | $COOCH_2CH_3$ | H |
| A-778 | I.1A | $CF_3$ | $COOCH_2CH_3$ | $CH_3$ |
| A-779 | I.1A | $CF_3$ | $COOCH_2CH_3$ | $CF_3$ |
| A-780 | I.1A | $CF_3$ | $COOCH_2CH_3$ | $CHF_2$ |
| A-781 | I.1A | $CF_3$ | $COOCH_2CH_3$ | $OCH_3$ |
| A-782 | I.1A | $CF_3$ | $COOCH_2CH_3$ | $OCHF_2$ |
| A-783 | I.1A | $CF_3$ | $COOCH_2CH_3$ | $SCH_3$ |
| A-784 | I.1A | $CF_3$ | $\#^2{-}CH_2CH_2SO_2{-}\#^3$ | |
| A-785 | I.1A | $CF_3$ | $\#^2{-}CH(CH_3)CH_2SO_2{-}\#^3$ | |
| A-786 | I.1A | $CF_3$ | $\#^2{-}C(CH_3)_2CH_2SO_2{-}\#^3$ | |
| A-787 | I.1A | $CF_3$ | $\#^2{-}SO_2CH_2CH_2SO_2{-}\#^3$ | |
| A-788 | I.1A | $CF_3$ | $\#^2{-}CH(OCH_2CH_2F)CH_2CH_2SO_2{-}\#^3$ | |
| A-789 | I.1A | $CF_3$ | $\#^2{-}C({=}NOCH_3)CH_2CH_2SO_2{-}\#^3$ | |
| A-790 | I.1A | $CF_3$ | $\#^2{-}SO_2CH_2CH_2C(CH_3)_2{-}\#^3$ | |
| A-791 | I.1A | $CF_3$ | $\#^2{-}N(CH_3)C({=}O)S{-}\#^3$ | |
| A-792 | I.1A | $CF_3$ | $\#^2{-}C({=}O)N(CH_3)SO_2{-}\#^3$ | |

TABLE A-continued
Compounds of the formula I which correspond to the formulae I.1A and I.2A
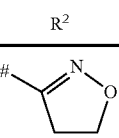
I.1A
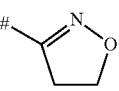
I.2A
| No. | Formula | R¹ | R² | R³ |
|---|---|---|---|---|
| A-793 | I.1A | $OCF_3$ | 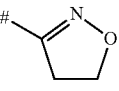 | H |
| A-794 | I.1A | $OCF_3$ | 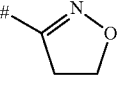 | $CH_3$ |
| A-795 | I.1A | $OCF_3$ | 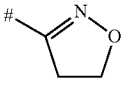 | $CF_3$ |
| A-796 | I.1A | $OCF_3$ | 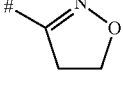 | $CHF_2$ |
| A-797 | I.1A | $OCF_3$ | 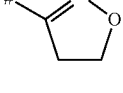 | $OCH_3$ |
| A-798 | I.1A | $OCF_3$ | 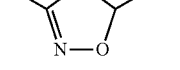 | $OCHF_2$ |
| A-799 | I.1A | $OCF_3$ | 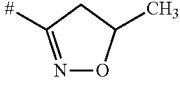 | $SCH_3$ |
| A-800 | I.1A | $OCF_3$ | 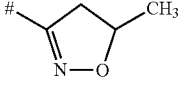 | H |
| A-801 | I.1A | $OCF_3$ | 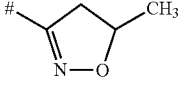 | $CH_3$ |
| A-802 | I.1A | $OCF_3$ | 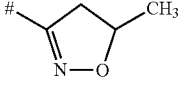 | $CF_3$ |

TABLE A-continued
Compounds of the formula I which correspond to the formulae I.1A and I.2A
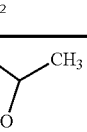
I.1A
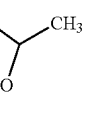
I.2A
| No. | Formula | R¹ | R² | R³ |
|---|---|---|---|---|
| A-803 | I.1A | $OCF_3$ | 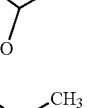 | $CHF_2$ |
| A-804 | I.1A | $OCF_3$ | 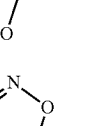 | $OCH_3$ |
| A-805 | I.1A | $OCF_3$ |  | $OCHF_2$ |
| A-806 | I.1A | $OCF_3$ |  | $SCH_3$ |
| A-807 | I.1A | $OCF_3$ |  | H |
| A-808 | I.1A | $OCF_3$ |  | $CH_3$ |
| A-809 | I.1A | $OCF_3$ |  | $CF_3$ |
| A-810 | I.1A | $OCF_3$ |  | $CHF_2$ |
| A-811 | I.1A | $OCF_3$ | # <br> (isoxazole) | $OCH_3$ |
| A-812 | I.1A | $OCF_3$ | # <br> (isoxazole) | $OCHF_2$ |

TABLE A-continued
Compounds of the formula I which correspond to the formulae I.1A and I.2A
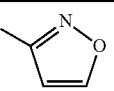
I.1A
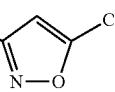
I.2A
| No. | Formula | R¹ | R² | R³ |
|---|---|---|---|---|
| A-813 | I.1A | OCF$_3$ | 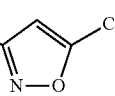 | SCH$_3$ |
| A-814 | I.1A | OCF$_3$ | 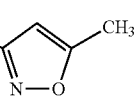 | H |
| A-815 | I.1A | OCF$_3$ | 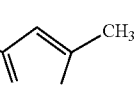 | CH$_3$ |
| A-816 | I.1A | OCF$_3$ | 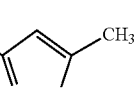 | CF$_3$ |
| A-817 | I.1A | OCF$_3$ | 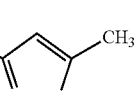 | CHF$_2$ |
| A-818 | I.1A | OCF$_3$ | 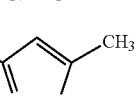 | OCH$_3$ |
| A-819 | I.1A | OCF$_3$ | 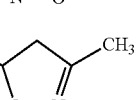 | OCHF$_2$ |
| A-820 | I.1A | OCF$_3$ | 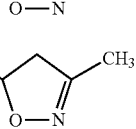 | SCH$_3$ |
| A-821 | I.1A | OCF$_3$ | | H |
| A-822 | I.1A | OCF$_3$ | | CH$_3$ |

TABLE A-continued

Compounds of the formula I which correspond to the formulae I.1A and I.2A

I.1A

I.2A

| No. | Formula | R¹ | R² | R³ |
|---|---|---|---|---|
| A-823 | I.1A | OCF$_3$ | 3-methyl-4,5-dihydroisoxazol-5-yl | CF$_3$ |
| A-824 | I.1A | OCF$_3$ | 3-methyl-4,5-dihydroisoxazol-5-yl | CHF$_2$ |
| A-825 | I.1A | OCF$_3$ | 3-methyl-4,5-dihydroisoxazol-5-yl | OCH$_3$ |
| A-826 | I.1A | OCF$_3$ | 3-methyl-4,5-dihydroisoxazol-5-yl | OCHF$_2$ |
| A-827 | I.1A | OCF$_3$ | 3-methyl-4,5-dihydroisoxazol-5-yl | SCH$_3$ |
| A-828 | I.1A | OCF$_3$ | 3-methylisoxazol-5-yl | H |
| A-829 | I.1A | OCF$_3$ | 3-methylisoxazol-5-yl | CH$_3$ |
| A-830 | I.1A | OCF$_3$ | 3-methylisoxazol-5-yl | CF$_3$ |
| A-831 | I.1A | OCF$_3$ | 3-methylisoxazol-5-yl | CHF$_2$ |
| A-832 | I.1A | OCF$_3$ | 3-methylisoxazol-5-yl | OCH$_3$ |

TABLE A-continued
Compounds of the formula I which correspond to the formulae I.1A and I.2A
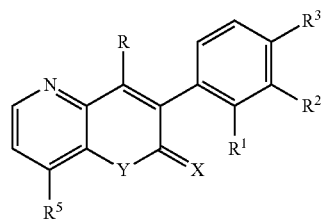
I.1A
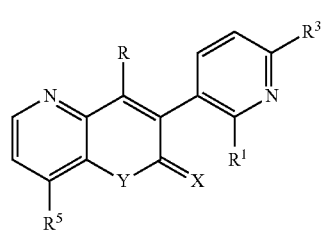
I.2A
| No. | Formula | R¹ | R² | R³ |
|---|---|---|---|---|
| A-833 | I.1A | OCF$_3$ |  | OCHF$_2$ |
| A-834 | I.1A | OCF$_3$ |  | SCH$_3$ |
| A-835 | I.1A | OCF$_3$ |  | H |
| A-836 | I.1A | OCF$_3$ |  | CH$_3$ |
| A-837 | I.1A | OCF$_3$ |  | CF$_3$ |
| A-838 | I.1A | OCF$_3$ |  | CHF$_2$ |
| A-839 | I.1A | OCF$_3$ |  | OCH$_3$ |
| A-840 | I.1A | OCF$_3$ |  | OCHF$_2$ |
| A-841 | I.1A | OCF$_3$ |  | SCH$_3$ |
| A-842 | I.1A | OCF$_3$ |  | H |

TABLE A-continued
Compounds of the formula I which correspond to the formulae I.1A and I.2A
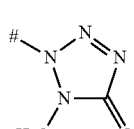
I.1A
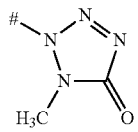
I.2A
| No. | Formula | R¹ | R² | R³ |
|---|---|---|---|---|
| A-843 | I.1A | OCF$_3$ | 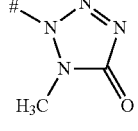 | CH$_3$ |
| A-844 | I.1A | OCF$_3$ | 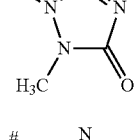 | CF$_3$ |
| A-845 | I.1A | OCF$_3$ | 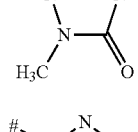 | CHF$_2$ |
| A-846 | I.1A | OCF$_3$ | 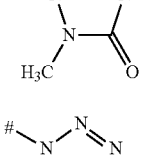 | OCH$_3$ |
| A-847 | I.1A | OCF$_3$ | 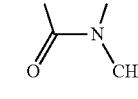 | OCHF$_2$ |
| A-848 | I.1A | OCF$_3$ | | SCH$_3$ |
| A-849 | I.1A | OCF$_3$ | | H |

TABLE A-continued
Compounds of the formula I which correspond to the formulae I.1A and I.2A
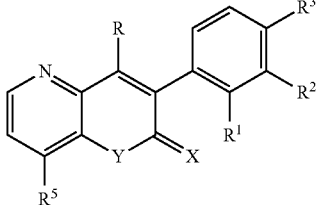
I.1A
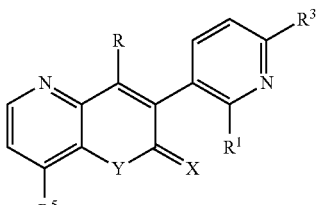
I.2A
| No. | Formula | $R^1$ | $R^2$ | $R^3$ |
|---|---|---|---|---|
| A-850 | I.1A | $OCF_3$ | 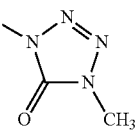 | $CH_3$ |
| A-851 | I.1A | $OCF_3$ | 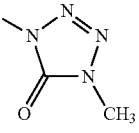 | $CF_3$ |
| A-852 | I.1A | $OCF_3$ | 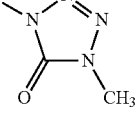 | $CHF_2$ |
| A-853 | I.1A | $OCF_3$ | 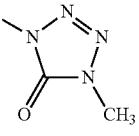 | $OCH_3$ |
| A-854 | I.1A | $OCF_3$ | 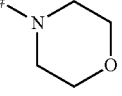 | $OCHF_2$ |
| A-855 | I.1A | $OCF_3$ |  | $SCH_3$ |
| A-856 | I.1A | $OCF_3$ |  | H |

TABLE A-continued

Compounds of the formula I which correspond to the formulae I.1A and I.2A

I.1A

I.2A

| No. | Formula | R$^1$ | R$^2$ | R$^3$ |
|---|---|---|---|---|
| A-857 | I.1A | OCF$_3$ | #–N(morpholine) | CH$_3$ |
| A-858 | I.1A | OCF$_3$ | #–N(morpholine) | CF$_3$ |
| A-859 | I.1A | OCF$_3$ | #–N(morpholine) | CHF$_2$ |
| A-860 | I.1A | OCF$_3$ | #–N(morpholine) | OCH$_3$ |
| A-861 | I.1A | OCF$_3$ | #–N(morpholine) | OCHF$_2$ |
| A-862 | I.1A | OCF$_3$ | #–N(morpholine) | SCH$_3$ |
| A-863 | I.1A | OCF$_3$ | C$_6$H$_5$ | H |
| A-864 | I.1A | OCF$_3$ | C$_6$H$_5$ | CH$_3$ |
| A-865 | I.1A | OCF$_3$ | C$_6$H$_5$ | CF$_3$ |
| A-866 | I.1A | OCF$_3$ | C$_6$H$_5$ | CHF$_2$ |
| A-867 | I.1A | OCF$_3$ | C$_6$H$_5$ | OCH$_3$ |
| A-868 | I.1A | OCF$_3$ | C$_6$H$_5$ | OCHF$_2$ |
| A-869 | I.1A | OCF$_3$ | C$_6$H$_5$ | SCH$_3$ |
| A-870 | I.1A | OCF$_3$ | 4-F—C$_6$H$_4$ | H |
| A-871 | I.1A | OCF$_3$ | 4-F—C$_6$H$_4$ | CH$_3$ |
| A-872 | I.1A | OCF$_3$ | 4-F—C$_6$H$_4$ | CF$_3$ |
| A-873 | I.1A | OCF$_3$ | 4-F—C$_6$H$_4$ | CHF$_2$ |
| A-874 | I.1A | OCF$_3$ | 4-F—C$_6$H$_4$ | OCH$_3$ |
| A-875 | I.1A | OCF$_3$ | 4-F—C$_6$H$_4$ | OCHF$_2$ |
| A-876 | I.1A | OCF$_3$ | 4-F—C$_6$H$_4$ | SCH$_3$ |
| A-877 | I.1A | OCF$_3$ | 4-Cl—C$_6$H$_4$ | H |
| A-878 | I.1A | OCF$_3$ | 4-Cl—C$_6$H$_4$ | CH$_3$ |
| A-879 | I.1A | OCF$_3$ | 4-Cl—C$_6$H$_4$ | CF$_3$ |

TABLE A-continued

Compounds of the formula I which correspond to the formulae I.1A and I.2A

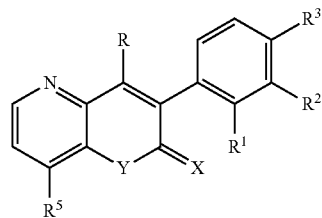
I.1A

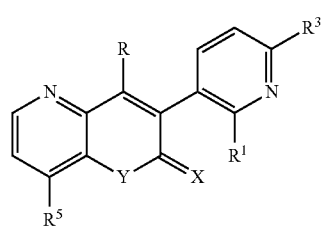
I.2A

| No. | Formula | R¹ | R² | R³ |
|---|---|---|---|---|
| A-880 | I.1A | OCF$_3$ | 4-Cl—C$_6$H$_4$ | CHF$_2$ |
| A-881 | I.1A | OCF$_3$ | 4-Cl—C$_6$H$_4$ | OCH$_3$ |
| A-882 | I.1A | OCF$_3$ | 4-Cl—C$_6$H$_4$ | OCHF$_2$ |
| A-883 | I.1A | OCF$_3$ | 4-Cl—C$_6$H$_4$ | SCH$_3$ |
| A-884 | I.1A | OCF$_3$ | 4-OCH$_3$—C$_6$H$_4$ | H |
| A-885 | I.1A | OCF$_3$ | 4-OCH$_3$—C$_6$H$_4$ | CH$_3$ |
| A-886 | I.1A | OCF$_3$ | 4-OCH$_3$—C$_6$H$_4$ | CF$_3$ |
| A-887 | I.1A | OCF$_3$ | 4-OCH$_3$—C$_6$H$_4$ | CHF$_2$ |
| A-888 | I.1A | OCF$_3$ | 4-OCH$_3$—C$_6$H$_4$ | OCH$_3$ |
| A-889 | I.1A | OCF$_3$ | 4-OCH$_3$—C$_6$H$_4$ | OCHF$_2$ |
| A-890 | I.1A | OCF$_3$ | 4-OCH$_3$—C$_6$H$_4$ | SCH$_3$ |
| A-891 | I.1A | OCF$_3$ | CH=CH$_2$ | H |
| A-892 | I.1A | OCF$_3$ | CH=CH$_2$ | CH$_3$ |
| A-893 | I.1A | OCF$_3$ | CH=CH$_2$ | CF$_3$ |
| A-894 | I.1A | OCF$_3$ | CH=CH$_2$ | CHF$_2$ |
| A-895 | I.1A | OCF$_3$ | CH=CH$_2$ | OCH$_3$ |
| A-896 | I.1A | OCF$_3$ | CH=CH$_2$ | OCHF$_2$ |
| A-897 | I.1A | OCF$_3$ | CH=CH$_2$ | SCH$_3$ |
| A-898 | I.1A | OCF$_3$ | CH=CH—CH$_3$ | H |
| A-899 | I.1A | OCF$_3$ | CH=CH—CH$_3$ | CH$_3$ |
| A-900 | I.1A | OCF$_3$ | CH=CH—CH$_3$ | CF$_3$ |
| A-901 | I.1A | OCF$_3$ | CH=CH—CH$_3$ | CHF$_2$ |
| A-902 | I.1A | OCF$_3$ | CH=CH—CH$_3$ | OCH$_3$ |
| A-903 | I.1A | OCF$_3$ | CH=CH—CH$_3$ | OCHF$_2$ |
| A-904 | I.1A | OCF$_3$ | CH=CH—CH$_3$ | SCH$_3$ |
| A-905 | I.1A | OCF$_3$ | CH$_2$CH=CH$_2$ | H |
| A-906 | I.1A | OCF$_3$ | CH$_2$CH=CH$_2$ | CH$_3$ |
| A-907 | I.1A | OCF$_3$ | CH$_2$CH=CH$_2$ | CF$_3$ |
| A-908 | I.1A | OCF$_3$ | CH$_2$CH=CH$_2$ | CHF$_2$ |
| A-909 | I.1A | OCF$_3$ | CH$_2$CH=CH$_2$ | OCH$_3$ |
| A-910 | I.1A | OCF$_3$ | CH$_2$CH=CH$_2$ | OCHF$_2$ |
| A-911 | I.1A | OCF$_3$ | CH$_2$CH=CH$_2$ | SCH$_3$ |
| A-912 | I.1A | OCF$_3$ | CH$_2$C≡CH | H |
| A-913 | I.1A | OCF$_3$ | CH$_2$C≡CH | CH$_3$ |
| A-914 | I.1A | OCF$_3$ | CH$_2$C≡CH | CF$_3$ |
| A-915 | I.1A | OCF$_3$ | CH$_2$C≡CH | CHF$_2$ |
| A-916 | I.1A | OCF$_3$ | CH$_2$C≡CH | OCH$_3$ |
| A-917 | I.1A | OCF$_3$ | CH$_2$C≡CH | OCHF$_2$ |
| A-918 | I.1A | OCF$_3$ | CH$_2$C≡CH | SCH$_3$ |
| A-919 | I.1A | OCF$_3$ | CH$_2$OCH$_2$CF$_3$ | H |
| A-920 | I.1A | OCF$_3$ | CH$_2$OCH$_2$CF$_3$ | CH$_3$ |
| A-921 | I.1A | OCF$_3$ | CH$_2$OCH$_2$CF$_3$ | CF$_3$ |
| A-922 | I.1A | OCF$_3$ | CH$_2$OCH$_2$CF$_3$ | CHF$_2$ |
| A-923 | I.1A | OCF$_3$ | CH$_2$OCH$_2$CF$_3$ | OCH$_3$ |
| A-924 | I.1A | OCF$_3$ | CH$_2$OCH$_2$CF$_3$ | OCHF$_2$ |
| A-925 | I.1A | OCF$_3$ | CH$_2$OCH$_2$CF$_3$ | SCH$_3$ |
| A-926 | I.1A | OCF$_3$ | ![tetrahydrofuran-2-ylmethoxyethyl] | H |

TABLE A-continued

Compounds of the formula I which correspond to the formulae I.1A and I.2A

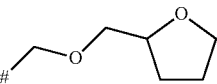

I.1A

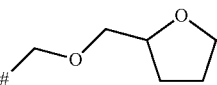

I.2A

| No. | Formula | R¹ | R² | R³ |
|---|---|---|---|---|
| A-927 | I.1A | OCF$_3$ | 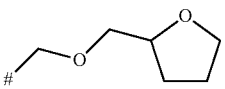 | CH$_3$ |
| A-928 | I.1A | OCF$_3$ | 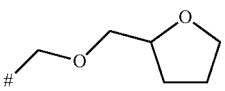 | CF$_3$ |
| A-929 | I.1A | OCF$_3$ | 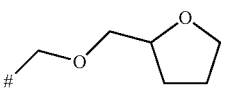 | CHF$_2$ |
| A-930 | I.1A | OCF$_3$ | 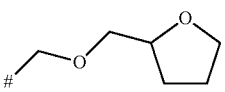 | OCH$_3$ |
| A-931 | I.1A | OCF$_3$ | | OCHF$_2$ |
| A-932 | I.1A | OCF$_3$ | | SCH$_3$ |
| A-933 | I.1A | OCF$_3$ | OCH$_2$CH$_3$ | H |
| A-934 | I.1A | OCF$_3$ | OCH$_2$CH$_3$ | CH$_3$ |
| A-935 | I.1A | OCF$_3$ | OCH$_2$CH$_3$ | CF$_3$ |
| A-936 | I.1A | OCF$_3$ | OCH$_2$CH$_3$ | CHF$_2$ |
| A-937 | I.1A | OCF$_3$ | OCH$_2$CH$_3$ | OCH$_3$ |
| A-938 | I.1A | OCF$_3$ | OCH$_2$CH$_3$ | OCHF$_2$ |
| A-939 | I.1A | OCF$_3$ | OCH$_2$CH$_3$ | SCH$_3$ |
| A-940 | I.1A | OCF$_3$ | OCH$_2$CH$_2$OCH$_3$ | H |
| A-941 | I.1A | OCF$_3$ | OCH$_2$CH$_2$OCH$_3$ | CH$_3$ |
| A-942 | I.1A | OCF$_3$ | OCH$_2$CH$_2$OCH$_3$ | CF$_3$ |
| A-943 | I.1A | OCF$_3$ | OCH$_2$CH$_2$OCH$_3$ | CHF$_2$ |
| A-944 | I.1A | OCF$_3$ | OCH$_2$CH$_2$OCH$_3$ | OCH$_3$ |
| A-945 | I.1A | OCF$_3$ | OCH$_2$CH$_2$OCH$_3$ | OCHF$_2$ |
| A-946 | I.1A | OCF$_3$ | OCH$_2$CH$_2$OCH$_3$ | SCH$_3$ |
| A-947 | I.1A | OCF$_3$ | SO$_2$CH$_3$ | H |
| A-948 | I.1A | OCF$_3$ | SO$_2$CH$_3$ | CH$_3$ |
| A-949 | I.1A | OCF$_3$ | SO$_2$CH$_3$ | CF$_3$ |
| A-950 | I.1A | OCF$_3$ | SO$_2$CH$_3$ | CHF$_2$ |
| A-951 | I.1A | OCF$_3$ | SO$_2$CH$_3$ | OCH$_3$ |
| A-952 | I.1A | OCF$_3$ | SO$_2$CH$_3$ | OCHF$_2$ |

TABLE A-continued

Compounds of the formula I which correspond to the formulae I.1A and I.2A

I.1A

I.2A

| No. | Formula | $R^1$ | $R^2$ | $R^3$ |
|---|---|---|---|---|
| A-953 | I.1A | $OCF_3$ | $SO_2CH_3$ | $SCH_3$ |
| A-954 | I.1A | $OCF_3$ | $SO_2CH_2CH_3$ | H |
| A-955 | I.1A | $OCF_3$ | $SO_2CH_2CH_3$ | $CH_3$ |
| A-956 | I.1A | $OCF_3$ | $SO_2CH_2CH_3$ | $CF_3$ |
| A-957 | I.1A | $OCF_3$ | $SO_2CH_2CH_3$ | $CHF_2$ |
| A-958 | I.1A | $OCF_3$ | $SO_2CH_2CH_3$ | $OCH_3$ |
| A-959 | I.1A | $OCF_3$ | $SO_2CH_2CH_3$ | $OCHF_2$ |
| A-960 | I.1A | $OCF_3$ | $SO_2CH_2CH_3$ | $SCH_3$ |
| A-961 | I.1A | $OCF_3$ | $SO_2CH(CH_3)_2$ | H |
| A-962 | I.1A | $OCF_3$ | $SO_2CH(CH_3)_2$ | $CH_3$ |
| A-963 | I.1A | $OCF_3$ | $SO_2CH(CH_3)_2$ | $CF_3$ |
| A-964 | I.1A | $OCF_3$ | $SO_2CH(CH_3)_2$ | $CHF_2$ |
| A-965 | I.1A | $OCF_3$ | $SO_2CH(CH_3)_2$ | $OCH_3$ |
| A-966 | I.1A | $OCF_3$ | $SO_2CH(CH_3)_2$ | $OCHF_2$ |
| A-967 | I.1A | $OCF_3$ | $SO_2CH(CH_3)_2$ | $SCH_3$ |
| A-968 | I.1A | $OCF_3$ | $COOCH_3$ | H |
| A-969 | I.1A | $OCF_3$ | $COOCH_3$ | $CH_3$ |
| A-970 | I.1A | $OCF_3$ | $COOCH_3$ | $CF_3$ |
| A-971 | I.1A | $OCF_3$ | $COOCH_3$ | $CHF_2$ |
| A-972 | I.1A | $OCF_3$ | $COOCH_3$ | $OCH_3$ |
| A-973 | I.1A | $OCF_3$ | $COOCH_3$ | $OCHF_2$ |
| A-974 | I.1A | $OCF_3$ | $COOCH_3$ | $SCH_3$ |
| A-975 | I.1A | $OCF_3$ | $COOCH_2CH_3$ | H |
| A-976 | I.1A | $OCF_3$ | $COOCH_2CH_3$ | $CH_3$ |
| A-977 | I.1A | $OCF_3$ | $COOCH_2CH_3$ | $CF_3$ |
| A-978 | I.1A | $OCF_3$ | $COOCH_2CH_3$ | $CHF_2$ |
| A-979 | I.1A | $OCF_3$ | $COOCH_2CH_3$ | $OCH_3$ |
| A-980 | I.1A | $OCF_3$ | $COOCH_2CH_3$ | $OCHF_2$ |
| A-981 | I.1A | $OCF_3$ | $COOCH_2CH_3$ | $SCH_3$ |
| A-982 | I.1A | $OCF_3$ | $\#^2$—$CH_2CH_2SO_2$—$\#^3$ | |
| A-983 | I.1A | $OCF_3$ | $\#^2$—$CH(CH_3)CH_2SO_2$—$\#^3$ | |
| A-984 | I.1A | $OCF_3$ | $\#^2$—$C(CH_3)_2CH_2SO_2$—$\#^3$ | |
| A-985 | I.1A | $OCF_3$ | $\#^2$—$SO_2CH_2CH_2SO_2$—$\#^3$ | |
| A-986 | I.1A | $OCF_3$ | $\#^2$—$CH(OCH_2CH_2F)CH_2CH_2SO_2$—$\#^3$ | |
| A-987 | I.1A | $OCF_3$ | $\#^2$—$C(=NOCH_3)CH_2CH_2SO_2$—$\#^3$ | |
| A-988 | I.1A | $OCF_3$ | $\#^2$—$SO_2CH_2CH_2C(CH_3)_2$—$\#^3$ | |
| A-989 | I.1A | $OCF_3$ | $\#^2$—$N(CH_3)C(=O)S$—$\#^3$ | |
| A-990 | I.1A | $OCF_3$ | $\#^2$—$C(=O)N(CH_3)SO_2$—$\#^3$ | |
| A-991 | I.1A | $SCF_3$ | 4,5-dihydroisoxazol-3-yl | H |
| A-992 | I.1A | $SCF_3$ | 4,5-dihydroisoxazol-3-yl | $CH_3$ |

TABLE A-continued

Compounds of the formula I which correspond to the formulae I.1A and I.2A

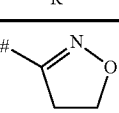

I.1A

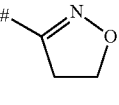

I.2A

| No. | Formula | R¹ | R² | R³ |
|---|---|---|---|---|
| A-993 | I.1A | SCF$_3$ | # isoxazoline | CF$_3$ |
| A-994 | I.1A | SCF$_3$ | # isoxazoline | CHF$_2$ |
| A-995 | I.1A | SCF$_3$ | # isoxazoline | OCH$_3$ |
| A-996 | I.1A | SCF$_3$ | # isoxazoline | OCHF$_2$ |
| A-997 | I.1A | SCF$_3$ | # isoxazoline | SCH$_3$ |
| A-998 | I.1A | SCF$_3$ | # methyl-isoxazoline | H |
| A-999 | I.1A | SCF$_3$ | # methyl-isoxazoline | CH$_3$ |
| A-1000 | I.1A | SCF$_3$ | # methyl-isoxazoline | CF$_3$ |
| A-1001 | I.1A | SCF$_3$ | # methyl-isoxazoline | CHF$_2$ |
| A-1002 | I.1A | SCF$_3$ | # methyl-isoxazoline | OCH$_3$ |

TABLE A-continued

Compounds of the formula I which correspond to the formulae I.1A and I.2A

I.1A

I.2A

| No. | Formula | R¹ | R² | R³ |
|---|---|---|---|---|
| A-1003 | I.1A | SCF₃ | #-(4,5-dihydroisoxazol-3-yl)-5-CH₃ | OCHF₂ |
| A-1004 | I.1A | SCF₃ | #-(4,5-dihydroisoxazol-3-yl)-5-CH₃ | SCH₃ |
| A-1005 | I.1A | SCF₃ | #-(isoxazol-3-yl) | H |
| A-1006 | I.1A | SCF₃ | #-(isoxazol-3-yl) | CH₃ |
| A-1007 | I.1A | SCF₃ | #-(isoxazol-3-yl) | CF₃ |
| A-1008 | I.1A | SCF₃ | #-(isoxazol-3-yl) | CHF₂ |
| A-1009 | I.1A | SCF₃ | #-(isoxazol-3-yl) | OCH₃ |
| A-1010 | I.1A | SCF₃ | #-(isoxazol-3-yl) | OCHF₂ |
| A-1011 | I.1A | SCF₃ | #-(isoxazol-3-yl) | SCH₃ |
| A-1012 | I.1A | SCF₃ | #-(5-CH₃-isoxazol-3-yl) | H |
| A-1013 | I.1A | SCF₃ | #-(5-CH₃-isoxazol-3-yl) | CH₃ |

TABLE A-continued

Compounds of the formula I which correspond to the formulae I.1A and I.2A

I.1A

I.2A

| No. | Formula | R¹ | R² | R³ |
|---|---|---|---|---|
| A-1014 | I.1A | SCF₃ | # isoxazole-CH₃ | CF₃ |
| A-1015 | I.1A | SCF₃ | # isoxazole-CH₃ | CHF₂ |
| A-1016 | I.1A | SCF₃ | # isoxazole-CH₃ | OCH₃ |
| A-1017 | I.1A | SCF₃ | # isoxazole-CH₃ | OCHF₂ |
| A-1018 | I.1A | SCF₃ | # isoxazole-CH₃ | SCH₃ |
| A-1019 | I.1A | SCF₃ | # isoxazoline-CH₃ | H |
| A-1020 | I.1A | SCF₃ | # isoxazoline-CH₃ | CH₃ |
| A-1021 | I.1A | SCF₃ | # isoxazoline-CH₃ | CF₃ |
| A-1022 | I.1A | SCF₃ | # isoxazoline-CH₃ | CHF₂ |
| A-1023 | I.1A | SCF₃ | # isoxazoline-CH₃ | OCH₃ |

TABLE A-continued
Compounds of the formula I which correspond to the formulae I.1A and I.2A
   I.1A
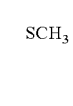   I.2A
| No. | Formula | R¹ | R² | R³ |
|---|---|---|---|---|
| A-1024 | I.1A | SCF$_3$ |  | OCHF$_2$ |
| A-1025 | I.1A | SCF$_3$ |  | SCH$_3$ |
| A-1026 | I.1A | SCF$_3$ |  | H |
| A-1027 | I.1A | SCF$_3$ |  | CH$_3$ |
| A-1028 | I.1A | SCF$_3$ |  | CF$_3$ |
| A-1029 | I.1A | SCF$_3$ |  | CHF$_2$ |
| A-1030 | I.1A | SCF$_3$ |  | OCH$_3$ |
| A-1031 | I.1A | SCF$_3$ |  | OCHF$_2$ |
| A-1032 | I.1A | SCF$_3$ |  | SCH$_3$ |
| A-1033 | I.1A | SCF$_3$ |  | H |

TABLE A-continued

Compounds of the formula I which correspond to the formulae I.1A and I.2A

I.1A

I.2A

| No. | Formula | R¹ | R² | R³ |
| --- | --- | --- | --- | --- |
| A-1034 | I.1A | $SCF_3$ | thiazol-2-yl | $CH_3$ |
| A-1035 | I.1A | $SCF_3$ | thiazol-2-yl | $CF_3$ |
| A-1036 | I.1A | $SCF_3$ | thiazol-2-yl | $CHF_2$ |
| A-1037 | I.1A | $SCF_3$ | thiazol-2-yl | $OCH_3$ |
| A-1038 | I.1A | $SCF_3$ | thiazol-2-yl | $OCHF_2$ |
| A-1039 | I.1A | $SCF_3$ | thiazol-2-yl | $SCH_3$ |
| A-1040 | I.1A | $SCF_3$ | 4-methyl-5-oxo-tetrazol-1-yl | H |
| A-1041 | I.1A | $SCF_3$ | 4-methyl-5-oxo-tetrazol-1-yl | $CH_3$ |
| A-1042 | I.1A | $SCF_3$ | 4-methyl-5-oxo-tetrazol-1-yl | $CF_3$ |

TABLE A-continued
Compounds of the formula I which correspond to the formulae I.1A and I.2A
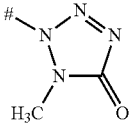
I.1A
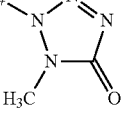
I.2A
| No. | Formula | R¹ | R² | R³ |
|---|---|---|---|---|
| A-1043 | I.1A | SCF$_3$ | 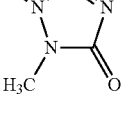 | CHF$_2$ |
| A-1044 | I.1A | SCF$_3$ | 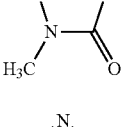 | OCH$_3$ |
| A-1045 | I.1A | SCF$_3$ | 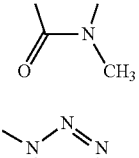 | OCHF$_2$ |
| A-1046 | I.1A | SCF$_3$ | 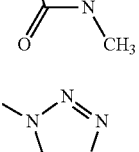 | SCH$_3$ |
| A-1047 | I.1A | SCF$_3$ | 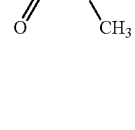 | H |
| A-1048 | I.1A | SCF$_3$ | | CH$_3$ |
| A-1049 | I.1A | SCF$_3$ | | CF$_3$ |

TABLE A-continued
Compounds of the formula I which correspond to the formulae I.1A and I.2A
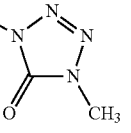
I.1A
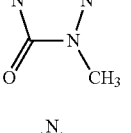
I.2A
| No. | Formula | R¹ | R² | R³ |
|---|---|---|---|---|
| A-1050 | I.1A | SCF$_3$ | 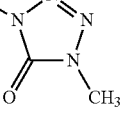 | CHF$_2$ |
| A-1051 | I.1A | SCF$_3$ | 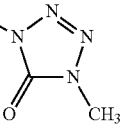 | OCH$_3$ |
| A-1052 | I.1A | SCF$_3$ | 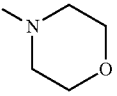 | OCHF$_2$ |
| A-1053 | I.1A | SCF$_3$ | 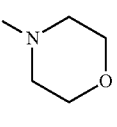 | SCH$_3$ |
| A-1054 | I.1A | SCF$_3$ | 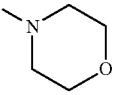 | H |
| A-1055 | I.1A | SCF$_3$ | 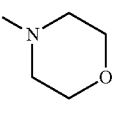 | CH$_3$ |
| A-1056 | I.1A | SCF$_3$ |  | CF$_3$ |
| A-1057 | I.1A | SCF$_3$ |  | CHF$_2$ |

TABLE A-continued

Compounds of the formula I which correspond to the formulae I.1A and I.2A

I.1A

I.2A

| No. | Formula | R¹ | R² | R³ |
|---|---|---|---|---|
| A-1058 | I.1A | SCF$_3$ | #-morpholin-4-yl | OCH$_3$ |
| A-1059 | I.1A | SCF$_3$ | #-morpholin-4-yl | OCHF$_2$ |
| A-1060 | I.1A | SCF$_3$ | #-morpholin-4-yl | SCH$_3$ |
| A-1061 | I.1A | SCF$_3$ | C$_6$H$_5$ | H |
| A-1062 | I.1A | SCF$_3$ | C$_6$H$_5$ | CH$_3$ |
| A-1063 | I.1A | SCF$_3$ | C$_6$H$_5$ | CF$_3$ |
| A-1064 | I.1A | SCF$_3$ | C$_6$H$_5$ | CHF$_2$ |
| A-1065 | I.1A | SCF$_3$ | C$_6$H$_5$ | OCH$_3$ |
| A-1066 | I.1A | SCF$_3$ | C$_6$H$_5$ | OCHF$_2$ |
| A-1067 | I.1A | SCF$_3$ | C$_6$H$_5$ | SCH$_3$ |
| A-1068 | I.1A | SCF$_3$ | 4-F—C$_6$H$_4$ | H |
| A-1069 | I.1A | SCF$_3$ | 4-F—C$_6$H$_4$ | CH$_3$ |
| A-1070 | I.1A | SCF$_3$ | 4-F—C$_6$H$_4$ | CF$_3$ |
| A-1071 | I.1A | SCF$_3$ | 4-F—C$_6$H$_4$ | CHF$_2$ |
| A-1072 | I.1A | SCF$_3$ | 4-F—C$_6$H$_4$ | OCH$_3$ |
| A-1073 | I.1A | SCF$_3$ | 4-F—C$_6$H$_4$ | OCHF$_2$ |
| A-1074 | I.1A | SCF$_3$ | 4-F—C$_6$H$_4$ | SCH$_3$ |
| A-1075 | I.1A | SCF$_3$ | 4-Cl—C$_6$H$_4$ | H |
| A-1076 | I.1A | SCF$_3$ | 4-Cl—C$_6$H$_4$ | CH$_3$ |
| A-1077 | I.1A | SCF$_3$ | 4-Cl—C$_6$H$_4$ | CF$_3$ |
| A-1078 | I.1A | SCF$_3$ | 4-Cl—C$_6$H$_4$ | CHF$_2$ |
| A-1079 | I.1A | SCF$_3$ | 4-Cl—C$_6$H$_4$ | OCH$_3$ |
| A-1080 | I.1A | SCF$_3$ | 4-Cl—C$_6$H$_4$ | OCHF$_2$ |
| A-1081 | I.1A | SCF$_3$ | 4-Cl—C$_6$H$_4$ | SCH$_3$ |
| A-1082 | I.1A | SCF$_3$ | 4-OCH$_3$—C$_6$H$_4$ | H |
| A-1083 | I.1A | SCF$_3$ | 4-OCH$_3$—C$_6$H$_4$ | CH$_3$ |
| A-1084 | I.1A | SCF$_3$ | 4-OCH$_3$—C$_6$H$_4$ | CF$_3$ |
| A-1085 | I.1A | SCF$_3$ | 4-OCH$_3$—C$_6$H$_4$ | CHF$_2$ |
| A-1086 | I.1A | SCF$_3$ | 4-OCH$_3$—C$_6$H$_4$ | OCH$_3$ |
| A-1087 | I.1A | SCF$_3$ | 4-OCH$_3$—C$_6$H$_4$ | OCHF$_2$ |
| A-1088 | I.1A | SCF$_3$ | 4-OCH$_3$—C$_6$H$_4$ | SCH$_3$ |
| A-1089 | I.1A | SCF$_3$ | CH=CH$_2$ | H |
| A-1090 | I.1A | SCF$_3$ | CH=CH$_2$ | CH$_3$ |
| A-1091 | I.1A | SCF$_3$ | CH=CH$_2$ | CH$_3$ |
| A-1092 | I.1A | SCF$_3$ | CH=CH$_2$ | CHF$_2$ |
| A-1093 | I.1A | SCF$_3$ | CH=CH$_2$ | OCH$_3$ |
| A-1094 | I.1A | SCF$_3$ | CH=CH$_2$ | OCHF$_2$ |

TABLE A-continued

Compounds of the formula I which correspond to the formulae I.1A and I.2A

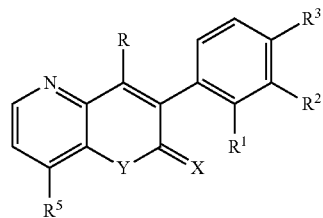

I.1A

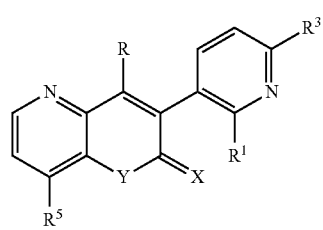

I.2A

| No. | Formula | $R^1$ | $R^2$ | $R^3$ |
|---|---|---|---|---|
| A-1095 | I.1A | $SCF_3$ | $CH=CH_2$ | $SCH_3$ |
| A-1096 | I.1A | $SCF_3$ | $CH=CH-CH_3$ | H |
| A-1097 | I.1A | $SCF_3$ | $CH=CH-CH_3$ | $CH_3$ |
| A-1098 | I.1A | $SCF_3$ | $CH=CH-CH_3$ | $CF_3$ |
| A-1099 | I.1A | $SCF_3$ | $CH=CH-CH_3$ | $CHF_2$ |
| A-1100 | I.1A | $SCF_3$ | $CH=CH-CH_3$ | $OCH_3$ |
| A-1101 | I.1A | $SCF_3$ | $CH=CH-CH_3$ | $OCHF_2$ |
| A-1102 | I.1A | $SCF_3$ | $CH=CH-CH_3$ | $SCH_3$ |
| A-1103 | I.1A | $SCF_3$ | $CH_2CH=CH_2$ | H |
| A-1104 | I.1A | $SCF_3$ | $CH_2CH=CH_2$ | $CH_3$ |
| A-1105 | I.1A | $SCF_3$ | $CH_2CH=CH_2$ | $CF_3$ |
| A-1106 | I.1A | $SCF_3$ | $CH_2CH=CH_2$ | $CHF_2$ |
| A-1107 | I.1A | $SCF_3$ | $CH_2CH=CH_2$ | $OCH_3$ |
| A-1108 | I.1A | $SCF_3$ | $CH_2CH=CH_2$ | $OCHF_2$ |
| A-1109 | I.1A | $SCF_3$ | $CH_2CH=CH_2$ | $SCH_3$ |
| A-1110 | I.1A | $SCF_3$ | $CH_2C\equiv CH$ | H |
| A-1111 | I.1A | $SCF_3$ | $CH_2C\equiv CH$ | $CH_3$ |
| A-1112 | I.1A | $SCF_3$ | $CH_2C\equiv CH$ | $CF_3$ |
| A-1113 | I.1A | $SCF_3$ | $CH_2C\equiv CH$ | $CHF_2$ |
| A-1114 | I.1A | $SCF_3$ | $CH_2C\equiv CH$ | $OCH_3$ |
| A-1115 | I.1A | $SCF_3$ | $CH_2C\equiv CH$ | $OCHF_2$ |
| A-1116 | I.1A | $SCF_3$ | $CH_2C\equiv CH$ | $SCH_3$ |
| A-1117 | I.1A | $SCF_3$ | $CH_2OCH_2CF_3$ | H |
| A-1118 | I.1A | $SCF_3$ | $CH_2OCH_2CF_3$ | $CH_3$ |
| A-1119 | I.1A | $SCF_3$ | $CH_2OCH_2CF_3$ | $CF_3$ |
| A-1120 | I.1A | $SCF_3$ | $CH_2OCH_2CF_3$ | $CHF_2$ |
| A-1121 | I.1A | $SCF_3$ | $CH_2OCH_2CF_3$ | $OCH_3$ |
| A-1122 | I.1A | $SCF_3$ | $CH_2OCH_2CF_3$ | $OCHF_2$ |
| A-1123 | I.1A | $SCF_3$ | $CH_2OCH_2CF_3$ | $SCH_3$ |
| A-1124 | I.1A | $SCF_3$ | ![tetrahydrofuranylmethoxymethyl] | H |
| A-1125 | I.1A | $SCF_3$ | ![tetrahydrofuranylmethoxymethyl] | $CH_3$ |
| A-1126 | I.1A | $SCF_3$ | ![tetrahydrofuranylmethoxymethyl] | $CF_3$ |
| A-1127 | I.1A | $SCF_3$ | ![tetrahydrofuranylmethoxymethyl] | $CHF_2$ |

TABLE A-continued

Compounds of the formula I which correspond to the formulae I.1A and I.2A

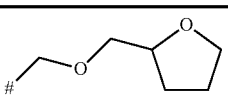

I.1A

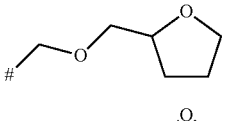

I.2A

| No. | Formula | R¹ | R² | R³ |
|---|---|---|---|---|
| A-1128 | I.1A | SCF$_3$ | 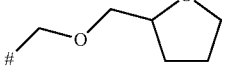 | OCH$_3$ |
| A-1129 | I.1A | SCF$_3$ | (same as above) | OCHF$_2$ |
| A-1130 | I.1A | SCF$_3$ | (same as above) | SCH$_3$ |
| A-1131 | I.1A | SCF$_3$ | OCH$_2$CH$_3$ | H |
| A-1132 | I.1A | SCF$_3$ | OCH$_2$CH$_3$ | CH$_3$ |
| A-1133 | I.1A | SCF$_3$ | OCH$_2$CH$_3$ | CF$_3$ |
| A-1134 | I.1A | SCF$_3$ | OCH$_2$CH$_3$ | CHF$_2$ |
| A-1135 | I.1A | SCF$_3$ | OCH$_2$CH$_3$ | OCH$_3$ |
| A-1136 | I.1A | SCF$_3$ | OCH$_2$CH$_3$ | OCHF$_2$ |
| A-1137 | I.1A | SCF$_3$ | OCH$_2$CH$_3$ | SCH$_3$ |
| A-1138 | I.1A | SCF$_3$ | OCH$_2$CH$_2$OCH$_3$ | H |
| A-1139 | I.1A | SCF$_3$ | OCH$_2$CH$_2$OCH$_3$ | CH$_3$ |
| A-1140 | I.1A | SCF$_3$ | OCH$_2$CH$_2$OCH$_3$ | CF$_3$ |
| A-1141 | I.1A | SCF$_3$ | OCH$_2$CH$_2$OCH$_3$ | CHF$_2$ |
| A-1142 | I.1A | SCF$_3$ | OCH$_2$CH$_2$OCH$_3$ | OCH$_3$ |
| A-1143 | I.1A | SCF$_3$ | OCH$_2$CH$_2$OCH$_3$ | OCHF$_2$ |
| A-1144 | I.1A | SCF$_3$ | OCH$_2$CH$_2$OCH$_3$ | SCH$_3$ |
| A-1145 | I.1A | SCF$_3$ | SO$_2$CH$_3$ | H |
| A-1146 | I.1A | SCF$_3$ | SO$_2$CH$_3$ | CH$_3$ |
| A-1147 | I.1A | SCF$_3$ | SO$_2$CH$_3$ | CF$_3$ |
| A-1148 | I.1A | SCF$_3$ | SO$_2$CH$_3$ | CHF$_2$ |
| A-1149 | I.1A | SCF$_3$ | SO$_2$CH$_3$ | OCH$_3$ |
| A-1150 | I.1A | SCF$_3$ | SO$_2$CH$_3$ | OCHF$_2$ |
| A-1151 | I.1A | SCF$_3$ | SO$_2$CH$_3$ | SCH$_3$ |
| A-1152 | I.1A | SCF$_3$ | SO$_2$CH$_2$CH$_3$ | H |
| A-1153 | I.1A | SCF$_3$ | SO$_2$CH$_2$CH$_3$ | CH$_3$ |
| A-1154 | I.1A | SCF$_3$ | SO$_2$CH$_2$CH$_3$ | CF$_3$ |
| A-1155 | I.1A | SCF$_3$ | SO$_2$CH$_2$CH$_3$ | CHF$_2$ |
| A-1156 | I.1A | SCF$_3$ | SO$_2$CH$_2$CH$_3$ | OCH$_3$ |
| A-1157 | I.1A | SCF$_3$ | SO$_2$CH$_2$CH$_3$ | OCHF$_2$ |
| A-1158 | I.1A | SCF$_3$ | SO$_2$CH$_2$CH$_3$ | SCH$_3$ |
| A-1159 | I.1A | SCF$_3$ | SO$_2$CH(CH$_3$)$_2$ | H |
| A-1160 | I.1A | SCF$_3$ | SO$_2$CH(CH$_3$)$_2$ | CH$_3$ |
| A-1161 | I.1A | SCF$_3$ | SO$_2$CH(CH$_3$)$_2$ | CF$_3$ |
| A-1162 | I.1A | SCF$_3$ | SO$_2$CH(CH$_3$)$_2$ | CHF$_2$ |
| A-1163 | I.1A | SCF$_3$ | SO$_2$CH(CH$_3$)$_2$ | OCH$_3$ |
| A-1164 | I.1A | SCF$_3$ | SO$_2$CH(CH$_3$)$_2$ | OCHF$_2$ |
| A-1165 | I.1A | SCF$_3$ | SO$_2$CH(CH$_3$)$_2$ | SCH$_3$ |
| A-1166 | I.1A | SCF$_3$ | COOCH$_3$ | H |
| A-1167 | I.1A | SCF$_3$ | COOCH$_3$ | CH$_3$ |

TABLE A-continued

Compounds of the formula I which correspond to the formulae I.1A and I.2A

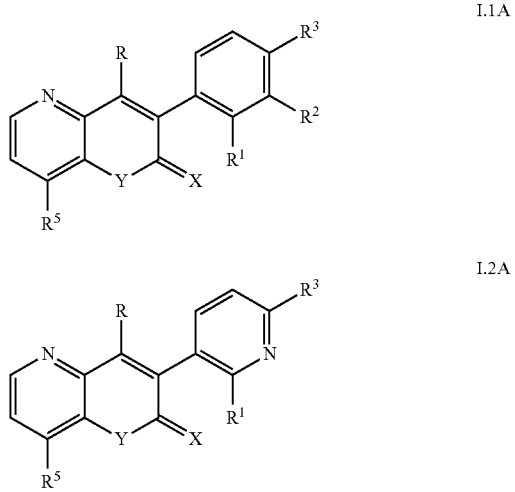

I.1A

I.2A

| No. | Formula | $R^1$ | $R^2$ | $R^3$ |
|---|---|---|---|---|
| A-1168 | I.1A | $SCF_3$ | $COOCH_3$ | $CF_3$ |
| A-1169 | I.1A | $SCF_3$ | $COOCH_3$ | $CHF_2$ |
| A-1170 | I.1A | $SCF_3$ | $COOCH_3$ | $OCH_3$ |
| A-1171 | I.1A | $SCF_3$ | $COOCH_3$ | $OCHF_2$ |
| A-1172 | I.1A | $SCF_3$ | $COOCH_3$ | $SCH_3$ |
| A-1173 | I.1A | $SCF_3$ | $COOCH_2CH_3$ | H |
| A-1174 | I.1A | $SCF_3$ | $COOCH_2CH_3$ | $CH_3$ |
| A-1175 | I.1A | $SCF_3$ | $COOCH_2CH_3$ | $CF_3$ |
| A-1176 | I.1A | $SCF_3$ | $COOCH_2CH_3$ | $CHF_2$ |
| A-1177 | I.1A | $SCF_3$ | $COOCH_2CH_3$ | $OCH_3$ |
| A-1178 | I.1A | $SCF_3$ | $COOCH_2CH_3$ | $OCHF_2$ |
| A-1179 | I.1A | $SCF_3$ | $COOCH_2CH_3$ | $SCH_3$ |
| A-1180 | I.1A | $SCF_3$ | $\#^2$—$CH_2CH_2SO_2$—$\#^3$ | |
| A-1181 | I.1A | $SCF_3$ | $\#^2$—$CH(CH_3)CH_2SO_2$—$\#^3$ | |
| A-1182 | I.1A | $SCF_3$ | $\#^2$—$C(CH_3)_2CH_2SO_2$—$\#^3$ | |
| A-1183 | I.1A | $SCF_3$ | $\#^2$—$SO_2CH_2CH_2SO_2$—$\#^3$ | |
| A-1184 | I.1A | $SCF_3$ | $\#^2$—$CH(OCH_2CH_2F)CH_2CH_2SO_2$—$\#^3$ | |
| A-1185 | I.1A | $SCF_3$ | $\#^2$—$C(=NOCH_3)CH_2CH_2SO_2$—$\#^3$ | |
| A-1186 | I.1A | $SCF_3$ | $\#^2$—$SO_2CH_2CH_2C(CH_3)_2$—$\#^3$ | |
| A-1187 | I.1A | $SCF_3$ | $\#^2$—$N(CH_3)C(=O)S$—$\#^3$ | |
| A-1188 | I.1A | $SCF_3$ | $\#^2$—$C(=)N(CH_3)SO_2$—$\#^3$ | |
| A-1189 | I.2A | $CH_2OCH_2CH_2OCH_3$ | — | $CF_3$ |
| A-1190 | I.1A | $\#^1$—CH=CH—CH=N—$\#^2$ | | F |
| A-1191 | I.1A | $\#^1$—CH=CH—CH=N—$\#^2$ | | Cl |
| A-1192 | I.1A | $\#^1$—CH=CH—CH=N—$\#^2$ | | $CF_3$ |

$\#^1$ characterizes the bond in position 2 (group $R^1$)
$\#^2$ characterizes the bond in position 3 (group $R^2$)
$\#^3$ characterizes the bond in position 4 (group $R^3$)

TABLE A.1

Also especially preferred are compounds A.1-1, A.1-8, A.1-15, A.1-22, A.1-29, A.1-36, A.1-43, A.1-50, A.1-57, A.1-64, A.1-71, A.1-78, A.1-85, A.1-92, A.1-99, A.1-106, A.1-113, A.1-120, A.1-127, A.1-134, A.1-141, A.1-148, A.1-155, A.1-162, A.1-169, A.1-176, A.1-183, A.1-199, A.1-206, A.1-213, A.1-220, A.1-227, A.1-234, A.1-241, A.1-248, A.1-255, A.1-262, A.1-269, A.1-276, A.1-283, A.1-290, A.1-297, A.1-304, A.1-311, A.1-318, A.1-325, A.1-332, A.1-339, A.1-346, A.1-353, A.1-360, A.1-367, A.1-374, A.1-381, A.1-397, A.1-404, A.1-411, A.1-418, A.1-425, A.1-432, A.1-439, A.1-446, A.1-453, A.1-460, A.1-467, A.1-474, A.1-481, A.1-488, A.1-495, A.1-502, A.1-509, A.1-516, A.1-523, A.1-530, A.1-537, A.1-544, A.1-551, A.1-558, A.1-565, A.1-572, A.1-579, A.1-595, A.1-602, A.1-609, A.1-616, A.1-623, A.1-630, A.1-637, A.1-644, A.1-651, A.1-658, A.1-665, A.1-672, A.1-679, A.1-686, A.1-693, A.1-700, A.1-707, A.1-714, A.1-721, A.1-728, A.1-735, A.1-742, A.1-749, A.1-756, A.1-763, A.1-770, A.1-777, A.1-793, A.1-800, A.1-807, A.1-814, A.1-821, A.1-828, A.1-835, A.1-842, A.1-849, A.1-856, A.1-863, A.1-870, A.1-877, A.1-884, A.1-891, A.1-898, A.1-905, A.1-912, A.1-919, A.1-926, A.1-933, A.1-940, A.1-947, A.1-954, A.1-961, A.1-968, A.1-975, A.1-991, A.1-998, A.1-1005, A.1-1012, A.1-1019, A.1-1026, A.1-1033, A.1-1040, A.1-1047, A.1-1054, A.1-1061, A.1-1068, A.1-1075, A.1-1082, A.1-1089, A.1-1096, A.1-1103, A.1-1110, A.1-1117, A.1-1124, A.1-1131, A.1-1138, A.1-1145, A.1-1152, A.1-1159, A.1-1166 and A.1-1173 which differ from the corresponding compounds A-1, A-8, A-15, A-22, A-29, A-36, A-43, A-50, A-57, A-64, A-71, A-78, A-85, A-92, A-99, A-106, A-113, A-120, A-127, A-134, A-141, A-148, A-155, A-162, A-169, A-176, A-183, A-199, A-206, A-213, A-220, A-227, A-234, A-241, A-248, A-255, A-262, A-269, A-276, A-283, A-290, A-297, A-304, A-311, A-318, A-325, A-332, A-339, A-346, A-353, A-360, A-367, A-374, A-381, A-397, A-404, A-411, A-418, A-425, A-432, A-439, A-446, A-453, A-460, A-467, A-474, A-481, A-488, A-495, A-502, A-509, A-516, A-523, A-530, A-537, A-544, A-551, A-558, A-565, A-572, A-579, A-595, A-602, A-609, A-616, A-623, A-630, A-637, A-644, A-651, A-658, A-665, A-672, A-679, A-686, A-693, A-700, A-707, A-714, A-721, A-728, A-735, A-742, A-749, A-756, A-763, A-770, A-777, A-793, A-800, A-807, A-814, A-821, A-828, A-835, A-842, A-849, A-856, A-863, A-870, A-877, A-884, A-891, A-898, A-905, A-912, A-919, A-926, A-933, A-940, A-947, A-954, A-961, A-968, A-975, A-991, A-998, A-1005, A-1012, A-1019, A-1026, A-1033, A-1040,

TABLE A.1-continued

A-1047, A-1054, A-1061, A-1068, A-1075, A-1082, A-1089, A-1096, A-1103, A-1110, A-1117, A-1124, A-1131, A-1138, A-1145, A-1152, A-1159, A-1166 and A-1173 only in that $R^3$ is F.

TABLE A.2

Also especially preferred are compounds A.2-1, A.2-8, A.2-15, A.2-22, A.2-29, A.2-36, A.2-43, A.2-50, A.2-57, A.2-64, A.2-71, A.2-78, A.2-85, A.2-92, A.2-99, A.2-106, A.2-113, A.2-120, A.2-127, A.2-134, A.2-141, A.2-148, A.2-155, A.2-162, A.2-169, A.2-176, A.2-183, A.2-199, A.2-206, A.2-213, A.2-220, A.2-227, A.2-234, A.2-241, A.2-248, A.2-255, A.2-262, A.2-269, A.2-276, A.2-283, A.2-290, A.2-297, A.2-304, A.2-311, A.2-318, A.2-325, A.2-332, A.2-339, A.2-346, A.2-353, A.2-360, A.2-367, A.2-374, A.2-381, A.2-397, A.2-404, A.2-411, A.2-418, A.2-425, A.2-432, A.2-439, A.2-446, A.2-453, A.2-460, A.2-467, A.2-474, A.2-481, A.2-488, A.2-495, A.2-502, A.2-509, A.2-516, A.2-523, A.2-530, A.2-537, A.2-544, A.2-551, A.2-558, A.2-565, A.2-572, A.2-579, A.2-595, A.2-602, A.2-609, A.2-616, A.2-623, A.2-630, A.2-637, A.2-644, A.2-651, A.2-658, A.2-665, A.2-672, A.2-679, A.2-679, A.2-686, A.2-693, A.2-700, A.2-707, A.2-714, A.2-721, A.2-728, A.2-735, A.2-742, A.2-749, A.2-756, A.2-763, A.2-770, A.2-777, A.2-793, A.2-800, A.2-807, A.2-814, A.2-821, A.2-828, A.2-835, A.2-842, A.2-849, A.2-856, A.2-863, A.2-870, A.2-877, A.2-884, A.2-891, A.2-898, A.2-905, A.2-912, A.2-919, A.2-926, A.2-933, A.2-940, A.2-947, A.2-954, A.2-961, A.2-968, A.2-975, A.2-991, A.2-998, A.2-1005, A.2-1012, A.2-1019, A.2-1026, A.2-1033, A.2-1040, A.2-1047, A.2-1054, A.2-1061, A.2-1068, A.2-1075, A.2-1082, A.2-1089, A.2-1096, A.2-1103, A.2-1110, A.2-1117, A.2-1124, A.2-1131, A.2-1138, A.2-1145, A.2-1152, A.2-1159, A.2-1166 and A.2-1173 which differ from the corresponding compounds A-1, A-8, A-15, A-22, A-29, A-36, A-43, A-50, A-57, A-64, A-71, A-78, A-85, A-92, A-99, A-106, A-113, A-120, A-127, A-134, A-141, A-148, A-155, A-162, A-169, A-176, A-183, A-199, A-206, A-213, A-220, A-227, A-234, A-241, A-248, A-255, A-262, A-269, A-276, A-283, A-290, A-297, A-304, A-311, A-318, A-325, A-332, A-339, A-346, A-353, A-360, A-367, A-374, A-381, A-397, A-404, A-411, A-418, A-425, A-432, A-439, A-446, A-453, A-460, A-467, A-474, A-481, A-488, A-495, A-502, A-509, A-516, A-523, A-530, A-537, A-544, A-551, A-558, A-565, A-572, A-579, A-595, A-602, A-609, A-616, A-623, A-630, A-637, A-644, A-651, A-658, A-665, A-672, A-679, A-679, A-686, A-693, A-700, A-707, A-714, A-721, A-728, A-735, A-742, A-749, A-756, A-763, A-770, A-777, A-793, A-800, A-807, A-814, A-821, A-828, A-835, A-842, A-849, A-856, A-863, A-870, A-877, A-884, A-891, A-898, A-905, A-912, A-919, A-926, A-933, A-940, A-947, A-954, A-961, A-968, A-975, A-991, A-998, A-1005, A-1012, A-1019, A-1026, A-1033, A-1040, A-1047, A-1054, A-1061, A-1068, A-1075, A-1082, A-1089, A-1096, A-1103, A-1110, A-1117, A-1124, A-1131, A-1138, A-1145, A-1152, A-1159, A-1166 and A-1173 only in that $R^3$ is Cl.

The compounds I and their agriculturally useful salts are suitable, both as isomer mixtures and in the form of the pure isomers, as herbicides. They are suitable as such or as an appropriately formulated composition. The herbicidal compositions comprising the compound I, in particular the preferred aspects thereof, control vegetation on non-crop areas very efficiently, especially at high rates of application. They act against broad-leaved weeds and weed grasses in crops such as wheat, rice, corn, soybeans and cotton without causing any significant damage to the crop plants. This effect is mainly observed at low rates of application.

Depending on the application method in question, the compounds I, in particular the preferred aspects thereof, or compositions comprising them can additionally be employed in a further number of crop plants for eliminating unwanted plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*S. vulgare*), *Theobroma cacao, Trifolium pratense, Triticum aestivum, Triticale, Triticum durum, Vicia faba, Vitis vinifera, Zea mays.*

The term "crop plants" also includes plants which have been modified by breeding, mutagenesis or genetic engineering. Genetically modified plants are plants whose genetic material has been modified in a manner which does not occur under natural conditions by crossing, mutations or natural recombination (i.e. reassembly of the genetic information). Here, in general, one or more genes are integrated into the genetic material of the plant to improve the properties of the plant.

Accordingly, the term "crop plants" also includes plants which, by breeding and genetic engineering, have acquired tolerance to certain classes of herbicides, such as hydroxyphenylpyruvate dioxygenase (HPPD) inhibitors, acetolactate synthase (ALS) inhibitors, such as, for example, sulfonylureas (EP-A 257 993, U.S. Pat. No. 5,013,659) or imidazolinones (see, for example, U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), enolpyruvylshikimate 3-phosphate synthase (EPSPS) inhibitors, such as, for example, glyphosate (see, for example, WO 92/00377), glutamine synthetase (GS) inhibitors, such as, for example, glufosinate (see, for example, EP-A 242 236, EP-A 242 246), or oxynil herbicides (see, for example, U.S. Pat. No. 5,559,024).

Numerous crop plants, for example Clearfield® oilseed rape, tolerant to imidazolinones, for example imazamox, have been generated with the aid of classic breeding methods (mutagenesis). Crop plants such as soybeans, cotton, corn, beet and oilseed rape, resistant to glyphosate or glufosinate, which are available under the tradenames RoundupReady® (glyphosate) and Liberty Link® (glufosinate) have been generated with the aid of genetic engineering methods.

Accordingly, the term "crop plants" also includes plants which, with the aid of genetic engineering, produce one or more toxins, for example those of the bacterial strain *Bacillus* ssp. Toxins which are produced by such genetically modified plants include, for example, insecticidal proteins of *Bacillus* spp., in particular *B. thuringiensis*, such as the endotoxins CryIAb, CryIAc, CryIF, CryIFa2, Cry2Ab, Cry3A, Cry3Bb1, Cry9c, Cry34Ab1 or Cry35Ab1; or vegetative insecticidal proteins (VIPs), for example VIP1, VIP2, VIP3, or VIP3A; insecticidal proteins of nematode-colonizing bacteria, for example *Photorhabdus* spp. or *Xenorhabdus* spp.; toxins of animal organisms, for example wasp, spider or scorpion toxins; fungal toxins, for example from Streptomycetes; plant lectins, for example from peas or barley; agglutinins; proteinase inhibitors, for example trypsin inhibitors, serine protease inhibitors, patatin, cystatin or papain inhibitors, ribosome-inactivating proteins (RIPs), for example ricin, corn-RIP, abrin, luffin, saporin or bryodin; steroid-metabolizing enzymes, for example 3-hydroxysteroid oxidase, ecdysteroid-IDP glycosyl transferase, cholesterol oxidase, ecdysone inhibitors, or HMG-CoA reductase; ion channel blockers, for example inhibitors of sodium channels or calcium channels; juvenile hormone esterase; receptors of the diuretic hormone (helicokinin receptors); stilbene synthase, bibenzyl synthase, chitinases and glucanases. In the plants, these toxins may also be produced as pretoxins, hybrid proteins or truncated or otherwise modified proteins. Hybrid proteins are characterized by a novel combination of different protein domains (see, for example, WO 2002/015701). Further examples of such toxins or genetically modified plants which produce these toxins are disclosed in EP-A 374 753, WO 93/007278, WO 95/34656, EP-A 427 529, EP-A 451 878, WO 03/018810 and WO 03/052073. The methods for producing these genetically modified plants are known to the person skilled in the art and disclosed, for example, in the publications mentioned above. Numerous of the toxins mentioned above bestow, upon the plants by which they are produced, tolerance to pests from all taxonomic classes of arthropods, in particular to beetles (Coeleropta), dipterans (Diptera) and butterflies (Lepidoptera) and to nematodes (Nematoda).

Genetically modified plants which produce one or more genes coding for insecticidal toxins are described, for example, in the publications mentioned above, and some of them are commercially available, such as, for example, YieldGard® (corn varieties producing the toxin Cry1Ab), YieldGard® Plus (corn varieties which produce the toxins Cry1Ab and Cry3Bb1), Starlink® (corn varieties which produce the toxin Cry9c), Herculex® RW (corn varieties which produce the toxins Cry34Ab1, Cry35Ab1 and the enzyme phosphinothricin-N-acetyltransferase [PAT]); NuCOTN® 33B (cotton varieties which produce the toxin Cry1Ac), Bollgard® I (cotton varieties which produce the toxin Cry1Ac), Bollgard® II (cotton varieties which produce the toxins Cry1Ac and Cry2Ab2); VIPCOT® (cotton varieties which produce a VIP toxin); NewLeaf® (potato varieties which produce the toxin Cry3A); Bt-Xtra®, NatureGard®, KnockOut®, BiteGard®, Protecta®, Bt11 (for example Agrisure® CB) and Bt176 from Syngenta Seeds SAS, France (corn varieties which produce the toxin Cry1Ab and the PAT enyzme), MIR604 from Syngenta Seeds SAS, France (corn varieties which produce a modified version of the toxin Cry3A, see WO 03/018810), MON 863 from Monsanto Europe S.A., Belgium (corn varieties which produce the toxin Cry3Bb1), IPC 531 from Monsanto Europe S.A., Belgium (cotton varieties which produce a modified version of the toxin Cry1Ac) and 1507 from Pioneer Overseas Corporation, Belgium (corn varieties which produce the toxin Cry1F and the PAT enzyme).

Accordingly, the term "crop plants" also includes plants which, with the aid of genetic engineering, produce one or more proteins which are more robust or have increased resistance to bacterial, viral or fungal pathogens, such as, for example, pathogenesis-related proteins (PR proteins, see EP-A 392 225), resistance proteins (for example potato varieties producing two resistance genes against *Phytophthora infestans* from the wild Mexican potato *Solanum bulbocastanum*) or T4 lysozyme (for example potato cultivars which, by producing this protein, are resistant to bacteria such as *Erwinia amylvora*).

Accordingly, the term "crop plants" also includes plants whose productivity has been improved with the aid of genetic engineering methods, for example by enhancing the potential yield (for example biomass, grain yield, starch, oil or protein content), tolerance to drought, salt or other limiting environmental factors or resistance to pests and fungal, bacterial and viral pathogens.

The term "crop plants" also includes plants whose ingredients have been modified with the aid of genetic engineering methods in particular for improving human or animal diet, for example by oil plants producing health-promoting long-chain omega 3 fatty acids or monounsaturated omega 9 fatty acids (for example Nexera® oilseed rape).

The term "crop plants" also includes plants which have been modified with the aid of genetic engineering methods for improving the production of raw materials, for example by increasing the amylopectin content of potatoes (Amflora® potato).

Furthermore, it has been found that the compounds of the formula I are also suitable for the defoliation and/or desiccation of plant parts, for which crop plants such as cotton, potato, oilseed rape, sunflower, soybean or field beans, in particular cotton, are suitable. In this regard, there have been found compositions for the desiccation and/or defoliation of plants, processes for preparing these compositions and methods for desiccating and/or defoliating plants using the compounds of the formula I.

As desiccants, the compounds of the formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the readily controllable defoliation of useful plants, in particular cotton.

Moreover, a shortening of the time interval in which the individual cotton plants mature leads to an increased fiber quality after harvesting.

The compounds I, or the herbicidal compositions comprising the compounds I, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in each case, they should ensure the finest possible distribution of the active ingredients according to the invention.

The herbicidal compositions comprise a herbicidally effective amount of at least one compound of the formula I or an agriculturally useful salt of I, and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, if appropriate colorants and, for seed formulations, adhesives.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulation. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following:

mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate andureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Powders, materials for broadcasting and dusts can be prepared by mixing or grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water. To prepare emulsions, pastes or oil dispersions, the compounds of the formula I or Ia, either as such or dissolved in an oil or solvent, can be homogenized in water by means of a wetting agent, tackifier, dispersant or emulsifier. Alternatively, it is also possible to prepare concentrates comprising active substance, wetting agent, tackifier, dispersant or emulsifier and, if desired, solvent or oil, which are suitable for dilution with water.

The concentrations of the compounds of the formula I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to NMR spectrum).

The formulations or ready-to-use preparations may also comprise acids, bases or buffer systems, suitable examples being phosphoric acid or sulfuric acid, or urea or ammonia.

The compounds I of the invention can for example be formulated as follows:

1. Products for Dilution with Water

A Water-soluble concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable concentrates 15 parts by weight of active compound are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (e.g. alkylaromatics) with addition of calcium dodecylbenzenesulfonate and castor oil ethoxylate (in each case 5 parts by weight). This mixture is introduced into 30 parts by weight of water by means of an emulsifier (e.g. Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetters and 70 parts by weight of water or an organic solvent to give a fine active compound suspension.

Dilution with water gives a stable suspension of the active compound. The active compound content in the formulation is 20% by weight.

F Water-dispersible granules and water-soluble granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-dispersible powders and water-soluble powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H Gel formulations

In a ball mill, 20 parts by weight of active compound, 10 parts by weight of dispersant, 1 part by weight of gelling agent and 70 parts by weight of water or of an organic solvent are ground to give a fine suspension. Dilution with water gives a stable suspension with active compound content of 20% by weight.

2. Products to be Applied Undiluted

I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV solutions (UL)

10 parts by weight of active compound are dissolved in 90 parts by weight of an organic solvent, for example xylene. This gives a product to be applied undiluted with an active compound content of 10% by weight.

The compounds I or the herbicidal compositions comprising them can be applied pre- or post-emergence, or together with the seed of a crop plant. It is also possible to apply the herbicidal compositions or active compounds by applying seed, pretreated with the herbicidal compositions or active compounds, of a crop plant. If the active compounds are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

In a further embodiment, the compounds of the formula I or the herbicidal compositions can be applied by treating seed.

The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the compounds of the formula I according to the invention or the compositions prepared therefrom. Here, the herbicidal compositions can be applied diluted or undiluted.

The term seed comprises seed of all types, such as, for example, corns, seeds, fruits, tubers, cuttings and similar forms. Here, preferably, the term seed describes corns and seeds.

The seed used can be seed of the useful plants mentioned above, but also the seed of transgenic plants or plants obtained by customary breeding methods.

The rates of application of active compound are from 0.001 to 3.0, preferably 0.01 to 1.0, kg/ha of active substance (a.s.), depending on the control target, the season, the target plants and the growth stage. To treat the seed, the compounds I are generally employed in amounts of from 0.001 to 10 kg per 100 kg of seed.

It may also be advantageous to use the compounds of the formula I in combination with safeners. Safeners are chemical compounds which prevent or reduce damage to useful plants without substantially affecting the herbicidal action of the compounds of the formula I on unwanted plants. They can be used both before sowing (for example in the treatment of seed, or on cuttings or seedlings) and before or after the emergence of the useful plant. The safeners and the compounds of the formula I can be used simultaneously or in succession. Suitable safeners are, for example, (quinolin-8-oxy)acetic acids, 1-phenyl-5-haloalkyl-1H-1,2,4-triazole-3-carboxylic acids, 1-phenyl-4,5-dihydro-5-alkyl-1H-pyrazole-3,5-dicarboxylic acids, 4,5-dihydro-5,5-diaryl-3-isoxazolecarboxylic acids, dichloroacetamides, alpha-oximinophenylacetonitriles, acetophenone oximes, 4,6-dihalo-2-phenylpyrimidines, N-[[4-(aminocarbonyl)phenyl]sulfonyl]-2-benzamides, 1,8-naphthalic anhydride, 2-halo-4-(haloalkyl)-5-thiazolecarboxylic acids, phosphorothiolates and O-phenyl N-alkylcarbamates and their agriculturally useful salts and, provided that they have an acid function, their agriculturally useful derivatives, such as amides, esters and thioesters.

To broaden the activity spectrum and to obtain synergistic effects, the compounds of the formula I can be mixed and jointly applied with numerous representatives of other herbicidal or growth-regulating groups of active compounds or with safeners. Suitable mixing partners are, for example, 1,2,4-thiadiazoles, 1,3,4-thiadiazoles, amides, aminophosphoric acid and its derivatives, aminotriazoles, anilides, aryloxy/heteroaryloxyalkanoic acids and their derivatives, benzoic acid and its derivatives, benzothiadiazinones, 2-(hetaroyl/aroyl)-1,3-cyclohexanediones, heteroaryl aryl ketones, benzylisoxazolidinones, meta-CF$_3$-phenyl derivatives, carbamates, quinoline carboxylic acid and its derivatives, chloroacetanilides, cyclohexenone oxime ether derivates, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils and also phenylpyrazolines and isoxazolines and their derivatives.

Moreover, it may be useful to apply the compounds I alone or in combination with other herbicides or else also mixed with further crop protection agents, jointly, for example with compositions for controlling pests or phytopathogenic fungi or bacteria. Also of interest is the miscibility with mineral salt solutions which are employed for alleviating nutritional and trace element deficiencies. Other additives such as nonphytotoxic oils and oil concentrates may also be added.

Examples of herbicides which can be used in combination with the pyridine compounds of the formula I according to the present invention are:

b1) from the group of the lipid biosynthesis inhibitors:

alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

amidosulfuron, azimsulfuron, bensulfuron, bensulfuron-methyl, bispyribac, bispyribac-sodium, chlorimuron, chlorimuron-ethyl, chlorsulfuron, cinosulfuron, cloransulam, cloransulam-methyl, cyclosulfamuron, diclosulam, ethametsulfuron, ethametsulfuron-methyl, ethoxysulfuron, flazasulfuron, florasulam, flucarbazone, flucarbazone-sodium, flucetosulfuron, flumetsulam, flupyrsulfuron, flupyrsulfuron-methyl-sodium, foramsulfuron, halosulfuron, halosulfuron-methyl, imazamethabenz, imazamethabenz-methyl, imazamox, imazapic, imazapyr, imazaquin, imazethapyr, imazosulfuron, iodosulfuron, iodosulfuron-methyl-sodium, mesosulfuron, metosulam, metsulfuron, metsulfuron-methyl, nicosulfuron, orthosulfamuron, oxasulfuron, penoxsulam, primisulfuron, primisulfuron-methyl, propoxycarbazone, propoxycarbazone-sodium, prosulfuron, pyrazosulfuron, pyrazosulfuron-ethyl, pyribenzoxim, pyrimisulfan, pyriftalid, pyriminobac, pyriminobac-methyl, pyrithiobac, pyrithiobac-sodium, pyroxsulam, rimsulfuron, sulfometuron, sulfometuron-methyl, sulfosulfuron, thiencarbazone, thiencarbazone-methyl, thifensulfuron, thifensulfuron-methyl, triasulfuron, tribenuron, tribenuron-methyl, trifloxysulfuron, triflusulfuron, triflusulfuron-methyl and tritosulfuron;

b3) from the group of the photosynthesis inhibitors:

ametryn, amicarbazone, atrazine, bentazon, bentazone-sodium, bromacil, bromofenoxim, bromoxynil and its salts and esters, chlorobromuron, chloridazone, chlorotoluron, chloroxuron, cyanazine, desmedipham, desmetryn, dimefuron, dimethametryn, diquat, diquat-dibromide, diuron, fluometuron, hexazinone, ioxynil and its salts and esters, isoproturon, isouron, karbutilate, lenacil, linuron, metamitron, methabenzthiazuron, metobenzuron, metoxuron, metribuzin, monolinuron, neburon, paraquat, paraquat-dichloride, paraquat-dimetilsulfate, pentanochlor, phenmedipham, phenmedipham-ethyl, prometon, prometryn, propanil, propazine, pyridafol, pyridate, siduron, simazine, simetryn, tebuthiuron, terbacil, terbumeton, terbuthylazine, terbutryn, thidiazuron and trietazine;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, 2-chloro-5-[3,6-dihydro-3-methyl-2,6-dioxo-4-(trifluoromethyl)-1(2H)-pyrimidinyl]-4-fluoro-N-[(isopropyl)methylsulfamoyl]benzamide (H-1; CAS 372137-35-4), ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (H-2; CAS 353292-31-6), N-ethyl-3-(2,6-dichloro-4-trifluoromethylphenoxy)-5-methyl-1H-pyrazole-1-carboxamide (H-3; CAS 452098-92-9), N-tetrahydrofurfuryl-3-(2,6-dichloro-4-trifluoromethylphenoxy)-5-methyl-1H-pyrazole-1-carboxamide (H-4; CAS 915396-43-9), N-ethyl-3-(2-chloro-6-fluoro-4-trifluoromethylphenoxy)-5-methyl-1H-pyrazole-1-carboxamide (H-5; CAS 452099-05-7), N-tetrahydrofurfuryl-3-(2-chloro-6-fluoro-4-trifluoromethylphenoxy)-5-methyl-1 Hpyrazole-1-carboxamide (H-6; CAS 45100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

b5) from the group of the bleacher herbicides:

aclonifen, amitrol, beflubutamid, benzobicyclon, benzofenap, clomazone, diflufenican, fluridone, fluorochloridone, flurtamone, isoxaflutole, mesotrione, norflurazon, picolinafen, pyrasulfutole, pyrazolynate, pyrazoxyfen, sulcotrione, tefuryltrione, tembotrione, topramezone, 4-hydroxy-3-[[2-[(2-methoxyethoxy)methyl]-6-(trifluoromethyl)-3-pyridyl]carbonyl]bicyclo-[3.2.1]oct-3-en-2-one (H-7; CAS 352010-68-5) and 4-(3-trifluoromethylphenoxy)-2-(4-trifluoromethylphenyl)pyrimidine (H-8; CAS180608-33-7);

b6) from the group of the EPSP synthase inhibitors:

glyphosate, glyphosate-isopropylammonium and glyphosate-trimesium (sulfosate);

b7) from the group of the glutamine synthase inhibitors:

bilanaphos (bialaphos), bilanaphos-sodium, glufosinate and glufosinate-ammonium;

b8) from the group of the DHP synthase inhibitors:

asulam;

b9) from the group of the mitose inhibitors:

amiprophos, amiprophos-methyl, benfluralin, butamiphos, butralin, carbetamide, chlorpropham, chlorthal, chlorthal-dimethyl, dinitramine, dithiopyr, ethalfluralin, fluchloralin, oryzalin, pendimethalin, prodiamine, propham, propyzamide, tebutam, thiazopyr and trifluralin;

b10) from the group of the VLCFA inhibitors:

acetochlor, alachlor, anilofos, butachlor, cafenstrole, dimethachlor, dimethanamid, dimethenamid-P, diphenamid, fentrazamide, flufenacet, mefenacet, metazachlor, metolachlor, metolachlor-S, naproanilide, napropamide, pethoxamid, piperophos, pretilachlor, propachlor, propisochlor, pyroxasulfone (KIH-485) and thenylchlor;

Compounds of the formula 2:

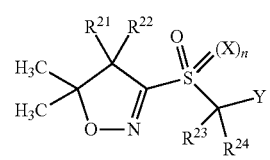

2 in which the variables have the following meanings:

Y is phenyl or 5- or 6-membered heteroaryl as defined at the outset, which radicals may be substituted by one to three groups $R^{aa}$; $R^{21}, R^{22}, R^{23}, R^{24}$ are H, halogen or $C_1$-$C_4$-alkyl; X is O or NH; N is 0 or 1.

Compounds of the formula 2 have in particular the following meanings:
Y is

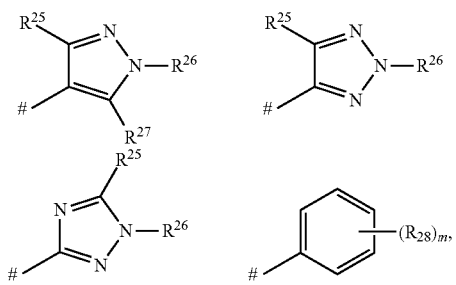

where # denotes the bond to the skeleton of the molecule; and $R^{21}, R^{22}, R^{23}, R^{24}$ are H, Cl, F or $CH_3$; $R^{25}$ is halogen, $C_1$-$C_4$-alkyl or $C_1$-$C_4$-haloalkyl; $R^{26}$ is $C_1$-$C_4$-alkyl; $R^{27}$ is halogen, $C_1$-$C_4$-alkoxy or $C_1$-$C_4$-haloalkoxy; $R^{28}$ is H, halogen, $C_1$-$C_4$-alkyl, $C_1$-$C_4$-haloalkyl or $C_1$-$C_4$-haloalkoxy; M is 0, 1, 2 or 3; X is oxygen; N is 0 or 1.

Preferred compounds of the formula 2 have the following meanings:
Y is

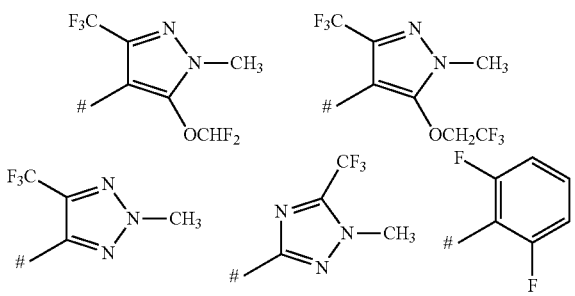

$R^{21}$ is H; $R^{22}, R^{23}$ are F; $R^{24}$ is H or F; X is oxygen; N is 0 or 1.

Particularly preferred compounds of the formula 2 are: 3-[5-(2,2-difluoroethoxy)-1-methyl-3-trifluoromethyl-1H-pyrazol-4-ylmethanesulfonyl]-4-fluoro-5,5-dimethyl-4,5-dihydroisoxazole (2-1); 3-{[5-(2,2-difluoroethoxy)-1-methyl-3-trifluoromethyl-1H-pyrazol-4-yl]fluoromethanesulfonyl}-5,5-dimethyl-4,5-dihydroisoxazole (2-2); 4-(4-fluoro-5,5-dimethyl-4,5-dihydroisoxazole-3-sulfonylmethyl)-2-methyl-5-trifluoromethyl-2H-[1,2,3]triazole (2-3); 4-[(5,5-dimethyl-4,5-dihydroisoxazole-3-sulfonyl)fluoromethyl]-2-methyl-5-trifluoromethyl-2H-[1,2,3]triazole (2-4); 4-(5,5-dimethyl-4,5-dihydroisoxazole-3-sulfonylmethyl)-2-methyl-5-trifluoromethyl-2H-[1,2,3]triazole (2-5); 3-{[5-(2,2-difluoroethoxy)-1-methyl-3-trifluoromethyl-1H-pyrazol-4-yl]difluoromethanesulfonyl}-5,5-dimethyl-4,5-dihydroisoxazole (2-6); 4-[(5,5-dimethyl-4,5-dihydroisoxazole-3-sulfonyl)difluoromethyl]-2-methyl-5-trifluoromethyl-2H-[1,2,3]triazole (2-7); 3-{[5-(2,2-difluoroethoxy)-1-methyl-3-trifluoromethyl-1H-pyrazol-4-yl]difluoromethanesulfonyl}-4-fluoro-5,5-dimethyl-4,5-dihydroisoxazole (2-8); 4-[difluoro-(4-fluoro-5,5-dimethyl-4,5-dihydroisoxazole-3-sulfonyl)methyl]-2-methyl-5-trifluoromethyl-2H-[1,2,3]triazole (2-9);

b11) from the group of the cellulose biosynthesis inhibitors:
chlorthiamid, dichlobenil, flupoxam and isoxaben;

b12) from the group of the decoupler herbicides:
dinoseb, dinoterb and DNOC and its salts;

b13) from the group of the auxin herbicides:
2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluoroxypyr, fluoroxypyr-butomethyl, fluoroxypyr-meptyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, and 5,6-dichloro-2-cyclopropyl-4-pyrimidinecarboxylic acid (H-9; CAS 858956-08-8) and its salts and esters;

b14) from the group of the auxin transport inhibitors:
diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (H-10; CAS 499223-49-3) and its salts and esters.

Examples of preferred safeners C are benoxacor, cloquintocet, cyometrinil, cyprosulfamide, dichlormid, dicyclonone, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (H-11; MON4660, CAS 71526-07-3) and 2,2,5-trimethyl-3-(dichloroacetyl)-1,3-oxazolidine (H-12; R-29148, CAS 52836-31-4).

The active compounds of groups b1) to b15) and the safeners C are known herbicides and safeners, see, for example, The Compendium of Pesticide Common Names (http://www.alanwood.net/pesticides/); B. Hock, C. Fedtke, R. R. Schmidt, Herbizide [Herbicides], Georg Thieme Verlag, Stuttgart, 1995. Further herbicidally active compounds are known from WO 96/26202, WO 97/41116, WO 97/41117, WO 97/41118, WO 01/83459 and WO 2008/074991 and from W. Krämer et al. (ed.) "Modern Crop Protection Compounds", Vol. 1, Wiley VCH, 2007 and the literature quoted therein.

The invention also relates to compositions in the form of a crop protection composition formulated as a 1-component composition comprising an active compound combination comprising at least one pyridine compound of the formula I and at least one further active compound, preferably selected from the active compounds of groups b1 to b15, and at least one solid or liquid carrier and/or one or more surfactants and, if desired, one or more further auxiliaries customary for crop protection compositions.

The invention also relates to compositions in the form of a crop protection composition formulated as a 2-component composition comprising a first component comprising at least one pyridine compound of the formula I, a solid or liquid carrier and/or one or more surfactants and a second component comprising at least one further active compound selected from the active compounds of groups b1 to b15, a solid or liquid carrier and/or one or more surfactants, where additionally both components may also comprise further auxiliaries customary for crop protection compositions.

In binary compositions comprising at least one compound of the formula I as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula I as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one compound of the formula I as component A, at least one herbicide B and at least one safener C, the relative parts by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1; the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1; and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. Preferably, the weight ratio of the components A+B to the component C is in the range of from 1:500 to 500:1, in particular in the range of from 1:250 to 250:1 and particularly preferably in the range of from 1:75 to 75:1.

Examples of particularly preferred compositions according to the invention comprising in each case one individualized compound of the formula I and one mixing partner or a mixing partner combination are given in Table B below.

A further aspect of the invention relates to the compositions B-1 to B-1236 listed in Table B below, where in each case one row of Table B corresponds to a herbicidal composition comprising one of the compounds of the formula I individualized in the above description (component 1) and the further active compound from groups b1) to b15) and/or safener C stated in each case in the row in question (component 2). The active compounds in the compositions described are in each case preferably present in synergistically effective amounts.

TABLE B

| | Herbicide(s) B | Safener C |
|---|---|---|
| B-1 | clodinafop-propargyl | — |
| B-2 | cycloxydim | — |
| B-3 | cyhalofop-butyl | — |
| B-4 | fenoxaprop-P-ethyl | — |
| B-5 | pinoxaden | — |

TABLE B-continued

| | Herbicide(s) B | Safener C |
|---|---|---|
| B-6 | profoxydim | — |
| B-7 | tepraloxydim | — |
| B-8 | tralkoxydim | — |
| B-9 | esprocarb | — |
| B-10 | prosulfocarb | — |
| B-11 | thiobencarb | — |
| B-12 | triallate | — |
| B-13 | bensulfuron-methyl | — |
| B-14 | bispyribac-sodium | — |
| B-15 | cyclosulfamuron | — |
| B-16 | flumetsulam | — |
| B-17 | flupyrsulfuron-methyl-sodium | — |
| B-18 | foramsulfuron | — |
| B-19 | imazamox | — |
| B-20 | imazapic | — |
| B-21 | imazapyr | — |
| B-22 | imazaquin | — |
| B-23 | imazethapyr | — |
| B-24 | imazosulfuron | — |
| B-25 | iodosulfuron-methyl-sodium | — |
| B-26 | mesosulfuron | — |
| B-27 | nicosulfuron | — |
| B-28 | penoxsulam | — |
| B-29 | propoxycarbazone-sodium | — |
| B-30 | pyrazosulfuron-ethyl | — |
| B-31 | pyroxsulam | — |
| B-32 | rimsulfuron | — |
| B-33 | sulfosulfuron | — |
| B-34 | thiencarbazone-methyl | — |
| B-35 | tritosulfuron | — |
| B-36 | 2,4-D and its salts and esters | — |
| B-37 | aminopyralid and its salts and esters | — |
| B-38 | clopyralid and its salts and esters | — |
| B-39 | dicamba and its salts and esters | — |
| B-40 | fluroxypyr-meptyl | — |
| B-41 | quinclorac | — |
| B-42 | quinmerac | — |
| B-43 | H-9 | — |
| B-44 | diflufenzopyr | — |
| B-45 | diflufenzopyr-sodium | — |
| B-46 | clomazone | — |
| B-47 | diflufenican | — |
| B-48 | fluorochloridone | — |
| B-49 | isoxaflutol | — |
| B-50 | mesotrione | — |
| B-51 | picolinafen | — |
| B-52 | sulcotrione | — |
| B-53 | tefuryltrione | — |
| B-54 | tembotrione | — |
| B-55 | topramezone | — |
| B-56 | H-7 | — |
| B-57 | atrazine | — |
| B-58 | diuron | — |
| B-59 | fluometuron | — |
| B-60 | hexazinone | — |
| B-61 | isoproturon | — |
| B-62 | metribuzin | — |
| B-63 | propanil | — |
| B-64 | terbuthylazine | — |
| B-65 | paraquat dichloride | — |
| B-66 | flumioxazin | — |
| B-67 | oxyfluorfen | — |
| B-68 | saflufenacil | — |
| B-69 | sulfentrazone | — |
| B-70 | H-1 | — |
| B-71 | H-2 | — |
| B-72 | glyphosate | — |
| B-73 | glyphosate-isopropylammonium | — |
| B-74 | glyphosate-trimesium (sulfosate) | — |
| B-75 | glufosinate | — |
| B-76 | glufosinate-ammonium | — |
| B-77 | pendimethalin | — |
| B-78 | trifluralin | — |
| B-79 | acetochlor | — |
| B-80 | cafenstrole | — |
| B-81 | dimethenamid-P | — |
| B-82 | fentrazamide | — |
| B-83 | flufenacet | — |

TABLE B-continued

| | Herbicide(s) B | Safener C |
|---|---|---|
| B-84 | mefenacet | — |
| B-85 | metazachlor | — |
| B-86 | metolachlor-S | — |
| B-87 | pyroxasulfone | — |
| B-88 | isoxaben | — |
| B-89 | dymron | — |
| B-90 | indanofan | — |
| B-91 | oxaziclomefone | — |
| B-92 | triaziflam | — |
| B-93 | chlorotoluron | — |
| B-94 | atrazine + H-1 | — |
| B-95 | atrazine + glyphosate | — |
| B-96 | atrazine + mesotrione | — |
| B-97 | atrazine + nicosulfuron | — |
| B-98 | atrazine + tembotrione | — |
| B-99 | atrazine + topramezone | — |
| B-100 | clomazone + glyphosate | — |
| B-101 | diflufenican + clodinafop-propargyl | — |
| B-102 | diflufenican + fenoxaprop-P-ethyl | — |
| B-103 | diflufenican + flupyrsulfuron-methyl-sodium | — |
| B-104 | diflufenican + glyphosate | — |
| B-105 | diflufenican + mesosulfuron-methyl | — |
| B-106 | diflufenican + pinoxaden | — |
| B-107 | diflufenican + pyroxsulam | — |
| B-108 | flumetsulam + glyphosate | — |
| B-109 | flumioxazin + glyphosate | — |
| B-110 | imazapic + glyphosate | — |
| B-111 | imazethapyr + glyphosate | — |
| B-112 | isoxaflutol + H-1 | — |
| B-113 | isoxaflutol + glyphosate | — |
| B-114 | metazachlor + H-1 | — |
| B-115 | metazachlor + glyphosate | — |
| B-116 | metazachlor + mesotrione | — |
| B-117 | metazachlor + nicosulfuron | — |
| B-118 | metazachlor + terbuthylazine | — |
| B-119 | metazachlor + topramezone | — |
| B-120 | metribuzin + glyphosate | — |
| B-121 | pendimethalin + H-1 | — |
| B-122 | pendimethalin + clodinafop-propargyl | — |
| B-123 | pendimethalin + fenoxaprop-P-ethyl | — |
| B-124 | pendimethalin + flupyrsulfuron-methyl-sodium | — |
| B-125 | pendimethalin + glyphosate | — |
| B-126 | pendimethalin + mesosulfuron-methyl | — |
| B-127 | pendimethalin + mesotrione | — |
| B-128 | pendimethalin + nicosulfuron | — |
| B-129 | pendimethalin + pinoxaden | — |
| B-130 | pendimethalin + pyroxsulam | — |
| B-131 | pendimethalin + tembotrione | — |
| B-132 | pendimethalin + topramezone | — |
| B-133 | pyroxasulfone + tembotrione | — |
| B-134 | pyroxasulfone + topramezone | — |
| B-135 | sulfentrazone + glyphosate | — |
| B-136 | terbuthylazine + H-1 | — |
| B-137 | terbuthylazine + foramsulfuron | — |
| B-138 | terbuthylazine + glyphosate | — |
| B-139 | terbuthylazine + mesotrione | — |
| B-140 | terbuthylazine + nicosulfuron | — |
| B-141 | terbuthylazine + tembotrione | — |
| B-142 | terbuthylazine + topramezone | — |
| B-143 | trifluralin + glyphosate | — |
| B-144 | — | benoxacor |
| B-145 | — | cloquintocet |
| B-146 | — | cyprosulfamide |
| B-147 | — | dichlormid |
| B-148 | — | fenchlorazole |
| B-149 | — | isoxadifen |
| B-150 | — | mefenpyr |
| B-151 | — | H-11 |
| B-152 | — | H-12 |
| B-153 | clodinafop-propargyl | benoxacor |
| B-154 | cycloxydim | benoxacor |
| B-155 | cyhalofop-butyl | benoxacor |
| B-156 | fenoxaprop-P-ethyl | benoxacor |
| B-157 | pinoxaden | benoxacor |
| B-158 | profoxydim | benoxacor |
| B-159 | tepraloxydim | benoxacor |
| B-160 | tralkoxydim | benoxacor |
| B-161 | esprocarb | benoxacor |
| B-162 | prosulfocarb | benoxacor |
| B-163 | thiobencarb | benoxacor |
| B-164 | triallate | benoxacor |
| B-165 | bensulfuron-methyl | benoxacor |
| B-166 | bispyribac-sodium | benoxacor |
| B-167 | cyclosulfamuron | benoxacor |
| B-168 | flumetsulam | benoxacor |
| B-169 | flupyrsulfuron-methyl-sodium | benoxacor |
| B-170 | foramsulfuron | benoxacor |
| B-171 | imazamox | benoxacor |
| B-172 | imazapic | benoxacor |
| B-173 | imazapyr | benoxacor |
| B-174 | imazaquin | benoxacor |
| B-175 | imazethapyr | benoxacor |
| B-176 | imazosulfuron | benoxacor |
| B-177 | iodosulfuron-methyl-sodium | benoxacor |
| B-178 | mesosulfuron | benoxacor |
| B-179 | nicosulfuron | benoxacor |
| B-180 | penoxsulam | benoxacor |
| B-181 | propoxycarbazone-sodium | benoxacor |
| B-182 | pyrazosulfuron-ethyl | benoxacor |
| B-183 | pyroxsulam | benoxacor |
| B-184 | rimsulfuron | benoxacor |
| B-185 | sulfosulfuron | benoxacor |
| B-186 | thiencarbazone-methyl | benoxacor |
| B-187 | tritosulfuron | benoxacor |
| B-188 | 2,4-D and its salts and esters | benoxacor |
| B-189 | aminopyralid and its salts and esters | benoxacor |
| B-190 | clopyralid and its salts and esters | benoxacor |
| B-191 | dicamba and its salts and esters | benoxacor |
| B-192 | fluroxypyr-meptyl | benoxacor |
| B-193 | quinclorac | benoxacor |
| B-194 | quinmerac | benoxacor |
| B-195 | H-9 | benoxacor |
| B-196 | diflufenzopyr | benoxacor |
| B-197 | diflufenzopyr-sodium | benoxacor |
| B-198 | clomazone | benoxacor |
| B-199 | diflufenican | benoxacor |
| B-200 | fluorochloridone | benoxacor |
| B-201 | isoxaflutol | benoxacor |
| B-202 | mesotrione | benoxacor |
| B-203 | picolinafen | benoxacor |
| B-204 | sulcotrione | benoxacor |
| B-205 | tefuryltrione | benoxacor |
| B-206 | tembotrione | benoxacor |
| B-207 | topramezone | benoxacor |
| B-208 | H-7 | benoxacor |
| B-209 | atrazine | benoxacor |
| B-210 | diuron | benoxacor |
| B-211 | fluometuron | benoxacor |
| B-212 | hexazinone | benoxacor |
| B-213 | isoproturon | benoxacor |
| B-214 | metribuzin | benoxacor |
| B-215 | propanil | benoxacor |
| B-216 | terbuthylazine | benoxacor |
| B-217 | paraquat dichloride | benoxacor |
| B-218 | flumioxazin | benoxacor |
| B-219 | oxyfluorfen | benoxacor |
| B-220 | saflufenacil | benoxacor |
| B-221 | sulfentrazone | benoxacor |
| B-222 | H-1 | benoxacor |
| B-223 | H-2 | benoxacor |
| B-224 | glyphosate | benoxacor |
| B-225 | glyphosate-isopropylammonium | benoxacor |
| B-226 | glyphosate-trimesium (sulfosate) | benoxacor |
| B-227 | glufosinate | benoxacor |
| B-228 | glufosinate-ammonium | benoxacor |
| B-229 | pendimethalin | benoxacor |
| B-230 | trifluralin | benoxacor |
| B-231 | acetochlor | benoxacor |
| B-232 | cafenstrole | benoxacor |
| B-233 | dimethenamid-P | benoxacor |
| B-234 | fentrazamide | benoxacor |
| B-235 | flufenacet | benoxacor |
| B-236 | mefenacet | benoxacor |
| B-237 | metazachlor | benoxacor |
| B-238 | metolachlor-S | benoxacor |
| B-239 | pyroxasulfone | benoxacor |

TABLE B-continued

| | Herbicide(s) B | Safener C |
|---|---|---|
| B-240 | isoxaben | benoxacor |
| B-241 | dymron | benoxacor |
| B-242 | indanofan | benoxacor |
| B-243 | oxaziclomefone | benoxacor |
| B-244 | triaziflam | benoxacor |
| B-245 | atrazine + H-1 | benoxacor |
| B-246 | atrazine + glyphosate | benoxacor |
| B-247 | atrazine + mesotrione | benoxacor |
| B-248 | atrazine + nicosulfuron | benoxacor |
| B-249 | atrazine + tembotrione | benoxacor |
| B-250 | atrazine + topramezone | benoxacor |
| B-251 | clomazone + glyphosate | benoxacor |
| B-252 | diflufenican + clodinafop-propargyl | benoxacor |
| B-253 | diflufenican + fenoxaprop-P-ethyl | benoxacor |
| B-254 | diflufenican + flupyrsulfuron-methyl-sodium | benoxacor |
| B-255 | diflufenican + glyphosate | benoxacor |
| B-256 | diflufenican + mesosulfuron-methyl | benoxacor |
| B-257 | diflufenican + pinoxaden | benoxacor |
| B-258 | diflufenican + pyroxsulam | benoxacor |
| B-259 | flumetsulam + glyphosate | benoxacor |
| B-260 | flumioxazin + glyphosate | benoxacor |
| B-261 | imazapic + glyphosate | benoxacor |
| B-262 | imazethapyr + glyphosate | benoxacor |
| B-263 | isoxaflutol + H-1 | benoxacor |
| B-264 | isoxaflutol + glyphosate | benoxacor |
| B-265 | metazachlor + H-1 | benoxacor |
| B-266 | metazachlor + glyphosate | benoxacor |
| B-267 | metazachlor + mesotrione | benoxacor |
| B-268 | metazachlor + nicosulfuron | benoxacor |
| B-269 | metazachlor + terbuthylazine | benoxacor |
| B-270 | metazachlor + topramezone | benoxacor |
| B-271 | metribuzin + glyphosate | benoxacor |
| B-272 | pendimethalin + H-1 | benoxacor |
| B-273 | pendimethalin + clodinafop-propargyl | benoxacor |
| B-274 | pendimethalin + fenoxaprop-P-ethyl | benoxacor |
| B-275 | pendimethalin + flupyrsulfuron-methyl-sodium | benoxacor |
| B-276 | pendimethalin + glyphosate | benoxacor |
| B-277 | pendimethalin + mesosulfuron-methyl | benoxacor |
| B-278 | pendimethalin + mesotrione | benoxacor |
| B-279 | pendimethalin + nicosulfuron | benoxacor |
| B-280 | pendimethalin + pinoxaden | benoxacor |
| B-281 | pendimethalin + pyroxsulam | benoxacor |
| B-282 | pendimethalin + tembotrione | benoxacor |
| B-283 | pendimethalin + topramezone | benoxacor |
| B-284 | pyroxasulfone + tembotrione | benoxacor |
| B-285 | pyroxasulfone + topramezone | benoxacor |
| B-286 | sulfentrazone + glyphosate | benoxacor |
| B-287 | terbuthylazine + H-1 | benoxacor |
| B-288 | terbuthylazine + foramsulfuron | benoxacor |
| B-289 | terbuthylazine + glyphosate | benoxacor |
| B-290 | terbuthylazine + mesotrione | benoxacor |
| B-291 | terbuthylazine + nicosulfuron | benoxacor |
| B-292 | terbuthylazine + tembotrione | benoxacor |
| B-293 | terbuthylazine + topramezone | benoxacor |
| B-294 | trifluralin + glyphosate | benoxacor |
| B-295 | clodinafop-propargyl | cloquintocet |
| B-296 | cycloxydim | cloquintocet |
| B-297 | cyhalofop-butyl | cloquintocet |
| B-298 | fenoxaprop-P-ethyl | cloquintocet |
| B-299 | pinoxaden | cloquintocet |
| B-300 | profoxydim | cloquintocet |
| B-301 | tepraloxydim | cloquintocet |
| B-302 | tralkoxydim | cloquintocet |
| B-303 | esprocarb | cloquintocet |
| B-304 | prosulfocarb | cloquintocet |
| B-305 | thiobencarb | cloquintocet |
| B-306 | triallate | cloquintocet |
| B-307 | bensulfuron-methyl | cloquintocet |
| B-308 | bispyribac-sodium | cloquintocet |
| B-309 | cyclosulfamuron | cloquintocet |
| B-310 | flumetsulam | cloquintocet |
| B-311 | flupyrsulfuron-methyl-sodium | cloquintocet |
| B-312 | foramsulfuron | cloquintocet |
| B-313 | imazamox | cloquintocet |
| B-314 | imazapic | cloquintocet |
| B-315 | imazapyr | cloquintocet |
| B-316 | imazaquin | cloquintocet |
| B-317 | imazethapyr | cloquintocet |
| B-318 | imazosulfuron | cloquintocet |
| B-319 | iodosulfuron-methyl-sodium | cloquintocet |
| B-320 | mesosulfuron | cloquintocet |
| B-321 | nicosulfuron | cloquintocet |
| B-322 | penoxsulam | cloquintocet |
| B-323 | propoxycarbazone-sodium | cloquintocet |
| B-324 | pyrazosulfuron-ethyl | cloquintocet |
| B-325 | pyroxsulam | cloquintocet |
| B-326 | rimsulfuron | cloquintocet |
| B-327 | sulfosulfuron | cloquintocet |
| B-328 | thiencarbazone-methyl | cloquintocet |
| B-329 | tritosulfuron | cloquintocet |
| B-330 | 2,4-D and its salts and esters | cloquintocet |
| B-331 | aminopyralid and its salts and esters | cloquintocet |
| B-332 | clopyralid and its salts and esters | cloquintocet |
| B-333 | dicamba and its salts and esters | cloquintocet |
| B-334 | fluroxypyr-meptyl | cloquintocet |
| B-335 | quinclorac | cloquintocet |
| B-336 | quinmerac | cloquintocet |
| B-337 | H-9 | cloquintocet |
| B-338 | diflufenzopyr | cloquintocet |
| B-339 | diflufenzopyr-sodium | cloquintocet |
| B-340 | clomazone | cloquintocet |
| B-341 | diflufenican | cloquintocet |
| B-342 | fluorochloridone | cloquintocet |
| B-343 | isoxaflutol | cloquintocet |
| B-344 | mesotrione | cloquintocet |
| B-345 | picolinafen | cloquintocet |
| B-346 | sulcotrione | cloquintocet |
| B-347 | tefuryltrione | cloquintocet |
| B-348 | tembotrione | cloquintocet |
| B-349 | topramezone | cloquintocet |
| B-350 | H-7 | cloquintocet |
| B-351 | atrazine | cloquintocet |
| B-352 | diuron | cloquintocet |
| B-353 | fluometuron | cloquintocet |
| B-354 | hexazinone | cloquintocet |
| B-355 | isoproturon | cloquintocet |
| B-356 | metribuzin | cloquintocet |
| B-357 | propanil | cloquintocet |
| B-358 | terbuthylazine | cloquintocet |
| B-359 | paraquat dichloride | cloquintocet |
| B-360 | flumioxazin | cloquintocet |
| B-361 | oxyfluorfen | cloquintocet |
| B-362 | saflufenacil | cloquintocet |
| B-363 | sulfentrazone | cloquintocet |
| B-364 | H-1 | cloquintocet |
| B-365 | H-2 | cloquintocet |
| B-366 | glyphosate | cloquintocet |
| B-367 | glyphosate-isopropylammonium | cloquintocet |
| B-368 | glyphosate-trimesium (sulfosate) | cloquintocet |
| B-369 | glufosinate | cloquintocet |
| B-370 | glufosinate-ammonium | cloquintocet |
| B-371 | pendimethalin | cloquintocet |
| B-372 | trifluralin | cloquintocet |
| B-373 | acetochlor | cloquintocet |
| B-374 | cafenstrole | cloquintocet |
| B-375 | dimethenamid-P | cloquintocet |
| B-376 | fentrazamide | cloquintocet |
| B-377 | flufenacet | cloquintocet |
| B-378 | mefenacet | cloquintocet |
| B-379 | metazachlor | cloquintocet |
| B-380 | metolachlor-S | cloquintocet |
| B-381 | pyroxasulfone | cloquintocet |
| B-382 | isoxaben | cloquintocet |
| B-383 | dymron | cloquintocet |
| B-384 | indanofan | cloquintocet |
| B-385 | oxaziclomefone | cloquintocet |
| B-386 | triaziflam | cloquintocet |
| B-387 | atrazine + H-1 | cloquintocet |
| B-388 | atrazine + glyphosate | cloquintocet |
| B-389 | atrazine + mesotrione | cloquintocet |
| B-390 | atrazine + nicosulfuron | cloquintocet |
| B-391 | atrazine + tembotrione | cloquintocet |
| B-392 | atrazine + topramezone | cloquintocet |
| B-393 | clomazone + glyphosate | cloquintocet |
| B-394 | diflufenican + clodinafop-propargyl | cloquintocet |
| B-395 | diflufenican + fenoxaprop-p-ethyl | cloquintocet |

TABLE B-continued

| | Herbicide(s) B | Safener C |
|---|---|---|
| B-396 | diflufenican + flupyrsulfuron-methyl-sodium | cloquintocet |
| B-397 | diflufenican + glyphosate | cloquintocet |
| B-398 | diflufenican + mesosulfuron-methyl | cloquintocet |
| B-399 | diflufenican + pinoxaden | cloquintocet |
| B-400 | diflufenican + pyroxsulam | cloquintocet |
| B-401 | flumetsulam + glyphosate | cloquintocet |
| B-402 | flumioxazin + glyphosate | cloquintocet |
| B-403 | imazapic + glyphosate | cloquintocet |
| B-404 | imazethapyr + glyphosate | cloquintocet |
| B-405 | isoxaflutol + H-1 | cloquintocet |
| B-406 | isoxaflutol + glyphosate | cloquintocet |
| B-407 | metazachlor + H-1 | cloquintocet |
| B-408 | metazachlor + glyphosate | cloquintocet |
| B-409 | metazachlor + mesotrione | cloquintocet |
| B-410 | metazachlor + nicosulfuron | cloquintocet |
| B-411 | metazachlor + terbuthylazine | cloquintocet |
| B-412 | metazachlor + topramezone | cloquintocet |
| B-413 | metribuzin + glyphosate | cloquintocet |
| B-414 | pendimethalin + H-1 | cloquintocet |
| B-415 | pendimethalin + clodinafop-propargyl | cloquintocet |
| B-416 | pendimethalin + fenoxaprop-P-ethyl | cloquintocet |
| B-417 | pendimethalin + flupyrsulfuron-methyl-sodium | cloquintocet |
| B-418 | pendimethalin + glyphosate | cloquintocet |
| B-419 | pendimethalin + mesosulfuron-methyl | cloquintocet |
| B-420 | pendimethalin + mesotrione | cloquintocet |
| B-421 | pendimethalin + nicosulfuron | cloquintocet |
| B-422 | pendimethalin + pinoxaden | cloquintocet |
| B-423 | pendimethalin + pyroxsulam | cloquintocet |
| B-424 | pendimethalin + tembotrione | cloquintocet |
| B-425 | pendimethalin + topramezone | cloquintocet |
| B-426 | pyroxasulfone + tembotrione | cloquintocet |
| B-427 | pyroxasulfone + topramezone | cloquintocet |
| B-428 | sulfentrazone + glyphosate | cloquintocet |
| B-429 | terbuthylazine + H-1 | cloquintocet |
| B-430 | terbuthylazine + foramsulfuron | cloquintocet |
| B-431 | terbuthylazine + glyphosate | cloquintocet |
| B-432 | terbuthylazine + mesotrione | cloquintocet |
| B-433 | terbuthylazine + nicosulfuron | cloquintocet |
| B-434 | terbuthylazine + tembotrione | cloquintocet |
| B-435 | terbuthylazine + topramezone | cloquintocet |
| B-436 | trifluralin + glyphosate | cloquintocet |
| B-437 | clodinafop-propargyl | dichlormid |
| B-438 | cycloxydim | dichlormid |
| B-439 | cyhalofop-butyl | dichlormid |
| B-440 | fenoxaprop-P-ethyl | dichlormid |
| B-441 | pinoxaden | dichlormid |
| B-442 | profoxydim | dichlormid |
| B-443 | tepraloxydim | dichlormid |
| B-444 | tralkoxydim | dichlormid |
| B-445 | esprocarb | dichlormid |
| B-446 | prosulfocarb | dichlormid |
| B-447 | thiobencarb | dichlormid |
| B-448 | triallate | dichlormid |
| B-449 | bensulfuron-methyl | dichlormid |
| B-450 | bispyribac-sodium | dichlormid |
| B-451 | cyclosulfamuron | dichlormid |
| B-452 | flumetsulam | dichlormid |
| B-453 | flupyrsulfuron-methyl-sodium | dichlormid |
| B-454 | foramsulfuron | dichlormid |
| B-455 | imazamox | dichlormid |
| B-456 | imazapic | dichlormid |
| B-457 | imazapyr | dichlormid |
| B-458 | imazaquin | dichlormid |
| B-459 | imazethapyr | dichlormid |
| B-460 | imazosulfuron | dichlormid |
| B-461 | iodosulfuron-methyl-sodium | dichlormid |
| B-462 | mesosulfuron | dichlormid |
| B-463 | nicosulfuron | dichlormid |
| B-464 | penoxsulam | dichlormid |
| B-465 | propoxycarbazone-sodium | dichlormid |
| B-466 | pyrazosulfuron-ethyl | dichlormid |
| B-467 | pyroxsulam | dichlormid |
| B-468 | rimsulfuron | dichlormid |
| B-469 | sulfosulfuron | dichlormid |
| B-470 | thiencarbazone-methyl | dichlormid |
| B-471 | tritosulfuron | dichlormid |
| B-472 | 2,4-D and its salts and esters | dichlormid |
| B-473 | aminopyralid and its salts and esters | dichlormid |
| B-474 | clopyralid and its salts and esters | dichlormid |
| B-475 | dicamba and its salts and esters | dichlormid |
| B-476 | fluroxypyr-meptyl | dichlormid |
| B-477 | quinclorac | dichlormid |
| B-478 | quinmerac | dichlormid |
| B-479 | H-9 | dichlormid |
| B-480 | diflufenzopyr | dichlormid |
| B-481 | diflufenzopyr-sodium | dichlormid |
| B-482 | clomazone | dichlormid |
| B-483 | diflufenican | dichlormid |
| B-484 | fluorochloridone | dichlormid |
| B-485 | isoxaflutol | dichlormid |
| B-486 | mesotrione | dichlormid |
| B-487 | picolinafen | dichlormid |
| B-488 | sulcotrione | dichlormid |
| B-489 | tefuryltrione | dichlormid |
| B-490 | tembotrione | dichlormid |
| B-491 | topramezone | dichlormid |
| B-492 | H-7 | dichlormid |
| B-493 | atrazine | dichlormid |
| B-494 | diuron | dichlormid |
| B-495 | fluometuron | dichlormid |
| B-496 | hexazinone | dichlormid |
| B-497 | isoproturon | dichlormid |
| B-498 | metribuzin | dichlormid |
| B-499 | propanil | dichlormid |
| B-500 | terbuthylazine | dichlormid |
| B-501 | paraquat dichloride | dichlormid |
| B-502 | flumioxazin | dichlormid |
| B-503 | oxyfluorfen | dichlormid |
| B-504 | saflufenacil | dichlormid |
| B-505 | sulfentrazone | dichlormid |
| B-506 | H-1 | dichlormid |
| B-507 | H-2 | dichlormid |
| B-508 | glyphosate | dichlormid |
| B-509 | glyphosate-isopropylammonium | dichlormid |
| B-510 | glyphosate-trimesium (sulfosate) | dichlormid |
| B-511 | glufosinate | dichlormid |
| B-512 | glufosinate-ammonium | dichlormid |
| B-513 | pendimethalin | dichlormid |
| B-514 | trifluralin | dichlormid |
| B-515 | acetochlor | dichlormid |
| B-516 | cafenstrole | dichlormid |
| B-517 | dimethenamid-P | dichlormid |
| B-518 | fentrazamide | dichlormid |
| B-519 | flufenacet | dichlormid |
| B-520 | mefenacet | dichlormid |
| B-521 | metazachlor | dichlormid |
| B-522 | metolachlor-S | dichlormid |
| B-523 | pyroxasulfone | dichlormid |
| B-524 | isoxaben | dichlormid |
| B-525 | dymron | dichlormid |
| B-526 | indanofan | dichlormid |
| B-527 | oxaziclomefone | dichlormid |
| B-528 | triaziflam | dichlormid |
| B-529 | atrazine + H-1 | dichlormid |
| B-530 | atrazine + glyphosate | dichlormid |
| B-531 | atrazine + mesotrione | dichlormid |
| B-532 | atrazine + nicosulfuron | dichlormid |
| B-533 | atrazine + tembotrione | dichlormid |
| B-534 | atrazine + topramezone | dichlormid |
| B-535 | clomazone + glyphosate | dichlormid |
| B-536 | diflufenican + clodinafop-propargyl | dichlormid |
| B-537 | diflufenican + fenoxaprop-p-ethyl | dichlormid |
| B-538 | diflufenican + flupyrsulfuron-methyl-sodium | dichlormid |
| B-539 | diflufenican + glyphosate | dichlormid |
| B-540 | diflufenican + mesosulfuron-methyl | dichlormid |
| B-541 | diflufenican + pinoxaden | dichlormid |
| B-542 | diflufenican + pyroxsulam | dichlormid |
| B-543 | flumetsulam + glyphosate | dichlormid |
| B-544 | flumioxazin + glyphosate | dichlormid |
| B-545 | imazapic + glyphosate | dichlormid |
| B-546 | imazethapyr + glyphosate | dichlormid |
| B-547 | isoxaflutol + H-1 | dichlormid |
| B-548 | isoxaflutol + glyphosate | dichlormid |
| B-549 | metazachlor + H-1 | dichlormid |
| B-550 | metazachlor + glyphosate | dichlormid |
| B-551 | metazachlor + mesotrione | dichlormid |

TABLE B-continued

| | Herbicide(s) B | Safener C |
|---|---|---|
| B-552 | metazachlor + nicosulfuron | dichlormid |
| B-553 | metazachlor + terbuthylazine | dichlormid |
| B-554 | metazachlor + topramezone | dichlormid |
| B-555 | metribuzin + glyphosate | dichlormid |
| B-556 | pendimethalin + H-1 | dichlormid |
| B-557 | pendimethalin + clodinafop-propargyl | dichlormid |
| B-558 | pendimethalin + fenoxaprop-P-ethyl | dichlormid |
| B-559 | pendimethalin + flupyrsulfuron-methyl-sodium | dichlormid |
| B-560 | pendimethalin + glyphosate | dichlormid |
| B-561 | pendimethalin + mesosulfuron-methyl | dichlormid |
| B-562 | pendimethalin + mesotrione | dichlormid |
| B-563 | pendimethalin + nicosulfuron | dichlormid |
| B-564 | pendimethalin + pinoxaden | dichlormid |
| B-565 | pendimethalin + pyroxsulam | dichlormid |
| B-566 | pendimethalin + tembotrione | dichlormid |
| B-567 | pendimethalin + topramezone | dichlormid |
| B-568 | pyroxasulfone + tembotrione | dichlormid |
| B-569 | pyroxasulfone + topramezone | dichlormid |
| B-570 | sulfentrazone + glyphosate | dichlormid |
| B-571 | terbuthylazine + H-1 | dichlormid |
| B-572 | terbuthylazine + foramsulfuron | dichlormid |
| B-573 | terbuthylazine + glyphosate | dichlormid |
| B-574 | terbuthylazine + mesotrione | dichlormid |
| B-575 | terbuthylazine + nicosulfuron | dichlormid |
| B-576 | terbuthylazine + tembotrione | dichlormid |
| B-577 | terbuthylazine + topramezone | dichlormid |
| B-578 | trifluralin + glyphosate | dichlormid |
| B-579 | clodinafop-propargyl | fenchlorazole |
| B-580 | cycloxydim | fenchlorazole |
| B-581 | cyhalofop-butyl | fenchlorazole |
| B-582 | fenoxaprop-P-ethyl | fenchlorazole |
| B-583 | pinoxaden | fenchlorazole |
| B-584 | profoxydim | fenchlorazole |
| B-585 | tepraloxydim | fenchlorazole |
| B-586 | tralkoxydim | fenchlorazole |
| B-587 | esprocarb | fenchlorazole |
| B-588 | prosulfocarb | fenchlorazole |
| B-589 | thiobencarb | fenchlorazole |
| B-590 | triallate | fenchlorazole |
| B-591 | bensulfuron-methyl | fenchlorazole |
| B-592 | bispyribac-sodium | fenchlorazole |
| B-593 | cyclosulfamuron | fenchlorazole |
| B-594 | flumetsulam | fenchlorazole |
| B-595 | flupyrsulfuron-methyl-sodium | fenchlorazole |
| B-596 | foramsulfuron | fenchlorazole |
| B-597 | imazamox | fenchlorazole |
| B-598 | imazapic | fenchlorazole |
| B-599 | imazapyr | fenchlorazole |
| B-600 | imazaquin | fenchlorazole |
| B-601 | imazethapyr | fenchlorazole |
| B-602 | imazosulfuron | fenchlorazole |
| B-603 | iodosulfuron-methyl-sodium | fenchlorazole |
| B-604 | mesosulfuron | fenchlorazole |
| B-605 | nicosulfuron | fenchlorazole |
| B-606 | penoxsulam | fenchlorazole |
| B-607 | propoxycarbazone-sodium | fenchlorazole |
| B-608 | pyrazosulfuron-ethyl | fenchlorazole |
| B-609 | pyroxsulam | fenchlorazole |
| B-610 | rimsulfuron | fenchlorazole |
| B-611 | sulfosulfuron | fenchlorazole |
| B-612 | thiencarbazone-methyl | fenchlorazole |
| B-613 | tritosulfuron | fenchlorazole |
| B-614 | 2,4-D and its salts and esters | fenchlorazole |
| B-615 | aminopyralid and its salts and esters | fenchlorazole |
| B-616 | clopyralid and its salts and esters | fenchlorazole |
| B-617 | dicamba and its salts and esters | fenchlorazole |
| B-618 | fluroxypyr-meptyl | fenchlorazole |
| B-619 | quinclorac | fenchlorazole |
| B-620 | quinmerac | fenchlorazole |
| B-621 | H-9 | fenchlorazole |
| B-622 | diflufenzopyr | fenchlorazole |
| B-623 | diflufenzopyr-sodium | fenchlorazole |
| B-624 | clomazone | fenchlorazole |
| B-625 | diflufenican | fenchlorazole |
| B-626 | fluorochloridone | fenchlorazole |
| B-627 | isoxaflutol | fenchlorazole |
| B-628 | mesotrione | fenchlorazole |
| B-629 | picolinafen | fenchlorazole |
| B-630 | sulcotrione | fenchlorazole |
| B-631 | tefuryltrione | fenchlorazole |
| B-632 | tembotrione | fenchlorazole |
| B-633 | topramezone | fenchlorazole |
| B-634 | H-7 | fenchlorazole |
| B-635 | atrazine | fenchlorazole |
| B-636 | diuron | fenchlorazole |
| B-637 | fluometuron | fenchlorazole |
| B-638 | hexazinone | fenchlorazole |
| B-639 | isoproturon | fenchlorazole |
| B-640 | metribuzin | fenchlorazole |
| B-641 | propanil | fenchlorazole |
| B-642 | terbuthylazine | fenchlorazole |
| B-643 | paraquat dichloride | fenchlorazole |
| B-644 | flumioxazin | fenchlorazole |
| B-645 | oxyfluorfen | fenchlorazole |
| B-646 | saflufenacil | fenchlorazole |
| B-647 | sulfentrazone | fenchlorazole |
| B-648 | H-1 | fenchlorazole |
| B-649 | H-2 | fenchlorazole |
| B-650 | glyphosate | fenchlorazole |
| B-651 | glyphosate-isopropylammonium | fenchlorazole |
| B-652 | glyphosate-trimesium (sulfosate) | fenchlorazole |
| B-653 | glufosinate | fenchlorazole |
| B-654 | glufosinate-ammonium | fenchlorazole |
| B-655 | pendimethalin | fenchlorazole |
| B-656 | trifluralin | fenchlorazole |
| B-657 | acetochlor | fenchlorazole |
| B-658 | cafenstrole | fenchlorazole |
| B-659 | dimethenamid-P | fenchlorazole |
| B-660 | fentrazamide | fenchlorazole |
| B-661 | flufenacet | fenchlorazole |
| B-662 | mefenacet | fenchlorazole |
| B-663 | metazachlor | fenchlorazole |
| B-664 | metolachlor-S | fenchlorazole |
| B-665 | pyroxasulfone | fenchlorazole |
| B-666 | isoxaben | fenchlorazole |
| B-667 | dymron | fenchlorazole |
| B-668 | indanofan | fenchlorazole |
| B-669 | oxaziclomefone | fenchlorazole |
| B-670 | triaziflam | fenchlorazole |
| B-671 | atrazine + H-1 | fenchlorazole |
| B-672 | atrazine + glyphosate | fenchlorazole |
| B-673 | atrazine + mesotrione | fenchlorazole |
| B-674 | atrazine + nicosulfuron | fenchlorazole |
| B-675 | atrazine + tembotrione | fenchlorazole |
| B-676 | atrazine + topramezone | fenchlorazole |
| B-677 | clomazone + glyphosate | fenchlorazole |
| B-678 | diflufenican + clodinafop-propargyl | fenchlorazole |
| B-679 | diflufenican + fenoxaprop-P-ethyl | fenchlorazole |
| B-680 | diflufenican + flupyrsulfuron-methyl-sodium | fenchlorazole |
| B-681 | diflufenican + glyphosate | fenchlorazole |
| B-682 | diflufenican + mesosulfuron-methyl | fenchlorazole |
| B-683 | diflufenican + pinoxaden | fenchlorazole |
| B-684 | diflufenican + pyroxsulam | fenchlorazole |
| B-685 | flumetsulam + glyphosate | fenchlorazole |
| B-686 | flumioxazin + glyphosate | fenchlorazole |
| B-687 | imazapic + glyphosate | fenchlorazole |
| B-688 | imazethapyr + glyphosate | fenchlorazole |
| B-689 | isoxaflutol + H-1 | fenchlorazole |
| B-690 | isoxaflutol + glyphosate | fenchlorazole |
| B-691 | metazachlor + H-1 | fenchlorazole |
| B-692 | metazachlor + glyphosate | fenchlorazole |
| B-693 | metazachlor + mesotrione | fenchlorazole |
| B-694 | metazachlor + nicosulfuron | fenchlorazole |
| B-695 | metazachlor + terbuthylazine | fenchlorazole |
| B-696 | metazachlor + topramezone | fenchlorazole |
| B-697 | metribuzin + glyphosate | fenchlorazole |
| B-698 | pendimethalin + H-1 | fenchlorazole |
| B-699 | pendimethalin + clodinafop-propargyl | fenchlorazole |
| B-700 | pendimethalin + fenoxaprop-P-ethyl | fenchlorazole |
| B-701 | pendimethalin + flupyrsulfuron-methyl-sodium | fenchlorazole |
| B-702 | pendimethalin + glyphosate | fenchlorazole |
| B-703 | pendimethalin + mesosulfuron-methyl | fenchlorazole |
| B-704 | pendimethalin + mesotrione | fenchlorazole |
| B-705 | pendimethalin + nicosulfuron | fenchlorazole |
| B-706 | pendimethalin + pinoxaden | fenchlorazole |
| B-707 | pendimethalin + pyroxsulam | fenchlorazole |

TABLE B-continued

| | Herbicide(s) B | Safener C |
|---|---|---|
| B-708 | pendimethalin + tembotrione | fenchlorazole |
| B-709 | pendimethalin + topramezone | fenchlorazole |
| B-710 | pyroxasulfone + tembotrione | fenchlorazole |
| B-711 | pyroxasulfone + topramezone | fenchlorazole |
| B-712 | sulfentrazone + glyphosate | fenchlorazole |
| B-713 | terbuthylazine + H-1 | fenchlorazole |
| B-714 | terbuthylazine + foramsulfuron | fenchlorazole |
| B-715 | terbuthylazine + glyphosate | fenchlorazole |
| B-716 | terbuthylazine + mesotrione | fenchlorazole |
| B-717 | terbuthylazine + nicosulfuron | fenchlorazole |
| B-718 | terbuthylazine + tembotrione | fenchlorazole |
| B-719 | terbuthylazine + topramezone | fenchlorazole |
| B-720 | trifluralin + glyphosate | fenchlorazole |
| B-721 | clodinafop-propargyl | isoxadifen |
| B-722 | cycloxydim | isoxadifen |
| B-723 | cyhalofop-butyl | isoxadifen |
| B-724 | fenoxaprop-P-ethyl | isoxadifen |
| B-725 | pinoxaden | isoxadifen |
| B-726 | profoxydim | isoxadifen |
| B-727 | tepraloxydim | isoxadifen |
| B-728 | tralkoxydim | isoxadifen |
| B-729 | esprocarb | isoxadifen |
| B-730 | prosulfocarb | isoxadifen |
| B-731 | thiobencarb | isoxadifen |
| B-732 | triallate | isoxadifen |
| B-733 | bensulfuron-methyl | isoxadifen |
| B-734 | bispyribac-sodium | isoxadifen |
| B-735 | cyclosulfamuron | isoxadifen |
| B-736 | flumetsulam | isoxadifen |
| B-737 | flupyrsulfuron-methyl-sodium | isoxadifen |
| B-738 | foramsulfuron | isoxadifen |
| B-739 | imazamox | isoxadifen |
| B-740 | imazapic | isoxadifen |
| B-741 | imazapyr | isoxadifen |
| B-742 | imazaquin | isoxadifen |
| B-743 | imazethapyr | isoxadifen |
| B-744 | imazosulfuron | isoxadifen |
| B-745 | iodosulfuron-methyl-sodium | isoxadifen |
| B-746 | mesosulfuron | isoxadifen |
| B-747 | nicosulfuron | isoxadifen |
| B-748 | penoxsulam | isoxadifen |
| B-749 | propoxycarbazone-sodium | isoxadifen |
| B-750 | pyrazosulfuron-ethyl | isoxadifen |
| B-751 | pyroxsulam | isoxadifen |
| B-752 | rimsulfuron | isoxadifen |
| B-753 | sulfosulfuron | isoxadifen |
| B-754 | thiencarbazone-methyl | isoxadifen |
| B-755 | tritosulfuron | isoxadifen |
| B-756 | 2,4-D and its salts and esters | isoxadifen |
| B-757 | aminopyralid and its salts and esters | isoxadifen |
| B-758 | clopyralid and its salts and esters | isoxadifen |
| B-759 | dicamba and its salts and esters | isoxadifen |
| B-760 | fluroxypyr-meptyl | isoxadifen |
| B-761 | quinclorac | isoxadifen |
| B-762 | quinmerac | isoxadifen |
| B-763 | H-9 | isoxadifen |
| B-764 | diflufenzopyr | isoxadifen |
| B-765 | diflufenzopyr-sodium | isoxadifen |
| B-766 | clomazone | isoxadifen |
| B-767 | diflufenican | isoxadifen |
| B-768 | fluorochloridone | isoxadifen |
| B-769 | isoxaflutol | isoxadifen |
| B-770 | mesotrione | isoxadifen |
| B-771 | picolinafen | isoxadifen |
| B-772 | sulcotrione | isoxadifen |
| B-773 | tefuryltrione | isoxadifen |
| B-774 | tembotrione | isoxadifen |
| B-775 | topramezone | isoxadifen |
| B-776 | H-7 | isoxadifen |
| B-777 | atrazine | isoxadifen |
| B-778 | diuron | isoxadifen |
| B-779 | fluometuron | isoxadifen |
| B-780 | hexazinone | isoxadifen |
| B-781 | isoproturon | isoxadifen |
| B-782 | metribuzin | isoxadifen |
| B-783 | propanil | isoxadifen |
| B-784 | terbuthylazine | isoxadifen |
| B-785 | paraquat dichloride | isoxadifen |
| B-786 | flumioxazin | isoxadifen |
| B-787 | oxyfluorfen | isoxadifen |
| B-788 | saflufenacil | isoxadifen |
| B-789 | sulfentrazone | isoxadifen |
| B-790 | H-1 | isoxadifen |
| B-791 | H-2 | isoxadifen |
| B-792 | glyphosate | isoxadifen |
| B-793 | glyphosate-isopropylammonium | isoxadifen |
| B-794 | glyphosate-trimesium (sulfosate) | isoxadifen |
| B-795 | glufosinate | isoxadifen |
| B-796 | glufosinate-ammonium | isoxadifen |
| B-797 | pendimethalin | isoxadifen |
| B-798 | trifluralin | isoxadifen |
| B-799 | acetochlor | isoxadifen |
| B-800 | cafenstrole | isoxadifen |
| B-801 | dimethenamid-P | isoxadifen |
| B-802 | fentrazamide | isoxadifen |
| B-803 | flufenacet | isoxadifen |
| B-804 | mefenacet | isoxadifen |
| B-805 | metazachlor | isoxadifen |
| B-806 | metolachlor-S | isoxadifen |
| B-807 | pyroxasulfone | isoxadifen |
| B-808 | isoxaben | isoxadifen |
| B-809 | dymron | isoxadifen |
| B-810 | indanofan | isoxadifen |
| B-811 | oxaziclomefone | isoxadifen |
| B-812 | triaziflam | isoxadifen |
| B-813 | atrazine + H-1 | isoxadifen |
| B-814 | atrazine + glyphosate | isoxadifen |
| B-815 | atrazine + mesotrione | isoxadifen |
| B-816 | atrazine + nicosulfuron | isoxadifen |
| B-817 | atrazine + tembotrione | isoxadifen |
| B-818 | atrazine + topramezone | isoxadifen |
| B-819 | clomazone + glyphosate | isoxadifen |
| B-820 | diflufenican + clodinafop-propargyl | isoxadifen |
| B-821 | diflufenican + fenoxaprop-P-ethyl | isoxadifen |
| B-822 | diflufenican + flupyrsulfuron-methyl-sodium | isoxadifen |
| B-823 | diflufenican + glyphosate | isoxadifen |
| B-824 | diflufenican + mesosulfuron-methyl | isoxadifen |
| B-825 | diflufenican + pinoxaden | isoxadifen |
| B-826 | diflufenican + pyroxsulam | isoxadifen |
| B-827 | flumetsulam + glyphosate | isoxadifen |
| B-828 | flumioxazin + glyphosate | isoxadifen |
| B-829 | imazapic + glyphosate | isoxadifen |
| B-830 | imazethapyr + glyphosate | isoxadifen |
| B-831 | isoxaflutol + H-1 | isoxadifen |
| B-832 | isoxaflutol + glyphosate | isoxadifen |
| B-833 | metazachlor + H-1 | isoxadifen |
| B-834 | metazachlor + glyphosate | isoxadifen |
| B-835 | metazachlor + mesotrione | isoxadifen |
| B-836 | metazachlor + nicosulfuron | isoxadifen |
| B-837 | metazachlor + terbuthylazine | isoxadifen |
| B-838 | metazachlor + topramezone | isoxadifen |
| B-839 | metribuzin + glyphosate | isoxadifen |
| B-840 | pendimethalin + H-1 | isoxadifen |
| B-841 | pendimethalin + clodinafop-propargyl | isoxadifen |
| B-842 | pendimethalin + fenoxaprop-P-ethyl | isoxadifen |
| B-843 | pendimethalin + flupyrsulfuron-methyl-sodium | isoxadifen |
| B-844 | pendimethalin + glyphosate | isoxadifen |
| B-845 | pendimethalin + mesosulfuron-methyl | isoxadifen |
| B-846 | pendimethalin + mesotrione | isoxadifen |
| B-847 | pendimethalin + nicosulfuron | isoxadifen |
| B-848 | pendimethalin + pinoxaden | isoxadifen |
| B-849 | pendimethalin + pyroxsulam | isoxadifen |
| B-850 | pendimethalin + tembotrione | isoxadifen |
| B-851 | pendimethalin + topramezone | isoxadifen |
| B-852 | pyroxasulfone + tembotrione | isoxadifen |
| B-853 | pyroxasulfone + topramezone | isoxadifen |
| B-854 | sulfentrazone + glyphosate | isoxadifen |
| B-855 | terbuthylazine + H-1 | isoxadifen |
| B-856 | terbuthylazine + foramsulfuron | isoxadifen |
| B-857 | terbuthylazine + glyphosate | isoxadifen |
| B-858 | terbuthylazine + mesotrione | isoxadifen |
| B-859 | terbuthylazine + nicosulfuron | isoxadifen |
| B-860 | terbuthylazine + tembotrione | isoxadifen |
| B-861 | terbuthylazine + topramezone | isoxadifen |
| B-862 | trifluralin + glyphosate | isoxadifen |
| B-863 | clodinafop-propargyl | mefenpyr |

TABLE B-continued

| | Herbicide(s) B | Safener C |
|---|---|---|
| B-864 | cycloxydim | mefenpyr |
| B-865 | cyhalofop-butyl | mefenpyr |
| B-866 | fenoxaprop-P-ethyl | mefenpyr |
| B-867 | pinoxaden | mefenpyr |
| B-868 | profoxydim | mefenpyr |
| B-869 | tepraloxydim | mefenpyr |
| B-870 | tralkoxydim | mefenpyr |
| B-871 | esprocarb | mefenpyr |
| B-872 | prosulfocarb | mefenpyr |
| B-873 | thiobencarb | mefenpyr |
| B-874 | triallate | mefenpyr |
| B-875 | bensulfuron-methyl | mefenpyr |
| B-876 | bispyribac-sodium | mefenpyr |
| B-877 | cyclosulfamuron | mefenpyr |
| B-878 | flumetsulam | mefenpyr |
| B-879 | flupyrsulfuron-methyl-sodium | mefenpyr |
| B-880 | foramsulfuron | mefenpyr |
| B-881 | imazamox | mefenpyr |
| B-882 | imazapic | mefenpyr |
| B-883 | imazapyr | mefenpyr |
| B-884 | imazaquin | mefenpyr |
| B-885 | imazethapyr | mefenpyr |
| B-886 | imazosulfuron | mefenpyr |
| B-887 | iodosulfuron-methyl-sodium | mefenpyr |
| B-888 | mesosulfuron | mefenpyr |
| B-889 | nicosulfuron | mefenpyr |
| B-890 | penoxsulam | mefenpyr |
| B-891 | propoxycarbazone-sodium | mefenpyr |
| B-892 | pyrazosulfuron-ethyl | mefenpyr |
| B-893 | pyroxsulam | mefenpyr |
| B-894 | rimsulfuron | mefenpyr |
| B-895 | sulfosulfuron | mefenpyr |
| B-896 | thiencarbazone-methyl | mefenpyr |
| B-897 | tritosulfuron | mefenpyr |
| B-898 | 2,4-D and its salts and esters | mefenpyr |
| B-899 | aminopyralid and its salts and esters | mefenpyr |
| B-900 | clopyralid and its salts and esters | mefenpyr |
| B-901 | dicamba and its salts and esters | mefenpyr |
| B-902 | fluroxypyr-meptyl | mefenpyr |
| B-903 | quinclorac | mefenpyr |
| B-904 | quinmerac | mefenpyr |
| B-905 | H-9 | mefenpyr |
| B-906 | diflufenzopyr | mefenpyr |
| B-907 | diflufenzopyr-sodium | mefenpyr |
| B-908 | clomazone | mefenpyr |
| B-909 | diflufenican | mefenpyr |
| B-910 | fluorochloridone | mefenpyr |
| B-911 | isoxaflutol | mefenpyr |
| B-912 | mesotrione | mefenpyr |
| B-913 | picolinafen | mefenpyr |
| B-914 | sulcotrione | mefenpyr |
| B-915 | tefuryltrione | mefenpyr |
| B-916 | tembotrione | mefenpyr |
| B-917 | topramezone | mefenpyr |
| B-918 | H-7 | mefenpyr |
| B-919 | atrazine | mefenpyr |
| B-920 | diuron | mefenpyr |
| B-921 | fluometuron | mefenpyr |
| B-922 | hexazinone | mefenpyr |
| B-923 | isoproturon | mefenpyr |
| B-924 | metribuzin | mefenpyr |
| B-925 | propanil | mefenpyr |
| B-926 | terbuthylazine | mefenpyr |
| B-927 | paraquat dichloride | mefenpyr |
| B-928 | flumioxazin | mefenpyr |
| B-929 | oxyfluorfen | mefenpyr |
| B-930 | saflufenacil | mefenpyr |
| B-931 | sulfentrazone | mefenpyr |
| B-932 | H-1 | mefenpyr |
| B-933 | H-2 | mefenpyr |
| B-934 | glyphosate | mefenpyr |
| B-935 | glyphosate-isopropylammonium | mefenpyr |
| B-936 | glyphosate-trimesium (sulfosate) | mefenpyr |
| B-937 | glufosinate | mefenpyr |
| B-938 | glufosinate-ammonium | mefenpyr |
| B-939 | pendimethalin | mefenpyr |
| B-940 | trifluralin | mefenpyr |
| B-941 | acetochlor | mefenpyr |
| B-942 | cafenstrole | mefenpyr |
| B-943 | dimethenamid-P | mefenpyr |
| B-944 | fentrazamide | mefenpyr |
| B-945 | flufenacet | mefenpyr |
| B-946 | mefenacet | mefenpyr |
| B-947 | metazachlor | mefenpyr |
| B-948 | metolachlor-S | mefenpyr |
| B-949 | pyroxasulfone | mefenpyr |
| B-950 | isoxaben | mefenpyr |
| B-951 | dymron | mefenpyr |
| B-952 | indanofan | mefenpyr |
| B-953 | oxaziclomefone | mefenpyr |
| B-954 | triaziflam | mefenpyr |
| B-955 | atrazine + H-1 | mefenpyr |
| B-956 | atrazine + glyphosate | mefenpyr |
| B-957 | atrazine + mesotrione | mefenpyr |
| B-958 | atrazine + nicosulfuron | mefenpyr |
| B-959 | atrazine + tembotrione | mefenpyr |
| B-960 | atrazine + topramezone | mefenpyr |
| B-961 | clomazone + glyphosate | mefenpyr |
| B-962 | diflufenican + clodinafop-propargyl | mefenpyr |
| B-963 | diflufenican + fenoxaprop-P-ethyl | mefenpyr |
| B-964 | diflufenican + flupyrsulfuron-methyl-sodium | mefenpyr |
| B-965 | diflufenican + glyphosate | mefenpyr |
| B-966 | diflufenican + mesosulfuron-methyl | mefenpyr |
| B-967 | diflufenican + pinoxaden | mefenpyr |
| B-968 | diflufenican + pyroxsulam | mefenpyr |
| B-969 | flumetsulam + glyphosate | mefenpyr |
| B-970 | flumioxazin + glyphosate | mefenpyr |
| B-971 | imazapic + glyphosate | mefenpyr |
| B-972 | imazethapyr + glyphosate | mefenpyr |
| B-973 | isoxaflutol + H-1 | mefenpyr |
| B-974 | isoxaflutol + glyphosate | mefenpyr |
| B-975 | metazachlor + H-1 | mefenpyr |
| B-976 | metazachlor + glyphosate | mefenpyr |
| B-977 | metazachlor + mesotrione | mefenpyr |
| B-978 | metazachlor + nicosulfuron | mefenpyr |
| B-979 | metazachlor + terbuthylazine | mefenpyr |
| B-980 | metazachlor + topramezone | mefenpyr |
| B-981 | metribuzin + glyphosate | mefenpyr |
| B-982 | pendimethalin + H-1 | mefenpyr |
| B-983 | pendimethalin + clodinafop-propargyl | mefenpyr |
| B-984 | pendimethalin + fenoxaprop-P-ethyl | mefenpyr |
| B-985 | pendimethalin + flupyrsulfuron-methyl-sodium | mefenpyr |
| B-986 | pendimethalin + glyphosate | mefenpyr |
| B-987 | pendimethalin + mesosulfuron-methyl | mefenpyr |
| B-988 | pendimethalin + mesotrione | mefenpyr |
| B-989 | pendimethalin + nicosulfuron | mefenpyr |
| B-990 | pendimethalin + pinoxaden | mefenpyr |
| B-991 | pendimethalin + pyroxsulam | mefenpyr |
| B-992 | pendimethalin + tembotrione | mefenpyr |
| B-993 | pendimethalin + topramezone | mefenpyr |
| B-994 | pyroxasulfone + tembotrione | mefenpyr |
| B-995 | pyroxasulfone + topramezone | mefenpyr |
| B-996 | sulfentrazone + glyphosate | mefenpyr |
| B-997 | terbuthylazine + H-1 | mefenpyr |
| B-998 | terbuthylazine + foramsulfuron | mefenpyr |
| B-999 | terbuthylazine + glyphosate | mefenpyr |
| B-1000 | terbuthylazine + mesotrione | mefenpyr |
| B-1001 | terbuthylazine + nicosulfuron | mefenpyr |
| B-1002 | terbuthylazine + tembotrione | mefenpyr |
| B-1003 | terbuthylazine + topramezone | mefenpyr |
| B-1004 | trifluralin + glyphosate | mefenpyr |
| B-1005 | clodinafop-propargyl | H-12 |
| B-1006 | cycloxydim | H-12 |
| B-1007 | cyhalofop-butyl | H-12 |
| B-1008 | fenoxaprop-P-ethyl | H-12 |
| B-1009 | pinoxaden | H-12 |
| B-1010 | profoxydim | H-12 |
| B-1011 | tepraloxydim | H-12 |
| B-1012 | tralkoxydim | H-12 |
| B-1013 | esprocarb | H-12 |
| B-1014 | prosulfocarb | H-12 |
| B-1015 | thiobencarb | H-12 |
| B-1016 | triallate | H-12 |
| B-1017 | bensulfuron-methyl | H-12 |
| B-1018 | bispyribac-sodium | H-12 |
| B-1019 | cyclosulfamuron | H-12 |

TABLE B-continued

| | Herbicide(s) B | Safener C |
|---|---|---|
| B-1020 | flumetsulam | H-12 |
| B-1021 | flupyrsulfuron-methyl-sodium | H-12 |
| B-1022 | foramsulfuron | H-12 |
| B-1023 | imazamox | H-12 |
| B-1024 | imazapic | H-12 |
| B-1025 | imazapyr | H-12 |
| B-1026 | imazaquin | H-12 |
| B-1027 | imazethapyr | H-12 |
| B-1028 | imazosulfuron | H-12 |
| B-1029 | iodosulfuron-methyl-sodium | H-12 |
| B-1030 | mesosulfuron | H-12 |
| B-1031 | nicosulfuron | H-12 |
| B-1032 | penoxsulam | H-12 |
| B-1033 | propoxycarbazone-sodium | H-12 |
| B-1034 | pyrazosulfuron-ethyl | H-12 |
| B-1035 | pyroxsulam | H-12 |
| B-1036 | rimsulfuron | H-12 |
| B-1037 | sulfosulfuron | H-12 |
| B-1038 | thiencarbazone-methyl | H-12 |
| B-1039 | tritosulfuron | H-12 |
| B-1040 | 2,4-D and its salts and esters | H-12 |
| B-1041 | aminopyralid and its salts and esters | H-12 |
| B-1042 | clopyralid and its salts and esters | H-12 |
| B-1043 | dicamba and its salts and esters | H-12 |
| B-1044 | fluroxypyr-meptyl | H-12 |
| B-1045 | quinclorac | H-12 |
| B-1046 | quinmerac | H-12 |
| B-1047 | B-9 | H-12 |
| B-1048 | diflufenzopyr | H-12 |
| B-1049 | diflufenzopyr-sodium | H-12 |
| B-1050 | clomazone | H-12 |
| B-1051 | diflufenican | H-12 |
| B-1052 | fluorochloridone | H-12 |
| B-1053 | isoxaflutol | H-12 |
| B-1054 | mesotrione | H-12 |
| B-1055 | picolinafen | H-12 |
| B-1056 | sulcotrione | H-12 |
| B-1057 | tefuryltrione | H-12 |
| B-1058 | tembotrione | H-12 |
| B-1059 | topramezone | H-12 |
| B-1060 | H-7 | H-12 |
| B-1061 | atrazine | H-12 |
| B-1062 | diuron | H-12 |
| B-1063 | fluometuron | H-12 |
| B-1064 | hexazinone | H-12 |
| B-1065 | isoproturon | H-12 |
| B-1066 | metribuzin | H-12 |
| B-1067 | propanil | H-12 |
| B-1068 | terbuthylazine | H-12 |
| B-1069 | paraquat dichloride | H-12 |
| B-1070 | flumioxazin | H-12 |
| B-1071 | oxyfluorfen | H-12 |
| B-1072 | saflufenacil | H-12 |
| B-1073 | sulfentrazone | H-12 |
| B-1074 | H-1 | H-12 |
| B-1075 | H-2 | H-12 |
| B-1076 | glyphosate | H-12 |
| B-1077 | glyphosate-isopropylammonium | H-12 |
| B-1078 | glyphosate-trimesium (sulfosate) | H-12 |
| B-1079 | glufosinate | H-12 |
| B-1080 | glufosinate-ammonium | H-12 |
| B-1081 | pendimethalin | H-12 |
| B-1082 | trifluralin | H-12 |
| B-1083 | acetochlor | H-12 |
| B-1084 | cafenstrole | H-12 |
| B-1085 | dimethenamid-P | H-12 |
| B-1086 | fentrazamide | H-12 |
| B-1087 | flufenacet | H-12 |
| B-1088 | mefenacet | H-12 |
| B-1089 | metazachlor | H-12 |
| B-1090 | metolachlor-S | H-12 |
| B-1091 | pyroxasulfone | H-12 |
| B-1092 | isoxaben | H-12 |
| B-1093 | dymron | H-12 |
| B-1094 | indanofan | H-12 |
| B-1095 | oxaziclomefone | H-12 |
| B-1096 | triaziflam | H-12 |
| B-1097 | atrazine + H-1 | H-12 |
| B-1098 | atrazine + glyphosate | H-12 |
| B-1099 | atrazine + mesotrione | H-12 |
| B-1100 | atrazine + nicosulfuron | H-12 |
| B-1101 | atrazine + tembotrione | H-12 |
| B-1102 | atrazine + topramezone | H-12 |
| B-1103 | clomazone + glyphosate | H-12 |
| B-1104 | diflufenican + clodinafop-propargyl | H-12 |
| B-1105 | diflufenican + fenoxaprop-P-ethyl | H-12 |
| B-1106 | diflufenican + flupyrsulfuron-methyl-sodium | H-12 |
| B-1107 | diflufenican + glyphosate | H-12 |
| B-1108 | diflufenican + mesosulfuron-methyl | H-12 |
| B-1109 | diflufenican + pinoxaden | H-12 |
| B-1110 | diflufenican + pyroxsulam | H-12 |
| B-1111 | flumetsulam + glyphosate | H-12 |
| B-1112 | flumioxazin + glyphosate | H-12 |
| B-1113 | imazapic + glyphosate | H-12 |
| B-1114 | imazethapyr + glyphosate | H-12 |
| B-1115 | isoxaflutol + H-1 | H-12 |
| B-1116 | isoxaflutol + glyphosate | H-12 |
| B-1117 | metazachlor + H-1 | H-12 |
| B-1118 | metazachlor + glyphosate | H-12 |
| B-1119 | metazachlor + mesotrione | H-12 |
| B-1120 | metazachlor + nicosulfuron | H-12 |
| B-1121 | metazachlor + terbuthylazine | H-12 |
| B-1122 | metazachlor + topramezone | H-12 |
| B-1123 | metribuzin + glyphosate | H-12 |
| B-1124 | pendimethalin + H-1 | H-12 |
| B-1125 | pendimethalin + clodinafop-propargyl | H-12 |
| B-1126 | pendimethalin + fenoxaprop-P-ethyl | H-12 |
| B-1127 | pendimethalin + flupyrsulfuron-methyl-sodium | H-12 |
| B-1128 | pendimethalin + glyphosate | H-12 |
| B-1129 | pendimethalin + mesosulfuron-methyl | H-12 |
| B-1130 | pendimethalin + mesotrione | H-12 |
| B-1131 | pendimethalin + nicosulfuron | H-12 |
| B-1132 | pendimethalin + pinoxaden | H-12 |
| B-1133 | pendimethalin + pyroxsulam | H-12 |
| B-1134 | pendimethalin + tembotrione | H-12 |
| B-1135 | pendimethalin + topramezone | H-12 |
| B-1136 | pyroxasulfone + tembotrione | H-12 |
| B-1137 | pyroxasulfone + topramezone | H-12 |
| B-1138 | sulfentrazone + glyphosate | H-12 |
| B-1139 | terbuthylazine + H-1 | H-12 |
| B-1140 | terbuthylazine + foramsulfuron | H-12 |
| B-1141 | terbuthylazine + glyphosate | H-12 |
| B-1142 | terbuthylazine + mesotrione | H-12 |
| B-1143 | terbuthylazine + nicosulfuron | H-12 |
| B-1144 | terbuthylazine + tembotrione | H-12 |
| B-1145 | terbuthylazine + topramezone | H-12 |
| B-1146 | trifluralin + glyphosate | H-12 |
| B-1147 | 2-1 | — |
| B-1148 | 2-2 | — |
| B-1149 | 2-3 | — |
| B-1150 | 2-4 | — |
| B-1151 | 2-5 | — |
| B-1152 | 2-6 | — |
| B-1153 | 2-7 | — |
| B-1154 | 2-8 | — |
| B-1155 | 2-9 | — |
| B-1156 | 2-1 | benoxacor |
| B-1157 | 2-2 | benoxacor |
| B-1158 | 2-3 | benoxacor |
| B-1159 | 2-4 | benoxacor |
| B-1160 | 2-5 | benoxacor |
| B-1161 | 2-6 | benoxacor |
| B-1162 | 2-7 | benoxacor |
| B-1163 | 2-8 | benoxacor |
| B-1164 | 2-9 | benoxacor |
| B-1165 | 2-1 | cloquintocet |
| B-1166 | 2-2 | cloquintocet |
| B-1167 | 2-3 | cloquintocet |
| B-1168 | 2-4 | cloquintocet |
| B-1169 | 2-5 | cloquintocet |
| B-1170 | 2-6 | cloquintocet |
| B-1171 | 2-7 | cloquintocet |
| B-1172 | 2-8 | cloquintocet |
| B-1173 | 2-9 | cloquintocet |
| B-1174 | 2-1 | cyprosulfamide |
| B-1175 | 2-2 | cyprosulfamide |

TABLE B-continued

| Herbicide(s) B | | Safener C |
|---|---|---|
| B-1176 | 2-3 | cyprosulfamide |
| B-1177 | 2-4 | cyprosulfamide |
| B-1178 | 2-5 | cyprosulfamide |
| B-1179 | 2-6 | cyprosulfamide |
| B-1180 | 2-7 | cyprosulfamide |
| B-1181 | 2-8 | cyprosulfamide |
| B-1182 | 2-9 | cyprosulfamide |
| B-1183 | 2-1 | dichlormid |
| B-1184 | 2-2 | dichlormid |
| B-1185 | 2-3 | dichlormid |
| B-1186 | 2-4 | dichlormid |
| B-1187 | 2-5 | dichlormid |
| B-1188 | 2-6 | dichlormid |
| B-1189 | 2-7 | dichlormid |
| B-1190 | 2-8 | dichlormid |
| B-1191 | 2-9 | dichlormid |
| B-1192 | 2-1 | fenchlorazole |
| B-1193 | 2-2 | fenchlorazole |
| B-1194 | 2-3 | fenchlorazole |
| B-1195 | 2-4 | fenchlorazole |
| B-1196 | 2-5 | fenchlorazole |
| B-1197 | 2-6 | fenchlorazole |
| B-1198 | 2-7 | fenchlorazole |
| B-1199 | 2-8 | fenchlorazole |
| B-1200 | 2-9 | fenchlorazole |
| B-1201 | 2-1 | isoxadifen |
| B-1202 | 2-2 | isoxadifen |
| B-1203 | 2-3 | isoxadifen |
| B-1204 | 2-4 | isoxadifen |
| B-1205 | 2-5 | isoxadifen |
| B-1206 | 2-6 | isoxadifen |
| B-1207 | 2-7 | isoxadifen |
| B-1208 | 2-8 | isoxadifen |
| B-1209 | 2-9 | isoxadifen |
| B-1210 | 2-1 | mefenpyr |
| B-1211 | 2-2 | mefenpyr |
| B-1212 | 2-3 | mefenpyr |
| B-1213 | 2-4 | mefenpyr |
| B-1214 | 2-5 | mefenpyr |
| B-1215 | 2-6 | mefenpyr |
| B-1216 | 2-7 | mefenpyr |
| B-1217 | 2-8 | mefenpyr |
| B-1218 | 2-9 | mefenpyr |
| B-1219 | 2-1 | H-11 |
| B-1220 | 2-2 | H-11 |
| B-1221 | 2-3 | H-11 |
| B-1222 | 2-4 | H-11 |
| B-1223 | 2-5 | H-11 |
| B-1224 | 2-6 | H-11 |
| B-1225 | 2-7 | H-11 |
| B-1226 | 2-8 | H-11 |
| B-1227 | 2-9 | H-11 |
| B-1228 | 2-1 | H-12 |
| B-1229 | 2-2 | H-12 |
| B-1230 | 2-3 | H-12 |
| B-1231 | 2-4 | H-12 |
| B-1232 | 2-5 | H-12 |
| B-1233 | 2-6 | H-12 |
| B-1234 | 2-7 | H-12 |
| B-1235 | 2-8 | H-12 |
| B-1236 | 2-9 | H-12 |

The compounds I and the compositions according to the invention may also have a plant-strengthening action. Accordingly, they are suitable for mobilizing the defense system of the plants against attack by unwanted microorganisms, such as harmful fungi, but also viruses and bacteria. Plant-strengthening (resistance-inducing) substances are to be understood as meaning, in the present context, those substances which are capable of stimulating the defense system of treated plants in such a way that, when subsequently inoculated by unwanted microorganisms, the treated plants display a substantial degree of resistance to these microorganisms.

The compounds I can be employed for protecting plants against attack by unwanted microorganisms within a certain period of time after the treatment. The period of time within which their protection is effected generally extends from 1 to 28 days, preferably from 1 to 14 days, after the treatment of the plants with the compounds I, or, after treatment of the seed, for up to 9 months after sowing.

The compounds I and the compositions according to the invention are also suitable for increasing the harvest yield.

Moreover, they have reduced toxicity and are tolerated well by the plants.

Hereinbelow, the compounds of the formula I are illustrated by way of examples, without limiting the subject matter of the present invention to the examples shown.

I. SYNTHESIS EXAMPLES

With appropriate modification of the starting materials, the procedures given in the synthesis examples below were used to obtain further compounds I. The compounds obtained in this manner are listed in the table that follows, together with physical data.

The products shown below were characterized by determination of the melting point, by NMR spectroscopy or by the masses ([m/z]) or retention time (RT; [min.]) determined by HPLC-MS spectrometry.

HPLC-MS=high performance liquid chromatography coupled with mass spectrometry; HPLC column:

RP-18 column (Chromolith Speed ROD from Merck KgaA, Germany), 50*4.6 mm; mobile phase: acetonitrile+0.1% trifluoroacetic acid (TFA)/water+0.1% TFA, using a gradient from 5:95 to 100:0 over 5 minutes at 40° C., flow rate 1.8 ml/min.

MS: quadrupole electrospray ionization, 80 V (positive mode).

Ac: Acetyl; THF: tetrahydrofurane; DMF: dimethylformamide; dppf: 1,1'-bis(diphenylphosphino)ferrocen; dba: dibenzylidenacetone; PE: petrol ether; EtOAc: acetic acid ethyl ester; DCM: dichloromethane; NCS: N-chlorosuccinimide; LiHMDS: lithium-hexamethyldisilazane; AcOH: acetic acid; MeOH: methanol; TFA: trifluoroacetic acid; Ph: phenyl; i-Pr: iso-propyl; t-Bu: tert-butyl.

Example 1

Preparation of 3-[5-chloro-3-morpholino-2-(trifluoromethyl)phenyl]-4-hydroxy-pyrano[3,2-b]pyridin-2-one (Hereinafter Also Referred to as Compound 11 which Corresponds to Compound I-49 in the Table I Below)

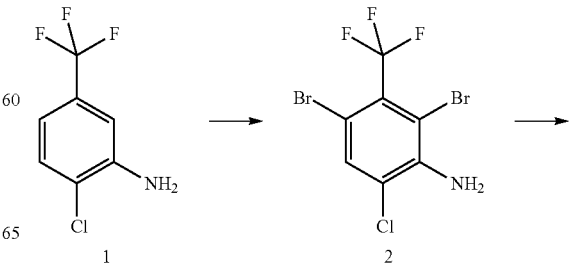

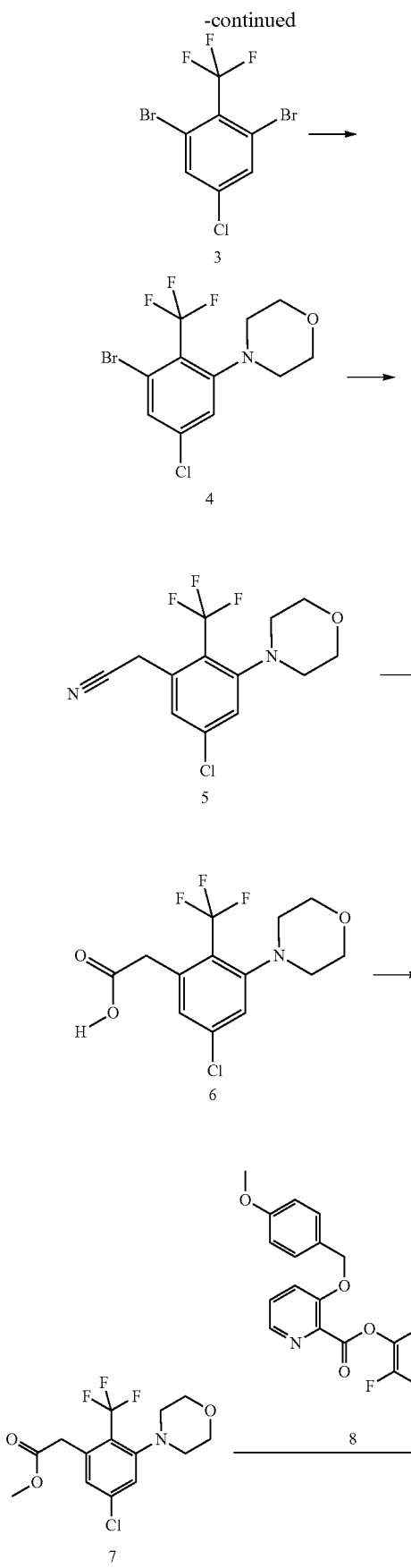

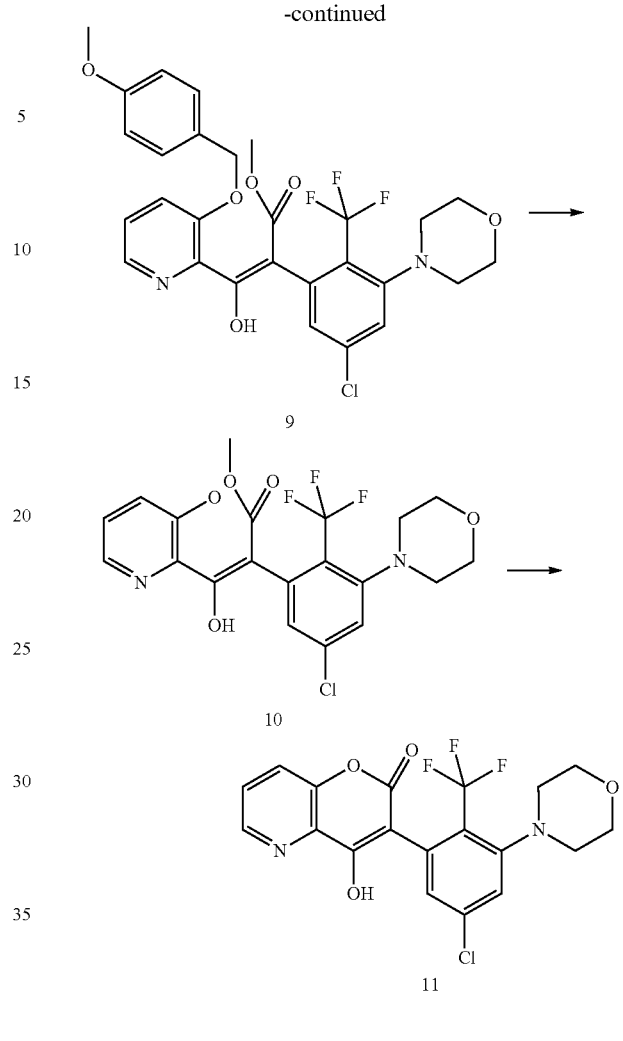

Step 1: To a solution of compound 1 (80 g, 0.41 mol) in 800 ml AcOH was added Br₂ (131 g, 0.82 mol) at room temperature. The mixture was stirred at 50° C. for 5 hrs. The mixture was diluted with CH$_2$Cl$_2$ and washed with water, aq. Na$_2$CO$_3$ and brine, the organic layer was dried over Na$_2$SO$_4$ and concentrated in vacuum, the crude product was purified by column chromatography to give compound 2 (80 g, yield: 55%).

¹H NMR MeOD 400 MHz δ 7.69 (s, 1H).

Step 2: To a solution of compound 2 (40 g, 0.11 mol) in H$_3$PO$_4$ (1.2 l) was added dropwise a solution of NaNO$_2$ (47 g, 0.68 mol) in 200 ml water at −4° C., H$_3$PO$_2$ (480 ml) was added dropwise at −4° C. The resulting mixture was stirred overnight at room temperature. The reaction mixture was diluted with CH$_2$Cl$_2$ and neutralized with sat. Na$_2$CO$_3$, the organic layer was washed brine, dried over anhydrous Na$_2$SO$_4$ and concentrated in vacuo, the crude product was purified by column chromatography to give compound 3 (30 g, yield: 78%).

¹H NMR MeOD 400 MHz δ 7.93 (s, 2H).

Step 3: A mixture of compound 3 (10 g, 29.6 mmol), morpholine (2.6 g, 29.6 mmol), t-BuONa (5.7 g, 59.1 mmol), dppf (1.0 g, 1.77 mmol) and Pd$_2$(dba)$_3$ (0.81 g, 0.89 mmol) in toluene (150 ml) was heated to 90° C. under N$_2$ atmosphere overnight. The reaction mixture was filtered and concentrated in vacuo, the residue was purified by column chromatography to give compound 4 (2.8 g, yield: 25%).

$^1$H NMR MeOD 400 MHz δ 7.56 (s, 1H), 7.33 (s, 1H), 3.77-3.79 (m, 4H), 2.95~2.97 (m, 4H).

Step 4: A mixture of compound 4 (5.0 g, 14.5 mmol), tri-n-butyl(cyanomethyl) stannane (5.7 g, 17.4 mmol, for preparation reference is made to J. Org. Chem. 1988, 53, 3051-3057), and $PdCl_2-[(o-tolyl)_3]_2$ (120 mg, 0.15 mmol) in xylene (50 ml) was heated to 120° C. under $N_2$ atmosphere overnight. The reaction mixture was concentrated in vacuum, the residue was purified by column chromatography (PE: EtOAc=10:1) to give compound 5 (1 g, yield: 24%).

$^1$H NMR MeOD 400 MHz δ 7.56 (s, 1H), 7.33 (s, 1H), 4.57 (s, 2H), 3.78~3.80 (m, 4H), 2.95~2.97 (m, 4H).

Step 5: A mixture of compound 5 (2.7 g, 8.9 mmol) in 30 ml of HCl:AcOH (1:1) was stirred at 100° C. for 3 hrs. The reaction mixture was concentrated and diluted with water, the aqueous layer was basified to pH 9 with sat. $NaHCO_3$ and washed with EtOAc. The aqueous layer was acidified to pH 3, extracted with EtOAc and washed with brine. The organic layer was dried over anhydrous $Na_2SO_4$ and concentrated in vacuo to give compound 6 (1.3 g, yield: 45%).

$^1$H NMR: $CDCl_3$ 400 MHz δ 7.23 (s, 1H), 7.08 (s, 1H), 3.81~3.83 (m, 6H), 2.89~2.92 (m, 4H).

Step 6: To a mixture of compound 6 (1.3 g, 4.0 mmol) in MeOH (30 ml) was added conc. $H_2SO_4$ (0.8 g, 8.0 mmol) at room temperature, then the resulting mixture was heated under reflux for 4 hrs. The reaction mixture was concentrated in vacuo, the residue was basified with saturated aq. $NaHCO_3$ and extracted with EtOAc. The organic layer was washed with brine and dried over $Na_2SO_4$, concentrated in vacuo to give compound 7 (1.1 g, yield: 81%).

$^1$H NMR: $CDCl_3$ 400 MHz δ 7.23 (s, 1H), 7.08 (s, 1H), 3.95 (s, 3H), 3.81~3.83 (m, 6H), 2.89~2.92 (m, 4H).

Step 7: LiHMDS (0.8 mL, 0.8 mmol, 1 M) was added dropwise to a mixture of compound 7 (0.34 g, 0.8 mmol) and compound 8 (0.3 g, 0.8 mmol) in THF (20 mL) at −78° C. under $N_2$ atmosphere. The resulting mixture was warmed gradually to room temperature and continued to stir at −78° C. for 2 hrs. The reaction mixture was quenched with $H_2O$ and acidified to pH 3, the mixture was extracted with EtOAc and washed with brine, the organic layer was dried over anhydrous $Na_2SO_4$ and concentrated in vacuo to give crude compound 9 (0.5 g, crude), the crude product was used directly without further purification.

Step 8: The compound 9 (0.5 g, crude) in TFA (10 mL) was stirred at room temperature for 3 hrs. The reaction mixture was concentrated in vacuo and purified by column chromatography (PE:EtOAc=50:1) to give compound 10 (0.1 g, yield:20% from compound 7).

Step 9: To a mixture of compound 10 (0.1 g, 0.22 mmol) in MeOH (6 mL) and water (2 mL) was added NaOH (35 mg, 0.87 mmol) at room temperature, the resulting mixture was stirred at room temperature for 2 hrs. The reaction mixture was evaporated to remove methanol, the residue was diluted with water and washed with EtOAc, the aqueous layer was acidified with aq.HCl to pH<3, extracted with DCM. The organic layer was dried over anhydrous $Na_2SO_4$ and concentrated in vacuo, the crude product was purified by p-HPLC to give compound 11 (30 mg, yield: 32%)

$^1$H NMR: $CDCl_3$ 400 MHz δ 8.56 (d, 1H, J=4.4 Hz), 7.76 (d, 1H, J=8.8 Hz), 7.62~7.65 (m, 1H), 7.40 (s, 1H), 7.19 (s, 1H), 4.83 (br, 1H), 3.85~3.87 (m, 4H), 2.97~2.99 (m, 4H).

Example 2

Preparation of 4-hydroxy-3-[3-(2-methoxyethoxy)-2-(trifluoromethyl)phenyl]pyrano[3,2-b]pyridin-2-one (Hereinafter Also Referred to as Compound 19 Which Corresponds to Compound I-19 in the Table I Below)

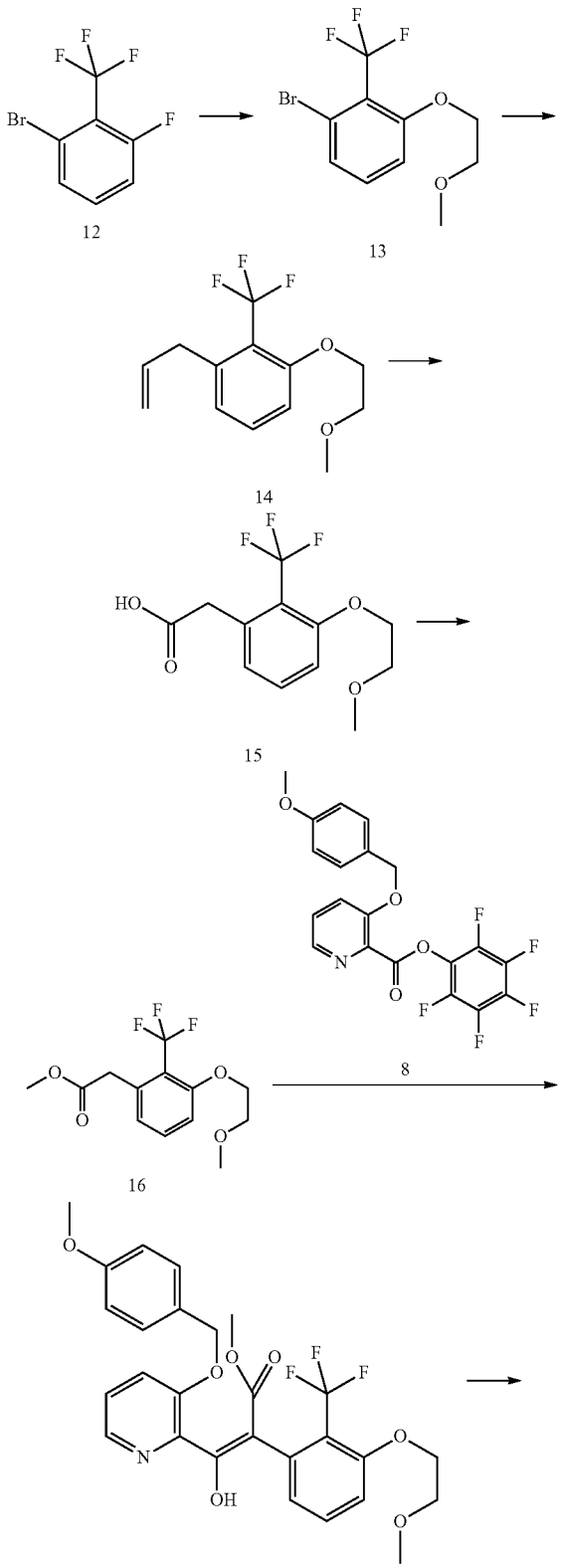

-continued

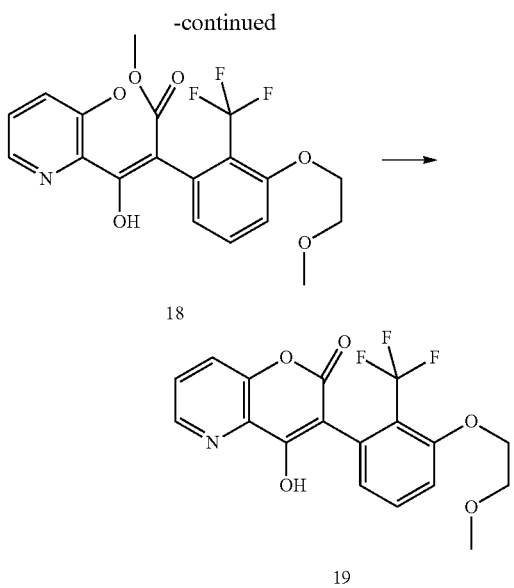

Step 1: To the 2-Methoxy-ethanol (1.41 g, 18.5 mol, 3 eq.) in DMF (10 ml) was added sodium hydride (800 mg, 6.1 mmol, 3 eq.) stirred at room temperature for 15 min, then compound 12 (1.5 g, 6.1 mmol) was added to above mixture, stirred at room temperature for 2 hours. The resulting solution was quenched with aq. NH$_4$Cl, separated between EtOAc and water. The organic solution was concentrated carefully at room temperature. The residue was 13 (1.6 g, 88%), that was used without further purification.

Step 2: To the solution of compound 13 (1.5 g, 5.05 mmol), LiCl (424 mg, 10.1 mmol) and Pd(PPh$_3$)Cl$_2$ (353 mg, 0.505 mmol) in 10 ml DMF, then allyl-tributyl-stannane (2.5 g, 7.6 mmol) was added to the reaction, and stirred under N$_2$ at 90° C. for 1 h. The reaction was quenched with aq.NH$_4$Cl, extracted with EtOAc, the organic layer was dried over Na$_2$SO$_4$, concentrated carefully at room temperature to give the crude product 14 (2.4 g, crude), then used directly.

$^1$H NMR: CDCl$_3$ 400 MHz δ 7.37 (t, 1H, J=7.6 Hz), 6.91 (d, 1H, J=7.6 Hz), 6.85 (d, 1H, J=7.6 Hz), 5.92~5.97 (m, 1H), 5.02~5.06 (m, 2H), 4.18~4.21 (m, 2H), 4.18~4.21 (m, 2H), 3.54~3.56 (m, 2H), 3.45 (s, 3H).

Step 3: A solution of the crude compound 14 (2.4 g) in 100 mL DCM was cooled to −78° C. and bubbled with O$_3$ until the solution turned blue, and O$_3$ was continued to bubble for 0.5 h. The mixture was purged with oxygen and N$_2$. The cooled solution was added dropwise to a previously-prepared Jones Reagent (To a suspension of 13.4 g CrO$_3$ in 300 mL acetone was added 10 mL conc. H$_2$SO$_4$ and 10 mL water under ice-cooling) at 0° C. The mixture was stirred at room temperature overnight. The reaction mixture was quenched with i-PrOH and filtered. The filtrate was concentrated and diluted with water, basified to pH 10, washed with EtOAc. The aqueous phase was acidified to pH 3, extracted with EtOAc and concentrated in vacuo to give 15 (560 mg, crude).

Step 4: To the solution of compound 14 (560 mg, crude) in methanol (10 ml) was added conc. H$_2$SO$_4$ (352 mg, 3.6 mmol), stirred at refluxed overnight. The resulting mixture was concentrated in vacuum, and partitioned with EtOAc/H$_2$O, the organic layer was washed by brine and dried over Na$_2$SO$_4$. The organic was concentrated in vacuum. The residue was purified by column (PE: EtOAc=15:1) to yield compound 16 (400 mg).

$^1$H NMR: CDCl$_3$ 400 MHz δ 7.394 (t, 1H, J=8 Hz), 7.003 (d, 1H, J=8 Hz), 6.841 (d, 1H, J=8 Hz), 4.179 (t, 2H), 3.828 (t, 2H), 3.788 (t, 2H), 3.704 (s, 3H), 3.455 (s, 3H).

Step 5: LiHMDS (5.5 ml, 5.5 mmol, 1 M) was added dropwise to a solution of compound 8 (400 mg, 1.37 mmol) and compound 16 (582 mg, 1.37 mmol) in dry THF (50 ml) at −78° C. under nitrogen. The mixture was continued to stir at −78° C., then warmed to room temperature and stirred for 2 hours. The mixture was concentrated in vacuum to give compound 17 (800 mg, crude) as a yellow syrup used directly without further purification.

Step 6: A solution of compound 17 (800 mg, crude) in TFA (10 ml) was stirred at room temperature for 1 hour. The mixture was adjusted to pH 7 with aqueous sodium hydroxide. Then it was used directly in the next step without further purification.

Step 7: To a solution of compound 18 in methanol/H$_2$O (30 ml/10 ml) was added sodium hydroxide (100 mg, 2.4 mmol) in portions at 0° C. The mixture was stirred at room temperature for 1 hour. Methanol was removed in vacuum. To the resulting aqueous phase was added water. It was washed with EtOAc and DCM. Then the aqueous phase was adjusted to pH 3 and extracted with DCM for 3 times. The resulting organic phase was dried over anhydrous sodium sulfate and concentrated in vacuum. The residue was purified by p-HPLC to give compound 19 as a yellow solid (120 mg, 23% three steps from compound 16).

$^1$H NMR: CDCl$_3$ 400 MHz δ 8.545 (d, 1H, J=8 Hz), 7.742 (d, 1H, J=8 Hz), 7.526~7.61 (m, 3H), 7.140 (d, 1H, J=8 Hz), 6.969 (d, 1H, J=8 Hz), 4.246 (t, 2H), 3.821 (t, 2H), 3.477 (s, 3H).

TABLE I

Compounds of the formula I.1A-1

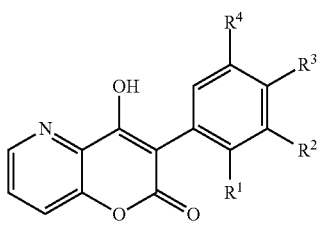

I.1A-1

| No. | R$^1$ | R$^2$ | R$^3$ | R$^4$ | MS m/z |
|---|---|---|---|---|---|
| I-1 | H | OCH$_2$O | | H | 284.0 |
| I-2 | H | CHCHCHCH | | H | 290.0 |

TABLE I-continued

Compounds of the formula I.1A-1

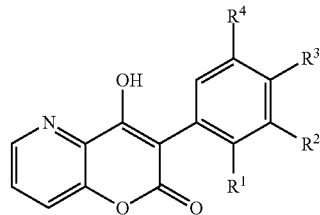

I.1A-1

| No. | R$^1$ | R$^2$ | R$^3$ | R$^4$ | MS m/z |
|---|---|---|---|---|---|
| I-3 | S—(4-Cl—Ph) | H | H | H | 282.0 |
| I-4 | O—(2-(3,6-(OMe)2-Pyrimidyl) | H | H | H | 394.1 |
| I-5 | CH$_2$—(2-thienyl) | H | H | H | 336.1 |
| I-6 | S—Ph | H | H | H | 348.0 |
| I-7 | S—(4-F—Ph) | H | H | H | 366.0 |
| I-8 | S—CF$_3$ | H | H | H | 340.0 |
| I-9 | CF$_3$ | 3-Isoxazolinyl | H | H | 377.0 |
| I-10 | Me | 3-Isoxazolinyl | H | H | 401.0 |
| I-11 | Cl | 3-Isoxazolinyl | SMe | H | 389.0 |
| I-12 | CF$_3$ | 3-Isoxazolyl | H | H | 375.0 |
| I-13 | Ph | H | H | H | 316.0 |
| I-14 | O—(2-(4-Br-Pyrimidyl)) | H | H | H | 411.0 |
| I-15 | H | OPh | H | H | 332.1 |
| I-16 | Me | 3-(5-Me-Isoxazolinyl) | SO$_2$Me | H | 415.1 |
| I-17 | H | COMe | H | H | 282.0 |
| I-18 | CF$_3$ | OCH$_2$CF$_3$ | H | H | 405.0 |
| I-19 | CF$_3$ | OCH$_2$CH$_2$OMe | H | H | 382.0 |
| I-20 | CF$_3$ | OCH$_2$(2-tetrahydrofuryl) | H | H | 408.0 |
| I-21 | Me | 3-Isoxazolinyl | CN | H | 348.0 |
| I-22 | Cl | 2-thiazolyl | SO$_2$Me | H | 343.1 |
| I-23 | Me | CHCH$_2$ | SO$_2$Me | H | 358.0 |
| I-24 | Me | C(spiro-O—N—CMe—CH$_2$—)CH$_2$SO$_2$ | H | H | 413.0 |
| I-25 | SCH$_2$CH$_2$C(Me)$_2$ | H | H | H | 373.1 |
| I-26 | CF$_3$ | 4-Morpholinyl | H | H | 393.1 |
| I-27 | CF$_3$ | OPh | H | H | 400.0 |
| I-28 | O—(2-Me—Ph) | H | H | H | 346.1 |
| I-29 | O—(CH$_2$—(4-(2-(4-F-pheny))thiazolyl) | H | H | H | 463.0 |
| I-30 | Me | SO$_2$NMe$_2$ | SO$_2$Me | H | 439.0 |
| I-31 | O—(2-(4,6-(OMe)$_2$)-triazinyl) | H | H | H | 395.1 |
| I-32 | CHCH-(5-(3-cyclopropyl)-oxazolyl) | H | H | H | 373.1 |
| I-33 | OCH$_2$CHCH$_2$ | H | H | H | 296.0 |
| I-34 | OCOMe | H | H | H | 298.0 |
| I-35 | H | OCH$_2$Ph | OMe | H | 376.1 |
| I-36 | OCH$_2$CH$_2$CH$_2$CH$_2$OPh | H | H | H | 404.1 |
| I-37 | OCH$_2$Ph | H | H | H | 346.0 |
| I-38 | Me | 3-Isoxazolinyl | CF$_3$ | H | 391.1 |
| I-39 | Me | 1-phtalimido | H | H | 399.1 |
| I-40 | Me | 1-tetrahydrophtalimido | H | H | 403.1 |
| I-41 | O—(3-(1-(4-Cl—Ph))-pyrrol | H | H | H | 432.0 |
| I-42 | CHCHCHN | | Me | H | 305.1 |
| I-43 | CHCHCHN | | Br | H | 371.0 |
| I-44 | CF$_3$ | SO$_2$Ph | H | H | 448.0 |
| I-45 | O—(4-(2-propyl-4-CF$_3$-pyrimidyl)) | H | H | H | 444.1 |
| I-46 | Cl | SO$_2$CH$_2$CH$_2$CMe$_2$ | | H | 405.0 |
| I-47 | Me | SO$_2$CH$_2$CH$_2$CMe$_2$ | H | H | 385.1 |
| I-48 | Me | Ph | H | H | 330.1 |
| I-49 | CF$_3$ | 4-Morpholinyl | H | Cl | 425.8 |
| I-50 | CF$_3$ | SO$_2$Me | H | H | 385.1 | wherein Me denotes methyl and Ph denotes phenyl

TABLE II

Compounds of the formula I.2A-1

I.2A-1

| No. | R¹ | R³ | R⁴ | MS m/z |
|---|---|---|---|---|
| II-1 | Cl | H | H | 274.1 |
| II-2 | Cl | Cl | H | 385.0 |

II. USE EXAMPLES

The herbicidal activity of the compounds of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this has been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments belonged to the following species:

| Bayer Code | Scientific name | English name |
|---|---|---|
| ABUTH | Abutilon theophrasti | velvetleaf |
| ALOMY | Alopecurus myosuroides | blackgrass |
| AMARE | Amaranthus retroflexus | common amaranth |
| CHEAL | Chenopodium album | lampsquaters |
| ECHCG | Echinochloa crus-galli | comon barnyardgrass |
| GALAP | Galium aparine | goosegrass |
| SETFA | Setaria faberi | Faber's foxtail |
| SETVI | Setaria viridis | green foxtail |

At an application rate of 3 kg/ha, the compound 11-2 applied by the post-emergence method, showed very good herbicidal activity against ABUTH.

At an application rate of 1 kg/ha, the compound I-4, applied by the post-emergence method, showed very good herbicidal activity against ALOMY.

At an application rate of 0.5 kg/ha, the compound I-9, applied by the post-emergence method, showed very good herbicidal activity against ALOMY.

At an application rate of 0.3 kg/ha, the compound I-22 applied by the post-emergence method, showed very good herbicidal activity against AMARE.

At an application rate of 0.336 kg/ha, the compound I-21 applied by the post-emergence method, showed very good herbicidal activity against AMARE.

At an application rate of 0.5 kg/ha, the compounds I-9, I-10, I-16, I-18, I-19, I-20, I-23, I-24, I-27, I-50, I-42, I-43 and I-44 applied by the post-emergence method, showed very good herbicidal activity against AMARE.

At an application rate of 0.23 kg/ha, the compound I-30, applied by the post-emergence method, showed very good herbicidal activity against CHEAL.

At an application rate of 0.25 kg/ha, the compounds I-12 and I-41, applied by the post-emergence method, showed very good herbicidal activity against CHEAL.

At an application rate of 0.336 kg/ha, the compound I-21, applied by the post-emergence method, showed very good herbicidal activity against CHEAL.

At an application rate of 0.5 kg/ha, the compounds I-10, I-16, I-18, I-19, I-20, I-23, I-24, I-27, I-38, I-50, I-42, I-43 and I-44, applied by the post-emergence method, showed very good herbicidal activity against CHEAL.

At an application rate of 0.177 kg/ha, the compound I-26, applied by the post-emergence method, showed very good herbicidal activity against ECHCG.

At an application rate of 0.5 kg/ha, the compound I-38, applied by the post-emergence method, showed very good herbicidal activity against ECHCG.

At an application rate of 0.25 kg/ha, the compound I-49, applied by the post-emergence method, showed very good herbicidal activity against GALAP.

At an application rate of 1 kg/ha, the compounds I-4, II-1 and I-25 applied by the post-emergence method, showed very good herbicidal activity against SETFA.

At an application rate of 0.25 kg/ha, the compound I-49, applied by the post-emergence method, showed very good herbicidal activity against SETVI.

The invention claimed is:
1. A compound of formula I

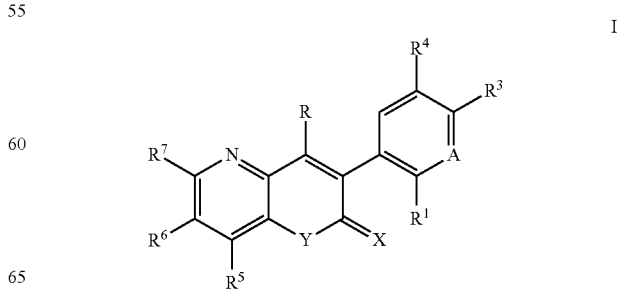

in which:

R is O—$R^A$, S(O)$_n$—$R^A$ or O—S(O)$_n$—$R^A$;

$R^A$ is hydrogen, $C_1$-$C_4$-alkyl, Z—$C_3$-$C_6$-cycloalkyl, $C_1$-$C_4$-haloalkyl, $C_2$-$C_6$-alkenyl, Z—$C_3$-$C_6$-cycloalkenyl, $C_2$-$C_6$-alkynyl, Z-(tri-$C_1$-$C_4$-alkyl)silyl, Z—C(=O)—$R^a$, Z—$NR^i$—C(O)—$NR^iR^{ii}$, Z—P(=O)($R^a$)$_2$, $NR^iR^{ii}$, a 3- to 7-membered monocyclic or 9- or 10-membered bicyclic saturated, unsaturated or aromatic heterocycle which contains 1, 2, 3 or 4 heteroatoms selected from the group consisting of O, N and S and which may be partially or fully substituted by groups $R^a$ and/or $R^b$, $R^a$ is hydrogen, OH, $C_1$-$C_8$-alkyl, $C_1$-$C_4$-haloalkyl, Z—$C_3$-$C_6$-cycloalkyl, $C_2$-$C_8$-alkenyl, Z—$C_5$-$C_6$-cycloalkenyl, $C_2$-$C_8$-alkynyl, Z—$C_1$-$C_6$-alkoxy, Z—$C_1$-$C_4$-haloalkoxy, Z—$C_3$-$C_8$-alkenyloxy, Z—$C_3$-$C_8$-alkynyloxy, $NR^iR^{ii}$, $C_1$-$C_6$-alkylsulfonyl, Z-(tri-$C_1$-$C_4$-alkyl)silyl, Z-phenyl, Z-phenoxy, Z-phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^b$;

$R^i$, $R^{ii}$ independently of one another are hydrogen, $C_1$-$C_8$-alkyl, $C_1$-$C_4$-haloalkyl, $C_3$-$C_8$-alkenyl, $C_3$-$C_8$-alkynyl, Z—$C_3$-$C_6$-cycloalkyl, Z—$C_1$-$C_8$-alkoxy, Z—$C_1$-$C_8$-haloalkoxy, Z—C(=O)—$R^a$, Z-phenyl, a 3- to 7-membered monocyclic or 9- or 10-membered bicyclic saturated, unsaturated or aromatic heterocycle which contains 1, 2, 3 or 4 heteroatoms selected from the group consisting of O, N and S and which is attached via Z; or $R^i$ and $R^{ii}$ together with the nitrogen atom to which they are attached form a 5- or 6-membered monocyclic or 9- or 10-membered bicyclic heterocycle which contains 1, 2, 3 or 4 heteroatoms selected from the group consisting of O, N and S;

Z is a covalent bond or $C_1$-$C_4$-alkylene;

n is 0, 1 or 2;

$R^1$ is cyano, halogen, nitro, $C_1$-$C_6$-alkyl, $C_2$-$C_6$-alkenyl, $C_2$-$C_6$-alkynyl, $C_1$-$C_6$-haloalkyl, Z—$C_1$-$C_6$-alkoxy, Z—$C_1$-$C_4$-alkoxy-$C_1$-$C_4$-alkoxy, Z—$C_1$-$C_4$-alkylthio, Z—$C_1$-$C_4$-alkylthio-$C_1$-$C_4$-alkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, S(O)$_n$$R^{bb}$, Z-phenoxy, or Z-heterocyclyloxy, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^b$;

$R^{bb}$ is $C_1$-$C_8$-alkyl, $C_2$-$C_6$-alkenyl, $C_2$-$C_6$-alkynyl, $C_2$-$C_6$-haloalkenyl, $C_2$-$C_6$-haloalkynyl or $C_1$-$C_6$-haloalkyl and n is 0, 1 or 2;

A is N or C—$R^2$;

$R^2$ is $Z^1$-phenyl, phenoxy or $Z^1$-heterocyclyl, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^b$; or $R^2$ is $C_1$-$C_8$-alkyl, $C_2$-$C_8$-haloalkyl, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_2$-$C_8$-haloalkenyl, $C_2$-$C_8$-haloalkynyl, $C_2$-$C_6$-alkoxy, Z—$C_1$-$C_4$-alkoxy-$C_1$-$C_4$-alkoxy, Z—$C_1$-$C_4$-haloalkoxy-$C_1$-$C_4$-alkoxy, $C_2$-$C_6$-haloalkoxy, $C_3$-$C_6$-alkenyloxy, $C_3$-$C_6$-alkynyloxy, $C_2$-$C_6$-alkylthio, $C_2$-$C_6$-haloalkylthio, Z—C(=O)—$R^a$, or S(O)$_{1-2}$$R^{bb}$;

$Z^1$ is a covalent bond, $C_1$-$C_4$-alkyleneoxy, $C_1$-$C_4$-oxyalkylene or $C_1$-$C_4$-alkyleneoxy-$C_1$-$C_4$-alkylene;

$R^b$ independently of one another are Z—CN, Z—OH, Z—NO$_2$, Z-halogen, oxo (=O), =N—$R^a$, $C_1$-$C_8$-alkyl, $C_1$-$C_4$-haloalkyl, $C_2$-$C_8$-alkenyl, $C_2$-$C_8$-alkynyl, Z—$C_1$-$C_8$-alkoxy, Z—$C_1$-$C_8$-haloalkoxy, Z—$C_3$-$C_{10}$-cycloalkyl, O—Z—$C_3$-$C_{10}$-cycloalkyl, Z—C(=O)—$R^a$, $NR^iR^{ii}$, Z-(tri-$C_1$-$C_4$-alkyl)silyl, Z-phenyl and S(O)$_n$$R^{bb}$, or two groups $R^b$ may together form a ring which has three to six ring members and, in addition to carbon atoms, contain heteroatoms from the group consisting of O, N and S and may be unsubstituted or substituted by further groups $R^b$; or $R^2$ together with the group attached to the adjacent carbon atom form a five- to ten-membered saturated or partially or fully unsaturated mono- or bicyclic ring which, in addition to carbon atoms, may contain 1, 2 or 3 heteroatoms selected from the group consisting of O, N and S and may be substituted by further groups $R^b$;

$R^3$ is hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_2$-$C_4$-alkenyloxy, $C_2$-$C_4$-alkynyloxy, or S(O)$_n$$R^{bb}$;

$R^4$ is hydrogen, halogen or $C_1$-$C_4$-haloalkyl;

$R^5$ is hydrogen, $C_1$-$C_4$-alkyl, $C_1$-$C_4$-haloalkyl, $C_1$-$C_4$-alkoxy, $C_1$-$C_4$-alkylthio, $C_1$-$C_4$-haloalkoxy, or $C_1$-$C_4$-haloalkylthio;

$R^6$,$R^7$ independently of one another are hydrogen, halogen or $C_1$-$C_4$-alkyl;

Y is O or S;

X is O, S or N—$R^x$;

$R^x$ is hydrogen, $C_1$-$C_6$-alkyl, $C_1$-$C_4$-haloalkyl, $C_2$-$C_6$-alkenyl, $C_3$-$C_6$-alkynyl, Z—$C_3$-$C_{10}$-cycloalkyl, $C_1$-$C_6$-alkoxy-$C_1$-$C_6$-alkyl, $C_1$-$C_6$-cyanoalkyl, Z-phenyl, Z—C(=O)—$R^{a2}$ or tri-$C_1$-$C_4$-alkylsilyl;

$R^{a2}$ is $C_1$-$C_6$-alkyl, $C_1$-$C_4$-haloalkyl, Z—$C_1$-$C_6$-alkoxy, Z—$C_1$-$C_4$-haloalkoxy or $NR^iR^{ii}$;

where in the groups $R^A$ and their subsubstituents, the carbon chains and/or the cyclic groups may be partially or fully substituted by groups $R^b$, or an N-oxide or an agriculturally suitable salt thereof.

2. The compound of claim 1 in which A is $CR^2$.

3. The compound of claim 2 in which $R^2$ is an optionally substituted five- or six-membered saturated, partially unsaturated or aromatic heterocycle which contains 1, 2, 3 or 4 heteroatoms selected from the group consisting of O, N and S.

4. The compound of claim 2 in which $R^2$ is

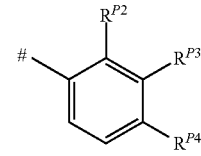

in which # denotes the bond through which the group $R^2$ is attached and:

$R^{P2}$ is H or F;

$R^{P3}$ is H, F, Cl or $OCH_3$; and $R^{P4}$ is H, F, Cl, $CH_3$, $CF_3$, $OCH_3$, $OCH_2OCH_3$ or $OCH_2CH_2OCH_3$.

5. The compound of claim 3 in which $R^2$ is an optionally $R^b$-substituted heterocycle selected from the group consisting of isoxazoline, tetrazolone, 1,2-dihydrotetrazolone, 1,4-dihydrotetrazolone, tetrahydrofuran, dioxolane, piperidine, morpholine, piperazine, isoxazole, pyrazole, thiazole, oxazole, furyl, pyridine and pyrazine.

6. The compound of claim 5 in which the groups $R^b$ are selected from the group consisting of $C_1$-$C_4$-alkyl, $C_1$-$C_4$-haloalkyl, $C_1$-$C_4$-alkoxy, $C_1$-$C_4$-alkoxy-$C_1$-$C_4$-alkyl and $C_1$-$C_4$-alkylthio-$C_1$-$C_4$-alkyl.

7. The compound of claim 2 in which $R^2$ is an aliphatic group selected from the group consisting of $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_2$-$C_4$-alkoxy, $C_2$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $S(O)_2$—$C_1$-$C_8$-alkyl and $S(O)_2$—$C_1$-$C_8$-haloalkyl.

8. The compound of claim 1 in which $R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl; and $R^3$ is H, halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, or $C_1$-$C_4$-alkylsulfonyl.

9. The compound of claim 2 in which $R^2$ together with $R^1$ or $R^3$ forms an optionally $R^b$-substituted five- to ten-membered mono- or bicyclic, partially unsaturated ring which contains 1, 2, 3 or 4 heteroatoms selected from the group consisting of O, N and S.

10. The compound of claim 7 in which the ring substituted by groups $R^1$, $R^2$, $R^3$ and $R^4$ corresponds to one of groups A to L

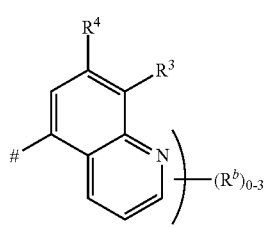

A

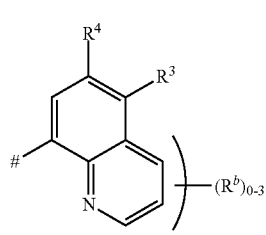

B

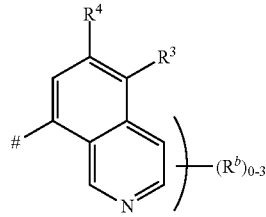

C

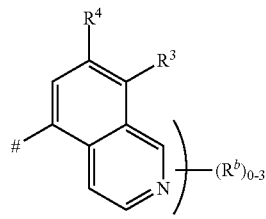

D

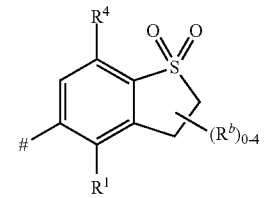

E

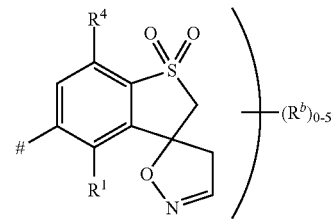

F

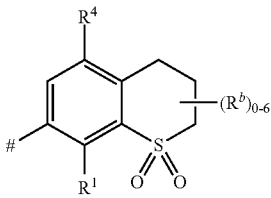

G

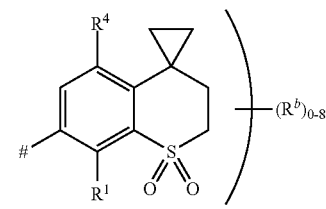

H

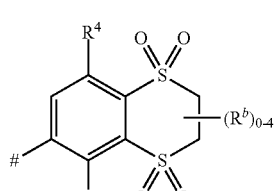

I

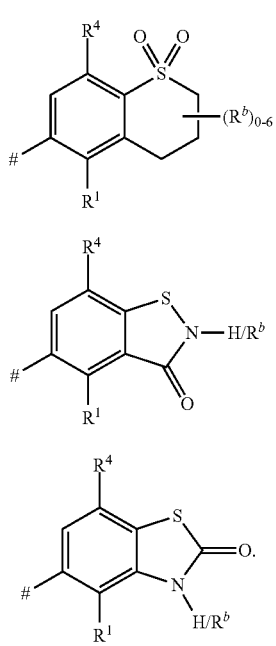

11. The compound of claim 1 in which A is N.

12. The compound of claim 11 in which $R^1$ is nitro, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl; and $R^3$ is H, CN, $NO_2$, $C_1$-$C_4$-alkyl, $C_1$-$C_4$-haloalkyl, $C_1$-$C_4$-alkoxy, $C_1$-$C_4$-alkylthio or $C_1$-$C_4$-alkylsulfonyl.

13. The compound of claim 1 in which

X,Y independently of one another are O or S and $R^4, R^5, R^6, R^7$ are H.

14. A composition comprising a herbicidally effective amount of a compound of claim 1 and auxiliaries customary for formulating crop protection agents.

15. A method for controlling unwanted vegetation which comprises allowing a herbicidally effective amount of a compound of claim 1 to act on plants, their seed and/or their habitat.

16. The method of claim 15, wherein in the compound of formula I, A is $CR^2$.

17. The method of claim 16, wherein in the compound of formula I, $R^2$ is an optionally substituted five- or six-membered saturated, partially unsaturated or aromatic heterocycle which contains 1, 2, 3 or 4 heteroatoms selected from the group consisting of O, N and S.

18. The method of claim 16, wherein in the compound of formula I, $R^2$ is

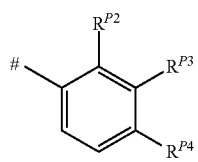

in which #denotes the bond through which the group $R^2$ is attached and:

$R^{P2}$ is H or F;

$R^{P3}$ is H, F, Cl or $OCH_3$; and $R^{P4}$ is H, F, Cl, $CH_3$, $CF_3$, $OCH_3$, $OCH_2OCH_3$ or $OCH_2CH_2OCH_3$.

19. The method of claim 17, wherein in the compound of formula I, $R^2$ is an optionally Rb-substituted heterocycie selected from the group consisting of isoxazoline, tetrazolone, 1,2-dihydrotetrazolone, 1,4-dihydrotetrazolone, tetrahydrofuran, dioxolane, piperidine, morpholine, piperazine, isoxazole, pyrazole, thiazole, oxazole, furyl, pyridine and pyrazine.

20. The method of claim 19, wherein in the compound of formula I, the groups $R^b$ are selected from the group consisting of $C_1$-$C_4$-alkyl, $C_1$-$C_4$-haloalkyl, $C_1$-$C_4$-alkoxy, $C_1$-$C_4$-alkoxy-$C_1$-$C_4$-alkyl and $C_1$-$C_4$-alkylthio-$C_1$-$C_4$-alkyl.

21. The method of claim 16, wherein in the compound of formula I, $R^2$ is an aliphatic group selected from the group consisting of $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_2$-$C_4$-alkoxy, $C_2$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $S(O)_2$—$C_1$-$C_8$-alkyl and $S(O)_2$—$C_1$-$C_8$-haloalkyl.

22. The method of claim 15, wherein in the compound of formula I, $R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl; and $R^3$ is H, halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, or $C_1$-$C_4$-alkylsulfonyl.

23. The method of claim 16, wherein in the compound of formula I, $R^2$ together with $R^1$ or $R^3$ forms an optionally $R^b$-substituted five- to ten-membered mono- or bicyclic, partially unsaturated ring which contains 1, 2, 3 or 4 heteroatoms selected from the group consisting of O, N and S.

24. The method of claim 15, wherein in the compound of formula I, the ring substituted by groups $R^1$, $R^2$, $R^3$ and $R^4$ corresponds to one of groups A to L

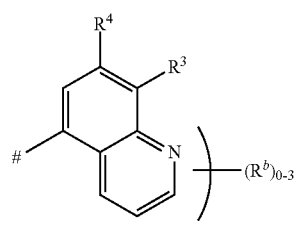

A

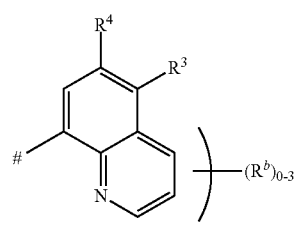

B

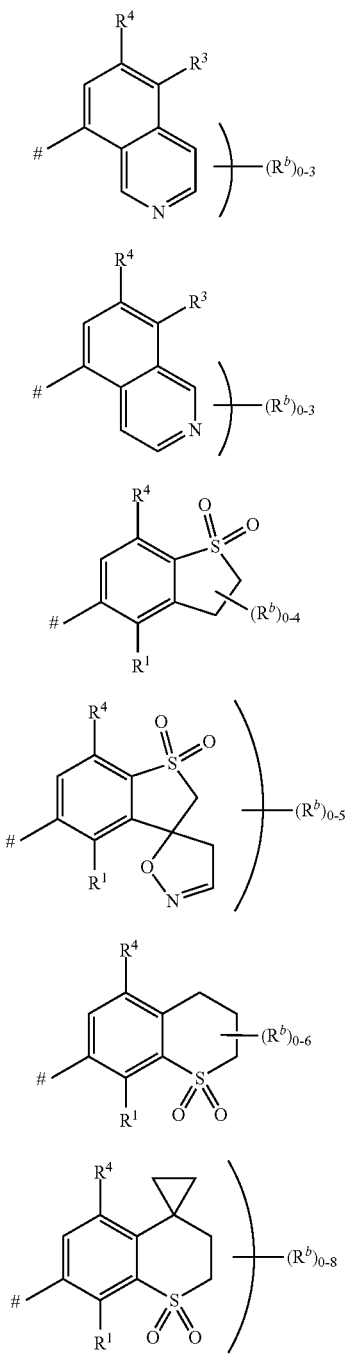

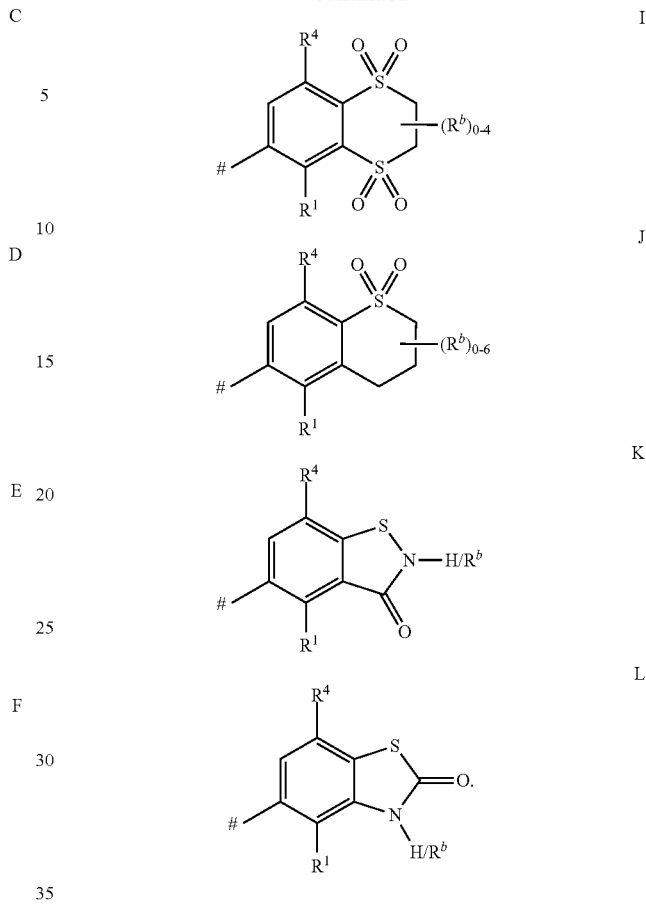

25. The method of claim 15, wherein in the compound of formula I, A is N.

26. The method of claim 25, wherein in the compound of formula I, $R^1$ is nitro, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl; and $R^3$ is H, CN, $NO_2$, $C_1$-$C_4$-alkyl, $C_1$-$C_4$-haloalkyl, $C_1$-$C_4$-alkoxy, $C_1$-$C_4$-alkylthio or $C_1$-$C_4$-alkylsulfonyl.

27. The method of claim 15, wherein in the compound of formula I,

X,Y independently of one another are O or S and $R^4,R^5,R^6,R^7$ are H.

\* \* \* \* \*